US009394482B2

(12) United States Patent
Gotoh et al.

(10) Patent No.: US 9,394,482 B2
(45) Date of Patent: Jul. 19, 2016

(54) POLYMERIZABLE COMPOUND, POLYMERIZABLE COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Yasuyuki Gotoh, Tokyo (JP); Takahiro Kubo, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

(21) Appl. No.: 14/503,741

(22) Filed: Oct. 1, 2014

(65) Prior Publication Data

US 2015/0102259 A1 Apr. 16, 2015

(30) Foreign Application Priority Data

Oct. 16, 2013 (JP) ................................ 2013-215497

(51) Int. Cl.

*C09K 19/32* (2006.01)
*C09K 19/34* (2006.01)
*C07C 69/54* (2006.01)
*C07C 69/753* (2006.01)

(Continued)

(52) U.S. Cl.

CPC ............. *C09K 19/3028* (2013.01); *C07C 69/54* (2013.01); *C09K 19/3066* (2013.01); *C09K 19/32* (2013.01); *C09K 19/322* (2013.01); *C09K 19/3402* (2013.01); *C09K 19/52* (2013.01); *C07C 69/604* (2013.01); *C07C 69/753* (2013.01); *C08F 220/18* (2013.01); *C08F 2222/1046* (2013.01); *C09K 2019/0411* (2013.01); *C09K 2019/0448* (2013.01); *C09K 2019/0466* (2013.01); *C09K 2019/122* (2013.01); *C09K 2019/123* (2013.01); *C09K 2019/301* (2013.01); *C09K 2019/3004* (2013.01); *C09K 2019/304* (2013.01); *C09K 2019/308* (2013.01); *C09K 2019/3009* (2013.01); *C09K 2019/3016* (2013.01); *C09K 2019/3019* (2013.01); *C09K 2019/3021* (2013.01); *C09K 2019/3027* (2013.01); *C09K 2019/3042* (2013.01); *C09K 2019/3071* (2013.01); *C09K 2019/3078* (2013.01); *C09K 2019/3422* (2013.01); *C09K 2019/3425* (2013.01)

(58) Field of Classification Search

CPC ........... C09K 19/3028; C09K 19/3066; C09K 19/32; C09K 19/322; C09K 19/3402; C09K 19/52; C09K 2019/0411; C09K 2019/0448; C09K 2019/0466; C09K 2019/122; C09K 2019/123; C09K 2019/3004; C09K 2019/3009; C09K 2019/301; C09K 2019/3016; C09K 2019/3019; C09K 2019/3021; C09K 2019/3027; C09K 2019/304; C09K 2019/3042; C09K 2019/3071; C09K 2019/3078; C09K 2019/308; C09K 2019/3422; C09K 2019/3425; C07C 69/54; C07C 69/603; C07C 69/753

See application file for complete search history.

(56) References Cited

U.S. PATENT DOCUMENTS

| | | | | |
|---|---|---|---|---|
| 9,157,027 B2 * | 10/2015 | Goto | ...................... | C09K 19/12 |
| 2013/0277609 A1 * | 10/2013 | Goto | ...................... | C09K 19/12 252/299.61 |
| 2014/0176896 A1 | 6/2014 | Feng et al. | | |

FOREIGN PATENT DOCUMENTS

CN 102888231 1/2013

*Primary Examiner* — Shean C Wu

(74) *Attorney, Agent, or Firm* — Greenblum & Bernstein, P.L.C.

(57) ABSTRACT

An object is to provide a liquid crystal compound having high polymerization reactivity, a high conversion ratio and high solubility in a liquid crystal composition, a polymerizable composition containing the compound, a liquid crystal composite prepared using the composition, and a liquid crystal display device having the composite. A solution is a polymerizable compound represented by formula (1).

(1)

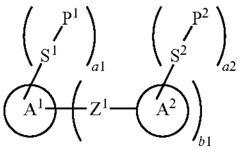

In formula (1), $P^1$ and $P^2$ are identically group (P-1), (P-2) or (P-3), and in formula (P-1), M is hydrogen, fluorine, $—CH_3$ or $—CF_3$;

(P-1)

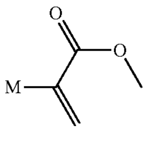

(P-2)

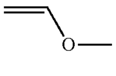

(P-3)

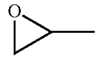

$S^1$ and $S^2$ are a single bond, alkylene having 1 to 6 carbons or the like; a1, a2 and b1 are 0, 1, 2, 3 or 4, and a sum of a1 and a2 is 4; ring $A^1$ is naphthalene, anthracene or phenanthrene; and ring $A^2$ is cyclohexyl, phenyl, naphthyl, anthracenyl or phenanthrenyl; and $Z^1$ is a single bond, —CO—, —COO— or the like.

16 Claims, No Drawings

(51) Int. Cl.

| | |
|---|---|
| ***C09K 19/30*** | (2006.01) |
| ***C09K 19/52*** | (2006.01) |
| *C07C 69/604* | (2006.01) |
| *C08F 220/18* | (2006.01) |
| *C08F 222/10* | (2006.01) |
| *C09K 19/04* | (2006.01) |
| *C09K 19/12* | (2006.01) |

POLYMERIZABLE COMPOUND, POLYMERIZABLE COMPOSITION AND LIQUID CRYSTAL DISPLAY DEVICE

TECHNICAL FIELD

The invention relates to a polymerizable compound, a polymerizable composition containing the polymerizable compound and a liquid crystal composition, a liquid crystal composite prepared using the polymerizable composition, a liquid crystal display device and so forth.

BACKGROUND ART

A liquid crystal display device utilizes optical anisotropy, dielectric anisotropy and so forth of a liquid crystal molecule in a liquid crystal composition. A classification based on an operating mode of the liquid crystal molecule includes a phase change (PC) mode, a twisted nematic (TN) mode, a super twisted nematic (STN) mode, a bistable twisted nematic (BTN) mode, an electrically controlled birefringence (ECB) mode, an optically compensated bend (OCB) mode, an in-plane switching (IPS) mode, a fringe field switching (FFS) mode and a vertical alignment (VA) mode.

A liquid crystal display device having a mode in which a polymer is combined with the liquid crystal composition is known. Examples of the modes include a polymer sustained alignment (PSA) mode or a polymer stabilized (PS) mode. In the liquid crystal display device having the mode, the liquid crystal composition to which a polymerizable compound is added is injected into a display device. The display device is irradiated with ultraviolet light in a state of applying voltage between electrodes to polymerize the polymerizable compound, and thus the polymer formed in the liquid crystal composition. According to the method, a liquid crystal display device in which a response time is shortened and image sticking is improved is obtained.

The method can be applied to liquid crystal display devices having various operating modes, and such modes are known as a PS-TN mode, a PS-IPS mode, a PS-FFS mode, a PSA-VA mode and a PSA-OCB mode. The polymerizable compound to be used in the device having such a mode is considered to have high capacity for aligning liquid crystal molecules, but solubility in the liquid crystal composition is far from high. An attempt has been so far made on improving the solubility in the liquid crystal composition, but when the solubility is improved, polymerization reactivity tends to decrease. Therefore, development has been desired for a polymerizable compound having a suitable balance between the solubility and the polymerization reactivity.

CITATION LIST

Patent Literature

Patent literature No. 1: CN 102888231 A.

SUMMARY OF INVENTION

Technical Problem

A first object of the invention is to provide a polymerizable compound having high polymerization reactivity, a high conversion ratio and high solubility in a liquid crystal composition. A second object is to provide a liquid crystal composite satisfying at least one of physical properties such as a high maximum temperature of a nematic phase, a low minimum temperature of the nematic phase, small viscosity, suitable optical anisotropy, large dielectric anisotropy, a suitable elastic constant, large specific resistance and suitable pretilt. The object is to provide a liquid crystal composite having a suitable balance regarding at least two of the physical properties. A third object is to provide a liquid crystal display device having a wide temperature range in which the devise can be used, a short response time, a high voltage holding ratio, a low threshold voltage, a large contrast ratio and a long service life.

Solution to Problem

The invention concerns a polymerizable compound represented by formula (1), a polymerizable composition containing the compound and a liquid crystal composition, a liquid crystal composite prepared using the polymerizable composition, a liquid crystal display device and so forth:

(1)

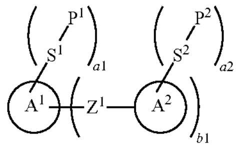

wherein, in formula (1), all of a1 moieties of $P^1$ and a2 moieties of $P^2$ are identically a group selected from groups represented by formulas (P-1), (P-2) and (P-3), and in formula (P-1), M is hydrogen, fluorine, $—CH_3$ or $—CF_3$:

(P-1)

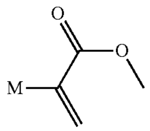

(P-2)

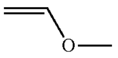

(P-3)

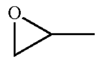

$S^1$ and $S^2$ are independently a single bond or alkylene having 1 to 6 carbons, and in the alkylene, at least one of $—CH_2—$ may be replaced by —O—, —COO— or —OCO—, at least one of $—CH_2—CH_2—$ may be replaced by —CH═CH— or —C≡C—, and in the groups, at least one of hydrogen may be replaced by halogen;

a1 and a2 are independently 0, 1, 2, 3 or 4, and a sum of a1 and a2 is 4;

ring $A^1$ is naphthalene, anthracene or phenanthrene, ring $A^2$ is cyclohexyl, phenyl, naphthyl, anthracenyl or phenanthrenyl, and in the rings, at least one of hydrogen may be replaced by halogen, alkyl having 1 to 10 carbons, or alkyl having 1 to 10 carbons in which at least one of hydrogen is replaced by halogen;

$Z^1$ is a single bond, —CO—, —COO—, —OCO—, —CH═CH—, $—CH═C(CH_3)—$, $—C(CH_3)═CH—$, $—C(CH_3)═C(CH_3)—$, —CH═CH—COO—, —OCO—CH═CH—, $—C(CH_3)═CH—COO—$, $—OCO—CH═CH(CH_3)—$, $—CH—C(CH_3)—COO—$, $—OCO—C(CH_3)═CH—$, $—C(CH_3)═C(CH_3)—COO—$, —OCO—C $(CH_3)$=C$(CH_3)$—, —CH=CH—CO—, —CO—CH=CH—, —CH=CH—$CH_2O$—, —$OCH_2$—CH=CH—, —CH=CH—$OCH_2$— or —$CH_2O$—CH=CH—; and b1 is 0, 1, 2, 3 or 4.

The invention further concerns a polymer obtained from the compound.

Advantageous Effects of Invention

A first advantage of the invention is a polymerizable compound having high polymerization reactivity, a high conversion ratio and high solubility in a liquid crystal composition. A second advantage is a liquid crystal composite satisfying at least one of physical properties such as a high maximum temperature of a nematic phase, a low minimum temperature of the nematic phase, small viscosity, suitable optical anisotropy, large dielectric anisotropy, a suitable elastic constant, large specific resistance and suitable pretilt. The advantage is the liquid crystal composite having a suitable balance regarding at least two of the physical properties. A third advantage is a liquid crystal display device having a wide temperature range in which the device can be used, a short response time, a high voltage holding ratio, a low threshold voltage, a large contrast ratio and a long service life.

DESCRIPTION OF EMBODIMENTS

Usage of terms herein is as described below. "Liquid crystal compound" is a generic term for a non-polymerizable compound having a liquid crystal phase such as a nematic phase and a smectic phase, and a non-polymerizable compound having no liquid crystal phase but being mixed for the purpose of adjusting physical properties of a liquid crystal composition, such as a maximum temperature, a minimum temperature, viscosity and dielectric anisotropy. The compound has a 6-membered ring such as 1,4-cyclohexylene and 1,4-phenylene, and has rod like molecular structure. "Liquid crystal composition" is a mixture of the liquid crystal compounds. "Polymerizable compound" includes a compound to be added to the composition for the purpose of forming a polymer. "Polymerizable composition" includes a composition containing the polymerizable compound, and for example, a mixture of the polymerizable compound, the liquid crystal composition and an additive. "Liquid crystal composite" includes a composite to be formed by polymerization of the polymerizable composition. "Liquid crystal display device" is a generic term for a liquid crystal display panel and a liquid crystal display module. "Maximum temperature of the nematic phase" is a phase transition temperature between the nematic phase and an isotropic phase in the liquid crystal composition, the polymerizable composition or the liquid crystal composite, and may be occasionally abbreviated as "maximum temperature." "Minimum temperature of the nematic phase" may be abbreviated as "minimum temperature." "Polymerization reactivity" means a degree of ease when a reactant is polymerized. "Conversion ratio" means a weight ratio of a reactant consumed by a chemical reaction to a total reactant.

The liquid crystal composition is prepared by mixing the liquid crystal compounds. A ratio (content) of the liquid crystal compounds is expressed in terms of weight percent (% by weight) based on the weight of the liquid crystal composition. An additive such as an optically active compound, an antioxidant, an ultraviolet light absorber, a light stabilizer, a heat stabilizer, an antifoaming agent, a polymerization initiator and a polymerization inhibitor is added to the composition, when necessary. A ratio (amount of addition) of the additive is expressed in terms of weight percent (% by weight) based on the weight of the liquid crystal composition in a manner similar to the ratio of the liquid crystal compounds. Weight parts per million (ppm) may be occasionally used. A ratio of the polymerization initiator and the polymerization inhibitor is exceptionally expressed based on the weight of the polymerizable compound.

A compound represented by formula (1) may be occasionally abbreviated as compound (1). The abbreviation is also applied to a compound represented by formula (2) or the like. Compound (1) means one compound or two or more compounds represented by formula (1). In formulas (1) to (15), a symbol surrounded a circle or a hexagonal shape, such as $A^1$, $B^1$ and $C^1$ each corresponds to ring $A^1$, ring $B^1$ or ring $C^1$. In formula (1), a diagonal line crossing the circle of ring $A^1$ means that a $P^1$-$S^1$ group can arbitrarily select a bonding position on a ring. The rule is also applied to a $P^2$-$S^2$ group or the like. The rule is also applied to a diagonal line (or transverse line) crossing a condensed ring such as a naphthalene ring in formula (1-1). In formula (1), a subscript such as a1 represents the number of groups bonding with ring $A^1$ or the like. Ring $A^1$ or the like serves as a group having valence in the number of groups bonding therewith. When a1 is 2, two of $S^1$ exist on ring $A^1$. Two groups represented by two of $S^1$ may be identical or different. The rule is also applied to a case where a1 is larger than 2. The rule is also applied to any other group. A symbol of $R^{11}$ is used for a plurality of formulas, such as formula (2) and formula (3). In the compounds, two terminal groups represented by two of arbitrary $R^{11}$ may be identical or different. In formula (5), when i is 2, two symbols $C^1$ exist in one formula. In the compound, two rings represented by two symbols $C^1$ may be identical or different. The rule is also applied to a symbol such as $Z^{14}$.

An expression "at least one of 'A' may be replaced by 'B'" means that a position of 'A' is arbitrary when the number of 'A' is 1, and that positions thereof can be selected without restriction also when the number of 'A' is 2 or more. An expression "at least one of A may be replaced by B, C or D" means a case where at least one of A is replaced by B, a case where at least one of A is replaced by C, and a case where at least one of A is replaced by D, and further a case where a plurality of A are replaced by at least two of B, C and D. Specific examples of alkyl in which at least one of —$CH_2$— (or —$CH_2CH_2$—) may be replaced by —O— (or —CH—CH—) include alkyl, alkenyl, alkoxy, alkoxyalkyl, alkoxyalkenyl and alkenyloxyalkyl. In addition, a case where two of consecutive —$CH_2$— is replaced by —O— to form —O—O— is not preferred. A case where —$CH_2$— of a methyl moiety (—$CH_2$—H) in alkyl or the like is replaced by —O— to form —O—H is not preferred, either.

Then, 2-fluoro-1,4-phenylene means two divalent groups described below. In a chemical formula, fluorine may be leftward (L) or may be rightward (R). The rule is also applied to a divalent group of an asymmetrical ring such as tetrahydropyran-2,5-diyl.

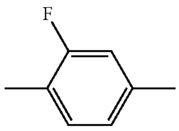
(L)

-continued (R)

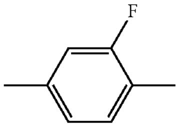

The invention includes the content as described in items below.

Item 1. A compound represented by formula (1):

(1)

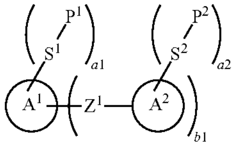

wherein, in formula (1), all of a1 moieties of $P^1$ and a2 moieties of $P^2$ are identically a group selected from groups represented by formulas (P-1), (P-2) and (P-3), and in formula (P-1), M is hydrogen, fluorine, $—CH_3$ or $—CF_3$:

(P-1)

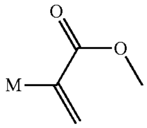

(P-2)

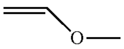

(P-3)

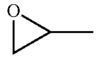

$S^1$ and $S^2$ are independently a single bond or alkylene having 1 to 6 carbons, and in the alkylene, at least one of $—CH_2—$ may be replaced by —O—, —COO— or —OCO—, at least one of $—CH_2—CH_2—$ may be replaced by —CH═CH— or —C≡C—, and at least one of hydrogen may be replaced by halogen;

a1 and a2 are independently 0, 1, 2, 3 or 4, and a sum of a1 and a2 is 4;

ring $A^1$ is naphthalene, anthracene or phenanthrene, ring $A^2$ is cyclohexyl, phenyl, naphthyl, anthracenyl or phenanthrenyl, and in the rings, at least one of hydrogen may be replaced by halogen, alkyl having 1 to 10 carbons, or alkyl having 1 to 10 carbons in which at least one of hydrogen is replaced by halogen;

$Z^1$ is a single bond, —CO—, —COO—, —OCO—, —CH═CH—, —C≡C—, $—CH═C(CH_3)—$, $—C(CH_3)═CH—$, $—C(CH_3)═C(CH_3)—$, —CH═CH—COO—, —OCO—CH═CH—, $—C(CH_3)═CH—COO—$, $—OCO—CH═CH(CH_3)—CH═C(CH_3)—COO—$, $—OCO—C(CH_3)═CH—$, $—C(CH_3)═C(CH_3)—COO—$, $—OCO—C(CH_3)═C(CH_3)—$, —CH═CH—CO—, —CO—CH═CH—, $—CH═CH—CH_2O—$, $—OCH_2—CH═CH—$, $—CH═CH—OCH_2—$ or $—CH_2O—CH═CH—$; and b1 is 0, 1, 2, 3 or 4.

Item 2. The compound according to item 1, wherein, in formula (1), all of a1 moieties of $P^1$ and a2 moieties of $P^2$ are identically a group represented by formula (P-1), and in formula (P-1), M is hydrogen, fluorine, $—CH_3$ or $—CF_3$:

(P-1)

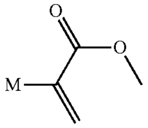

$S^1$ and $S^2$ are independently a single bond or alkylene having 1 to 6 carbons, and in the alkylene, at least one of $—CH_2—$ may be replaced by —O—, —COO— or —OCO—, at least one of $—CH_2—CH_2—$ may be replaced by —CH═CH— or —C≡C—, and in the groups, at least one of hydrogen may be replaced by fluorine or chlorine;

a1 and a2 are independently 0, 1, 2, 3 or 4, and a sum of a1 and a2 is 4;

ring $A^1$ is naphthalene, anthracene or phenanthrene, ring $A^2$ is phenyl, naphthyl, anthracenyl or phenanthrenyl, and in the rings, at least one of hydrogen may be replaced by fluorine, chlorine, alkyl having 1 to 5 carbons, alkyl having 1 to 5 carbons in which at least one of hydrogen is replaced by fluorine or alkyl having 1 to 5 carbons in which at least one of hydrogen is replaced by chlorine;

$Z^1$ is a single bond, —CO—, —COO—, —OCO—, —CH═CH—, —C≡C—, —CH═CH—COO—, —OCO—CH═CH—, —CO—CH═CH—, —CH═CH—CO—, $—CH═CH—CH_2O—$, $—OCH_2—CH═CH—$, $—CH═CH—OCH_2—$ or $—OH_2O—CH═CH—$; and b1 is 0, 1, and 2 or 3.

Item 3. The compound according to item 1, wherein, in formula (1), all of a1 moieties of $P^1$ and a2 moieties of $P^2$ are identically $—OCO—HC═CH_2$ or $—OCO—(CH_3)C═CH_2$;

$S^1$ and $S^2$ are independently a single bond, —COO—, —OCO—, $—CH_2—$, $—CH_2O—$, $—OCH_2—$, $—(CH_2)_2—$, $—(CH_2)_2—O—$, $—O—(CH_2)_2—$, —CH═CH—, —CH═CH—O—, —O—CH═CH—, —C≡C—, —C≡C—O—, —O—C≡C—, $—(CH_2)_3—$, $—(CH_2)_3—O—$, $—O—(CH_2)_3—$, $—(CH_2)_4—$, $—(CH_2)_4—O—$ and $—O—(CH_2)_4—$;

a1 and a2 are independently 0, 1, 2, 3 or 4, and a sum of a1 and a2 is 4;

ring $A_1$ is naphthalene, anthracene or phenanthrene, ring $A^2$ is phenyl, and in the rings, at least one of hydrogen may be replaced by fluorine, chlorine, $—CH_3$, $—CHF_2$ or $—CF_3$;

$Z^1$ is a single bond, —CH═CH—, —CH═CH—COO—, —OCO—CH═CH—, $—CH═CH—CH_2O—$, $—OCH_2—CH═CH—$, $—CH═CH—OCH_2—$ or $—CH_2O—CH═CH—$; and b1 is 0, 1 or 2.

Item 4. The compound according to item 1, represented by any one of formulas (1-1) to (1-13):

(1-1)

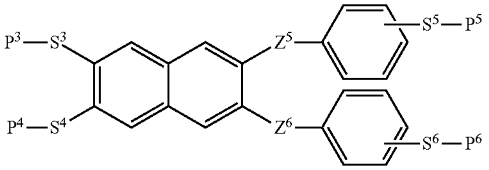

-continued (1-2)

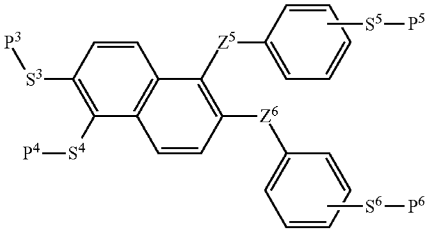

(1-3)

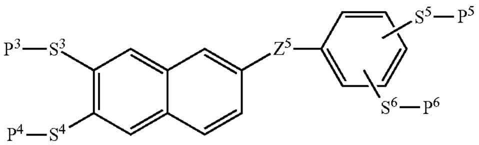

(1-4)

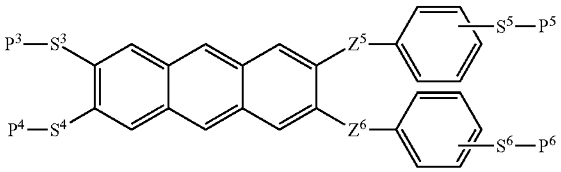

(1-5)

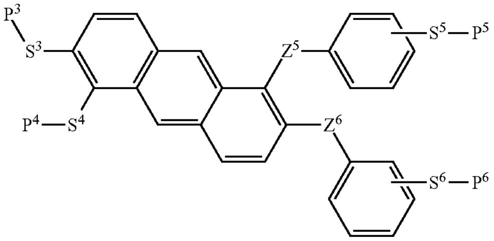

(1-6)

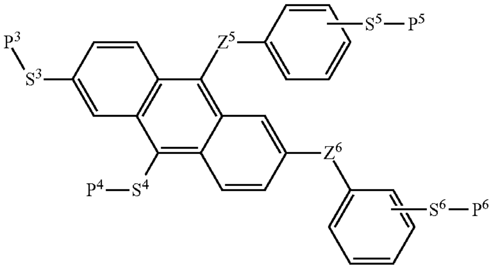

(1-7)

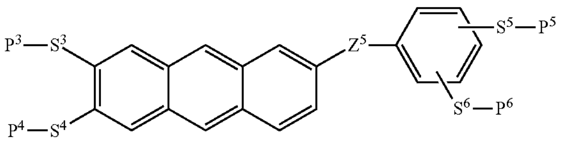

(1-8)

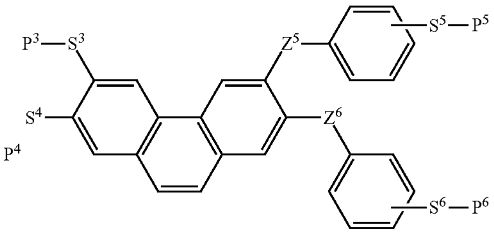

-continued (1-9)

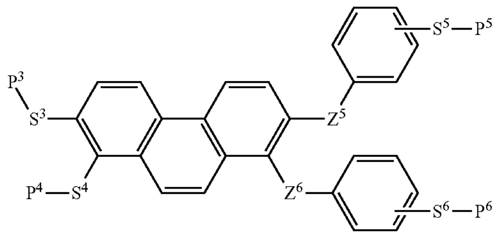

(1-10)

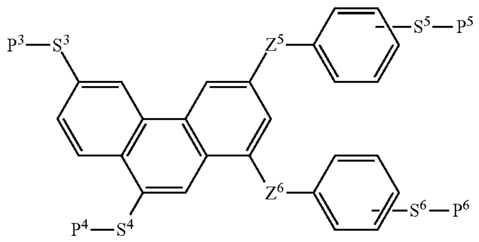

(1-11)

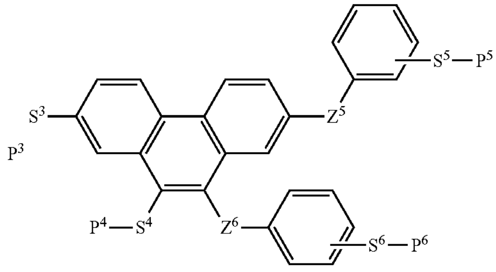

(1-12)

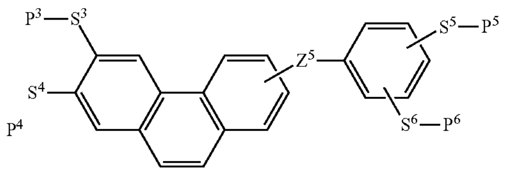

(1-13)

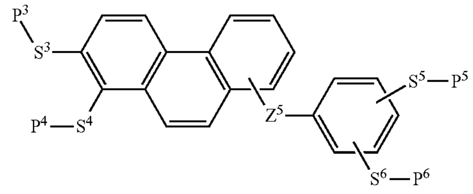

wherein, in formulas (1-1) to (1-13), all of $P^3$, $P^4$, $P^5$ and $P^6$ are identically a group represented by formula (P-1), and in formula (P-1), M is hydrogen, fluorine, $—CH_3$ or $—CF_3$;

(P-1)

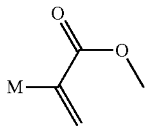

$S^3$, $S^4$, $S^5$ and $S^6$ are independently a single bond or alkylene having 1 to 6 carbons, and in the alkylene, at least one of $—CH_2—$ may be replaced by —O—, —COO— or —OCO—, at least one of $—CH_2—CH_2—$ may be replaced by —CH═CH— or —C≡C—, and in the groups, at least one of hydrogen may be replaced by fluorine or chlorine; and $Z^5$ and $Z^6$ are independently a single bond, —CO—, —COO—, —OCO—, —CH═CH—, —C≡C—, —CH═CH—COO—, —OCO—CH═CH—, —OCO—C($CH_3$)═CH—, —CO—CH═CH—, —CH═CH—CO—, —CH═CH—$CH_2$O—, —$OCH_2$—CH═CH—, —CH═CH—$OCH_2$— or —$CH_2$O—CH═CH—.

Item 5. The compound according to item 4, wherein, in formulas (1-1) to (1-13), all of $P^3$, $P^4$, $P^5$ and $P^6$ are —OCO—HC═$CH_2$ or —OCO—($CH_3$)C═$CH_2$; $S^3$, $S^4$, $S^5$ and $S^6$ are a single bond; and $Z^5$ and $Z^6$ are a single bond.

Item 6. The compound according to item 1, represented by any one of formulas (1-14) to (1-22):

(1-14)

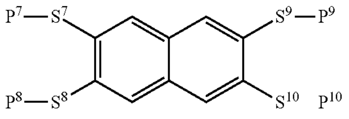

(1-15)

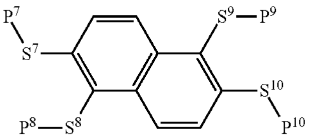

(1-16)

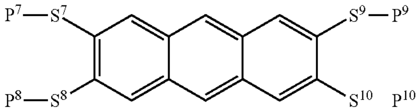

(1-17)

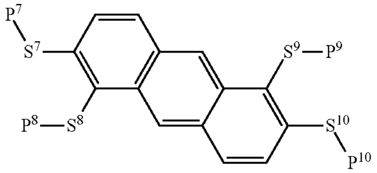

(1-18)

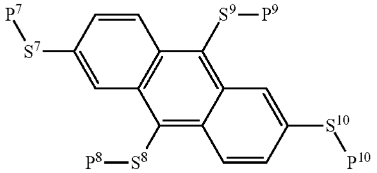

(1-19)

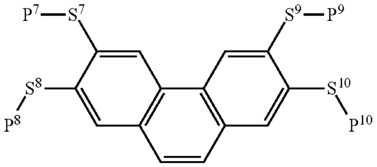

(1-20)

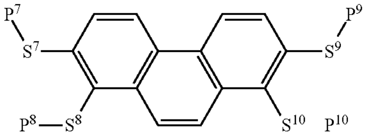

-continued (1-21)

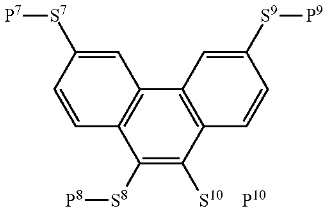

(1-22)

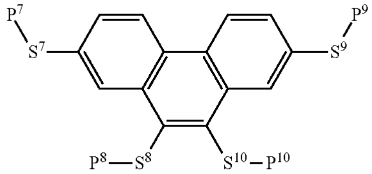

wherein, in formulas (1-14) to (1-22), all of $P^7$, $P^8$, $P^9$ and $P^{10}$ are identically a group represented by formula (P-1), and in formula (P-1), M is hydrogen, fluorine, —$CH_3$ or —$CF_3$:

(P-1)

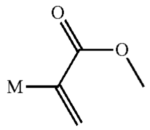

$S^7$, $S^8$, $S^9$ and $S^{10}$ are independently a single bond or alkylene having 1 to 6 carbons, and in the alkylene, at least one of —$CH_2$— may be replaced by —O—, —COO— or —OCO—, at least one of —$CH_2$—$CH_2$— may be replaced by —CH═CH— or —C≡C—, and in the groups, at least one of hydrogen may be replaced by fluorine or chlorine.

Item 7. The compound according to item 6, wherein, in formulas (1-14) to (1-22), all of $P^7$, $P^8$, $P^9$ and $P^{10}$ are —OCO—HC═$CH_2$ or —OCO—($CH_3$)C═$CH_2$; and $S^7$, $S^8$, $S^9$ and $S^{10}$ are a single bond.

Item 8. The compound according to item 1, represented by formula (1-3-1), (1-14-1) or (1-19-1):

(1-3-1)

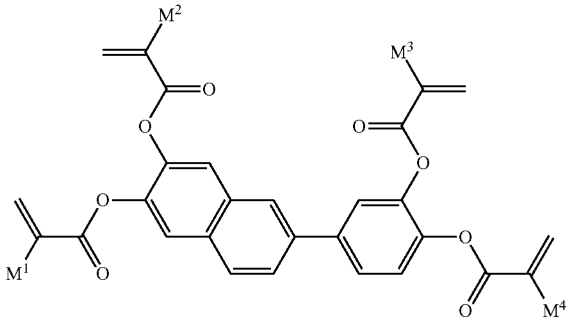

-continued (1-14-1)

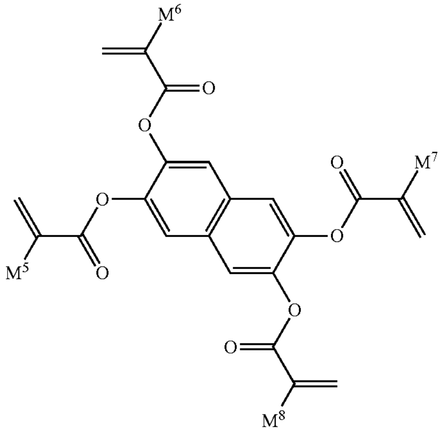

(1-19-1)

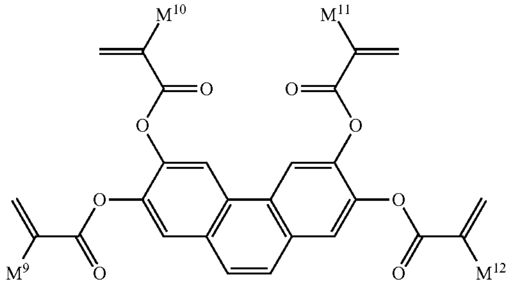

wherein, in formula (1-3-1), (1-14-1) or (1-19-1), all of $M^1$ to $M^{12}$ are identically hydrogen, fluorine, $-CH_3$ or $-CF_3$.

Item 9. A polymer, obtained from the compound according to any one of items 1 to 8.

Item 10. A liquid crystal composition, containing at least one selected from the group of the compound according to any one of items 1 to 8 and the polymer according to item 9.

Item 11. The liquid crystal composition according to item 10, further containing at least one compound selected from the group of compounds represented by formulas (2) to (4):

(2)

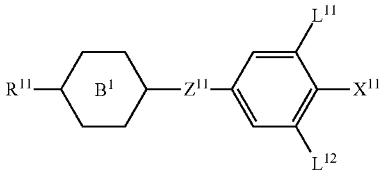

(3)

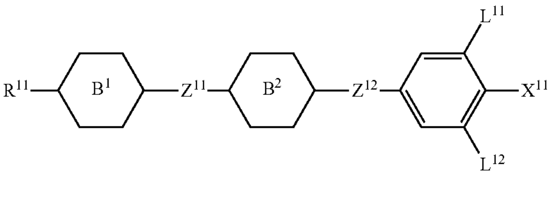

-continued (4)

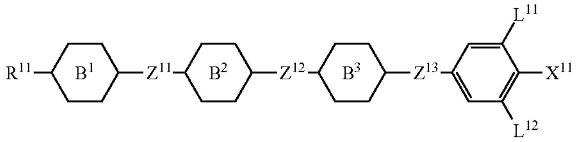

wherein, in formulas (2) to (4), $R^{11}$ is alkyl having 1 to 10 carbons or alkenyl having 2 to 10 carbons, and in the alkyl and the alkenyl, at least one of hydrogen may be replaced by fluorine, and at least one of $-CH_2-$ may be replaced by $-O-$;

$X^{11}$ is fluorine, chlorine, $-OCF_3$, $-OCHF_2$, $-CF_3$, $-CHF_2$, $-CH_2F$, $-OCF_2CHF_2$ or $-OCF_2CHFCF_3$;

ring $B^1$, ring $B^2$ and ring $B^3$ are independently 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{11}$, $Z^{12}$ and $Z^{13}$ are independently a single bond, $-CH_2CH_2-$, $-CH{=}CH-$, $-C{\equiv}C-$, $-COO-$, $-CF_2O-$, $-OCF_2-$, $-CH_2O-$ or $-(CH_2)_4-$; and $L^{11}$ and $L^{12}$ are independently hydrogen or fluorine.

Item 12. The liquid crystal composition according to items 10 or 11, further containing at least one compound selected from the group of compounds represented by formula (5):

(5)

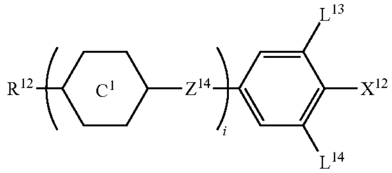

wherein, in formula (5), $R^{12}$ is alkyl having 1 to 10 carbons or alkenyl having 2 to 10 carbons, and in the alkyl and the alkenyl, at least one of hydrogen may be replaced by fluorine, and at least one of $-CH_2-$ may be replaced by $-O-$;

$X^{12}$ is $-C{\equiv}N$ or $-C{\equiv}C-C{\equiv}N$;

ring $C^1$ is 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{14}$ is a single bond, $-CH_2CH_2-$, $-C{\equiv}C-$, $-COO-$, $-CF_2O-$, $-OCF_2-$ or $-CH_2O-$;

$L^{13}$ and $L^{14}$ are independently hydrogen or fluorine; and i is 1, 2, 3 or 4.

Item 13. The liquid crystal composition according to any one of items 10 to 12, further containing at least one compound selected from the group of compounds represented by formulas (6) to (12):

(6)

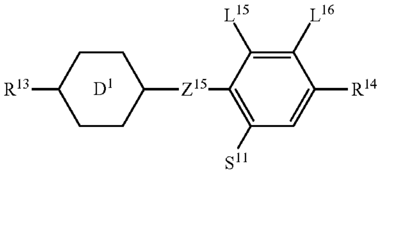

(7)

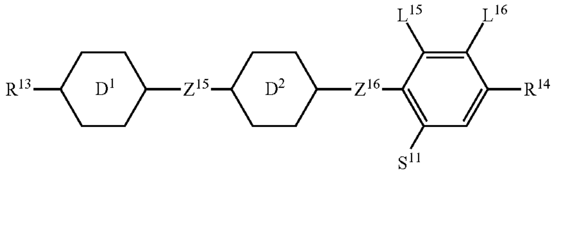

-continued (8)

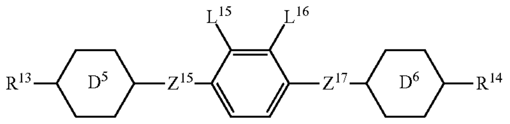

(9)

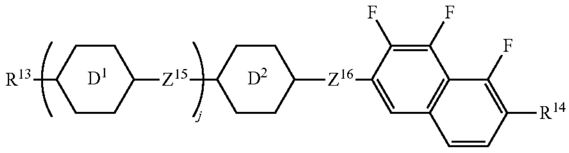

(10)

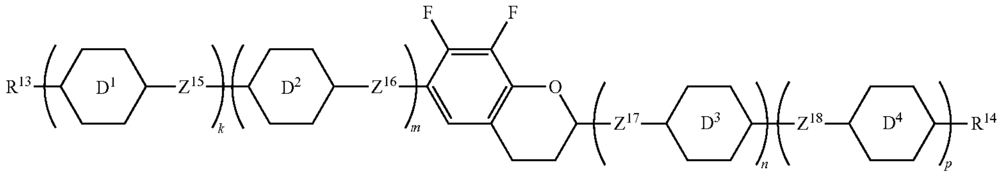

(11)

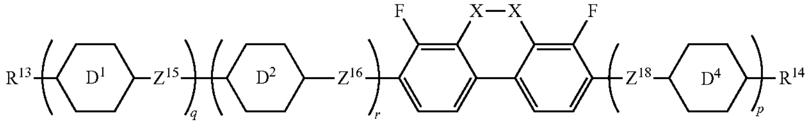

(12)

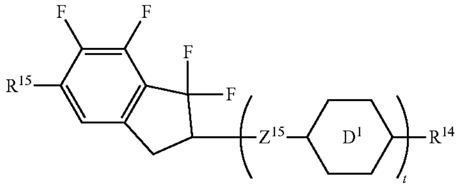

wherein, in formulas (6) to (12), $R^{13}$ and $R^{14}$ are independently alkyl having 1 to 10 carbons or alkenyl having 2 to 10 carbons, and in the alkyl and the alkenyl, at least one of $—CH_2—$ may be replaced by —O—, and at least one of hydrogen may be replaced by fluorine;

$R^{15}$ is hydrogen, fluorine, alkyl having 1 to 10 carbons or alkenyl having 2 to 10 carbons, and in the alkyl and the alkenyl, at least one of $—CH_2—$ may be replaced by —O—, and at least one of hydrogen may be replaced by fluorine;

$S^{11}$ is hydrogen or methyl;

X is $—CF_2—$, —O— or —CHF—;

ring $D^1$, ring $D^2$, ring $D^3$ and ring $D^4$ are independently 1,4-cyclohexylene, 1,4-cyclohexenylene, 1,4-phenylene in which at least one of hydrogen may be replaced by fluorine, tetrahydropyran-2,5-diyl or decahydronaphthalene-2,6-diyl;

ring $D^5$ and ring $D^6$ are independently 1,4-cyclohexylene, 1,4-cyclohexenylene, 1,4-phenylene, tetrahydropyran-2,5-diyl or decahydronaphthalene-2,6-diyl;

$Z^{15}$, $Z^{16}$, $Z^{17}$ and $Z^{18}$ are independently a single bond, $—CH_2CH_2—$, —COO—, $—CH_2O—$, $—OCF_2—$ or $—OCF_2CH_2CH_2—$;

$L^{15}$ and $L^{16}$ are independently fluorine or chlorine; and j, k, m, n, p, q, r and s are independently 0 or 1, a sum of k, m, n and p is 1 or 2, a sum of q, r and s is 0, 1, 2 or 3, and t is 1, 2 or 3.

Item 14. The liquid crystal composition according to any one of items 10 to 13, further containing at least one compound selected from the group of compounds represented by formulas (13) to (15):

(13)

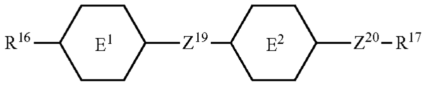

-continued (14)

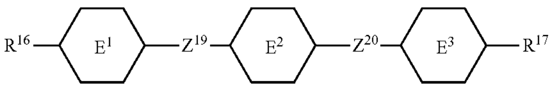

(15)

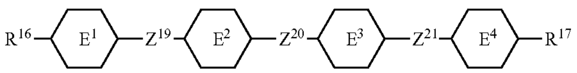

wherein, in formulas (13) to (15), $R^{16}$ and $R^{17}$ are independently alkyl having 1 to 10 carbons or alkenyl having 2 to 10 carbons, and in the alkyl or the alkenyl, at least one of $—CH_2—$ may be replaced by —O—, and at least one of hydrogen may be replaced by fluorine;

ring $E^1$, ring $E^2$, ring $E^3$ and ring $E^4$ are independently 1,4-cyclohexylene, 1,4-phenylene, 2-fluoro-1,4-phenylene, 2,5-difluoro-1,4-phenylene or pyrimidine-2,5-diyl; and $Z^{19}$, $Z^{20}$, and $Z^{21}$ are independently a single bond, $—CH_2CH_2—$, —CH═CH—, —C≡C—or —COO—.

Item 15. The liquid crystal composition according to any one of items 10 to 14, further containing at least one of a polymerizable compound, an optically active compound, an antioxidant, an ultraviolet light absorber, a light stabilizer, a heat stabilizer, an antifoaming agent, a polymerization initiator and a polymerization inhibitor.

Item 16. A liquid crystal display device including the liquid crystal composition according to any one of items 10 to 15.

The invention further includes the following items: (a) the polymerizable composition, further containing at least one of additives such as the optically active compound, the antioxidant, the ultraviolet light absorber, the light stabilizer, the heat stabilizer, the antifoaming agent, the polymerization initiator and the polymerization inhibitor; (b) the polymerizable composition, further containing a polymerizable compound different from the polymerizable compound represented by formula (1); (c) an AM device including the polymerizable composition; (d) a device, including the polymerizable composition and having a PS-TN mode, a PS-IPS mode, a PS-FFS mode, a PSA-VA mode or a PSA-OCB mode; (e) a transmissive device including the polymerizable composition; (f) use of the polymerizable composition as a composition having a nematic phase; and (g) use as an optical activity composition by adding an optically active compound to the composition.

The invention still further includes the following items: (h) a polymerizable composition, containing at least one compound selected from the group of compounds represented by formula (1) and having positive dielectric anisotropy; (i) a polymerizable composition, containing at least one compound selected from the group of compounds represented by formula (1), and at least one compound selected from the group of compounds represented by formulas (2) to (4); (j) a polymerizable composition, containing at least one compound selected from the group of compounds represented by formula (1), and at least one compound selected from the group of compounds represented by formula (5); and (k) a polymerizable composition, containing at least one compound selected from the group of compounds represented by formula (1), at least one compound selected from the group of compounds represented by formulas (2) to (4), and at least one compound selected from the group of compounds represented by formula (5).

The invention still further includes the following items; (1) a polymerizable composition, containing at least one compound selected from the group of compounds represented by formula (1) and having negative dielectric anisotropy; (m) a polymerizable composition, containing at least one compound selected from the group of compounds represented by formula (1), and at least one compound selected from the group of compounds represented by formulas (6) to (12); (n) a polymerizable composition, containing at least one compound selected from the group of compounds represented by formula (1), at least one compound selected from the group of compounds represented by formulas (6) to (12), and at least one compound selected from the group of compounds represented by formulas (2) to (4); (o) a liquid crystal composite formed by polymerization of the polymerizable composition; and (p) use of the polymerizable composition or the liquid crystal composite in a liquid crystal display device having a PSA mode.

1. Polymerizable Compound

Polymerizable compound (1) of the invention will be first described, and then a synthesis method, a polymerizable composition, a liquid crystal composite and a liquid crystal display device will be described in the order. A first feature of compound (1) is in having a condensed ring such as naphthalene, anthracene and phenanthrene, and four polymerizable groups. One of the polymerizable groups may be bonded directly with the condensed ring or indirectly with the condensed ring through a divalent group such as phenylene and naphthalenediyl. A second feature of compound (1) is in having symmetry (or partial symmetry) of a molecule. A skeleton of the molecule is the condensed ring and the condensed ring has the symmetry. The symmetry of a whole molecule can be attained by directly or indirectly arranging the four polymerizable groups to the condensed ring in a well-balanced manner. A third feature of compound (1) is in the four polymerizable groups being identical. The feature can be contributed to the symmetry of the molecule, and therefore is excellent. In addition, "symmetry" means mirror symmetry or rotor symmetry.

When the molecule has the symmetry, compound (1) is expected to have advantages as described below. A first advantage is in ease of synthesis of the polymerizable compound. The advantage will be described by taking naphthalene as an example. Reactivity on 1-position and 8-position (peri-position) in naphthalene is equivalent because two positions are symmetrical. In a similar thought, reactivity on 2-position, 3-position, 6-position and 7-position (pros-position) in naphthalene are also equivalent. Accordingly, introduction of a plurality of functional groups into symmetrical positions in naphthalene is considered to be easier than introduction thereof into asymmetrical positions. Compound (1) is symmetrical, and therefor a synthesis thereof is presumed to be comparatively easy.

A second advantage is in a small decrease in an order parameter of a liquid crystal (degree of order of the liquid crystal) upon adding the compound to the liquid crystal composition. Compound (1) is added to the liquid crystal composition, and then polymerized to form a network of a polymer among the liquid crystal molecules. The polymer is utilized for control of the liquid crystal molecules in the PSA mode. The order parameter of the liquid crystal decreases upon adding the polymerizable compound to the liquid crystal composition. Compound (1) has the symmetry or partial symmetry of the molecule, and therefore is presumed to have a small decrease in the order parameter.

Compound (No. 1) includes a compound in which four polymerizable groups are identical according to the invention. Compound (III) includes a compound in which one of four polymerizable groups is not identical as disclosed in CN 102888231 A. The compounds are compared using a molecular model. As a result, compound (No. 1) is founded to be further highly elliptical in comparison with compound (III). Accordingly, compound (No. 1) is presumed to be difficult to decrease the order parameter upon being added to the rod like liquid crystal molecules.

Compound(No.1)

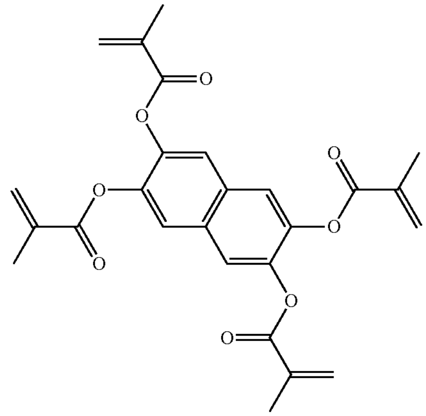 [SMILES: C=C(C)C(=O)Oc1cc2cc(OC(=O)C(=C)C)c(OC(=O)C(=C)C)cc2cc1OC(=O)C(=C)C]

Compound(III)

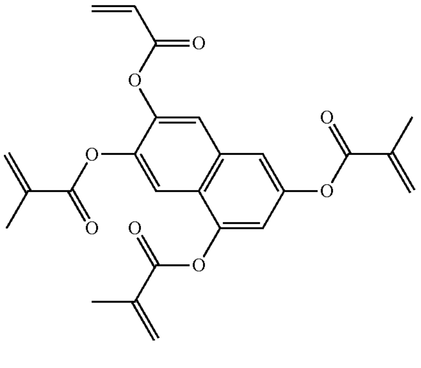

Preferred examples of compound (1) will be described.

(1)

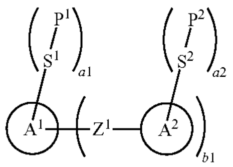

Preferred examples of polymerizable groups $P^1$ and $P^2$, connecting groups $S^1$ and $S^2$, ring $A^1$ and $A^2$ or bonding group $Z^1$ of compound (1) are also applied to a subordinate formula of compound (1). No significant difference exists in the physical properties of the compound, and therefore compound (1) may also include a higher amount of an isotope such as $^2H$ (deuterium) and $^{13}C$ than an amount of natural abundance.

In formula (1), $P^1$ and $P^2$ are a group selected from the groups represented by formulas (P-1), (P-2) and (P-3), and in formula (P-1), M is hydrogen, fluorine, $—CH_3$ or $—CF_3$.

(P-1)

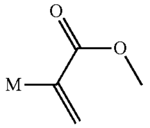

(P-2)

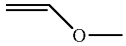

(P-3)

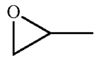

Further, all of a1 moieties of $P^1$ and a2 moieties of $P^2$ are identical.

Preferred examples of $P^1$ and $P^2$ include groups (P-1) and (P-2). Further preferred examples include group (P-1). In group (P-1), preferred M is hydrogen, fluorine or $—CH_3$. Further preferred M is hydrogen or $—CH_3$. Particularly preferred examples of $P^1$ and $P^2$ include acryloyloxy ($—OCO—HC{=}CH_2$) and methacryloyloxy ($—OCO—(CH_3)C{=}CH_2$). Particularly preferred examples include methacryloyloxy.

In formula (1), $S^1$ and $S^2$ are independently a single bond or alkylene having 1 to 6 carbons, and in the alkylene, at least one of $—CH_2—$ may be replaced by $—O—$, $—COO—$ or $—OCO—$, at least one of $—CH_2—CH_2—$ may be replaced by $—CH{=}CH—$ or $—C{\equiv}C—$, and in the groups, at least one of hydrogen may be replaced by halogen. Preferred examples of halogen include fluorine or chlorine. Further preferred examples include fluorine.

Preferred examples of $S^1$ or $S^2$ include a single bond, $—COO—$, $—OCO—$, $—CH_2—$, $—CH_2O—$, $—OCH_2—$, $—(CH_2)_2—$, $—(CH_2)_2—O—$, $—O—(CH_2)_2—CH{=}CH—$, $—CH{=}CH—O—$, $—O—CH{=}CH—$, $—C{\equiv}C—$, $—C{\equiv}C—O—$, $—O—C{\equiv}C—$, $—(CH_2)_3—$, $—(CH_2)_3—O—$, $—O—(CH_2)_3—$, $—(CH_2)_4—$, $—(CH_2)_4—O—$ and $—O—(CH_2)_4—$. Further preferred examples include a single bond, $—CH_2—$, $—(CH_2)_2—O—$, $—O—(CH_2)_2—$, $—CH{=}CH—$, $—CH{=}CH—O—$ and $—O—CH{=}CH—$. Most preferred examples include a single bond.

In formula (1), a1 and a2 are independently 0, 1, 2, 3 or 4, and a sum of a1 and a2 is 4.

Preferred combinations of a1 and a2 include a combination (a1=4, a2=0), a combination (a1=2, a2=2) or a combination (a1=0, a2=4). Further preferred combinations include a combination (a1=4, a2=0) or a combination (a1=2, a2=2). Particularly preferred combinations include a combination (a1=4, a2=0).

In formula (1), ring $A^1$ is naphthalene, anthracene or phenanthrene, and to exactly express the group, a group having (a1+b1) valence derived from the rings. Ring $A^2$ is cyclohexyl, phenyl, naphthyl, anthracenyl or phenanthrenyl, and in the rings, at least one of hydrogen may be replaced by halogen, alkyl having 1 to 10 carbons, or alkyl having 1 to 10 carbons in which at least one of hydrogen is replaced by halogen.

Preferred examples of halogen include fluorine or chlorine. Further preferred examples include fluorine. Preferred examples of alkyl in which at least one of hydrogen is replaced by halogen include fluoromethyl, difluoromethyl and trifluoromethyl.

Preferred examples of ring $A^1$ include naphthalene, anthracene, phenanthrene, 1-methylnaphthalene, 1-fluoronaphthalene, 1-trifluoromethylnaphthalene, 1-fluoroanthracene or phenanthrene. Further preferred examples include naphthalene, anthracene and phenanthrene. Preferred examples of ring $A^2$ include cyclohexyl, phenyl, naphthyl, anthracenyl, phenanthrenyl, 4-methylphenyl and 1-fluoro-2-naphthyl. Further preferred examples include phenyl, naphthyl, anthracenyl and phenanthrenyl.

In formula (1), $Z^1$ is a single bond, $—CO—$, $—COO—$, $—OCO—$, $—CH{=}CH—$, $—C{\equiv}C—$, $—CH{=}C(CH_3)—$, $—C(CH_3){=}CH—$, $—C(CH_3){=}C(CH_3)—$, $—CH{=}CH—COO—$, $—OCO—CH{=}CH—$, $—C(CH_3){=}CH—COO—$, $—OCO—CH{=}CH(CH_3)—$, $—CH{=}C(CH_3)—COO—$, $—OCO—C(CH_3){=}CH—$, $—C(CH_3){=}C(CH_3)—COO—$, $—OCO—C(CH_3){=}C(CH_3)—$, $—CH{=}CH—CO—$, $—CO—CH{=}CH—$, $—CH{=}CH—CH_2O—$, $—OCH_2—CH{=}CH—$, $—CH{=}CH—OCH_2—$ or $—CH_2O—CH{=}CH—$.

Preferred examples of $Z^1$ include a single bond, $—CO—$, $—COO—$, $—OCO—$, $—CH{=}CH—$, $—C{\equiv}C—$, $—C(CH_3){=}CH—$, $—CH{=}CH—COO—$, $—OCO—CH{=}CH—$, $—CH{=}CH—CO—$, $—CO—CH{=}CH—$, $—CH{=}CH—CH_2O—$, $—OCH_2—CH{=}CH—$, $—CH{=}CH—OCH_2—$ and $—CH_2O—CH{=}CH—$. Further preferred examples include a single bond or $—CH{=}CH—$. Most preferred examples include a single bond.

In formula (1), b1 is 0, 1, 2, 3 or 4. Preferred examples of b1 include 0, 2 and 4 from a viewpoint of the symmetry of the molecule. Further preferred examples include 0 and 2. Examples of compounds in which b1 is 0 include compounds (1-14) to (1-22). Examples of compounds in which b1 is 2 include compounds (1-1) to (1-13). Particularly preferred examples include 0.

In addition, a case where an element of $S^1$ to be bonded with $P^1$ is oxygen is not preferred because a divalent group such as $—COO—O—$ and $—O—O—$ is formed. The rule is also applied to a bond between $P^2$ and $S^2$, or the like.

Preferred examples of compound (1) include compounds (1-1) to (1-22) described in item 4 or item 5. From a viewpoint of the symmetry of the molecule, further preferred examples include compounds (1-1), (1-4), and (1-14) to (1-22). From a viewpoint of partial symmetry, preferred examples include compounds (1-2), (1-3), (1-5), (1-7), (1-9) and (1-13). Particularly preferred examples include compounds (1-14) to (1-22). Preferred specific compounds of compound (1) include compound (1-3-1), (1-14-1) or (1-19-1) described in item 8.

2. Synthesis Method

A synthesis method of compound (1) will be described. Compound (1) can be synthesized by suitably combining methods in synthetic organic chemistry. A method for introducing an objective polymerizable group P, connecting group S, ring A or bonding group Z into a starting material is described in books such as Houben-Wyle, Methoden der Organische Chemie (Georg-Thieme Verlag, Stuttgart), Organic Syntheses (John Wily & Sons, Inc.), Organic Reactions (John Wily & Sons, Inc.), Comprehensive Organic Synthesis (Pergamon Press) and New Experimental Chemistry Course (Shin Jikken Kagaku Koza in Japanese) (Maruzen Co., Ltd.).

2-1. Formation of Bonding Group Z

An example of a method for forming bonding group Z in compound (1) is as described in a scheme below. In the scheme, $MSG^1$ (or $MSG^2$) is a monovalent organic group having at least one ring. Monovalent organic groups represented by a plurality of $MSG^1$ (or $MSG^2$) may be identical or different. Compounds (1A) to (1R) correspond to compound (1). In formation of ester, a synthesis method of a compound having —COO— is shown. A compound having —OCO— can also be prepared by the synthesis method. Other asymmetrical bonding groups can also be formed in a similar manner.

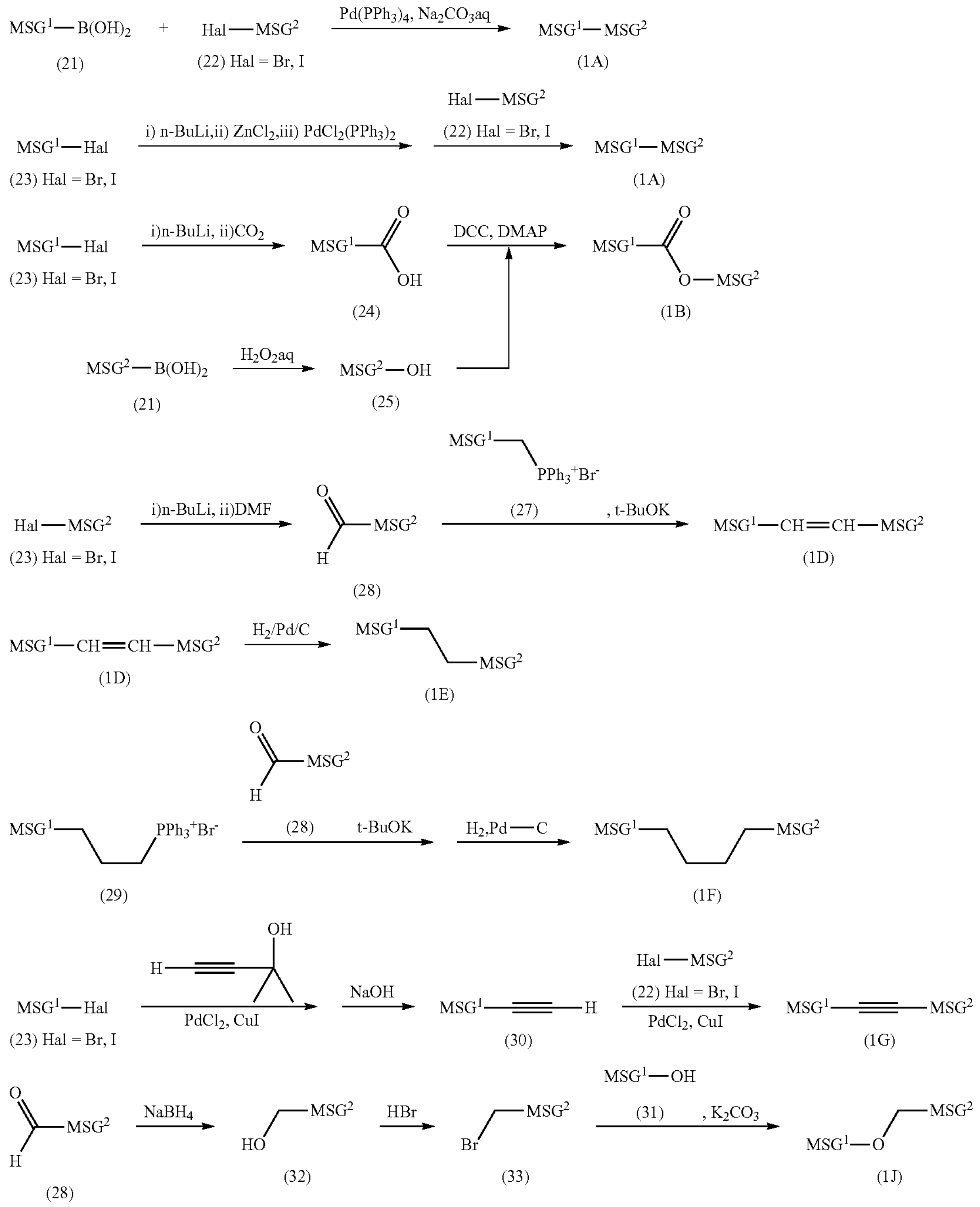

(21) (22) Hal = Br, I (1A)
(22) Hal = Br, I
(23) Hal = Br, I (1A)
(23) Hal = Br, I (24) (1B)
(21) (25)
(27)
(23) Hal = Br, I (28) (1D)
(1D) (1E)
(28)
(29) (1F)
(22) Hal = Br, I
(23) Hal = Br, I (30) (1G)
(31)
(28) (32) (33) (1J)

-continued

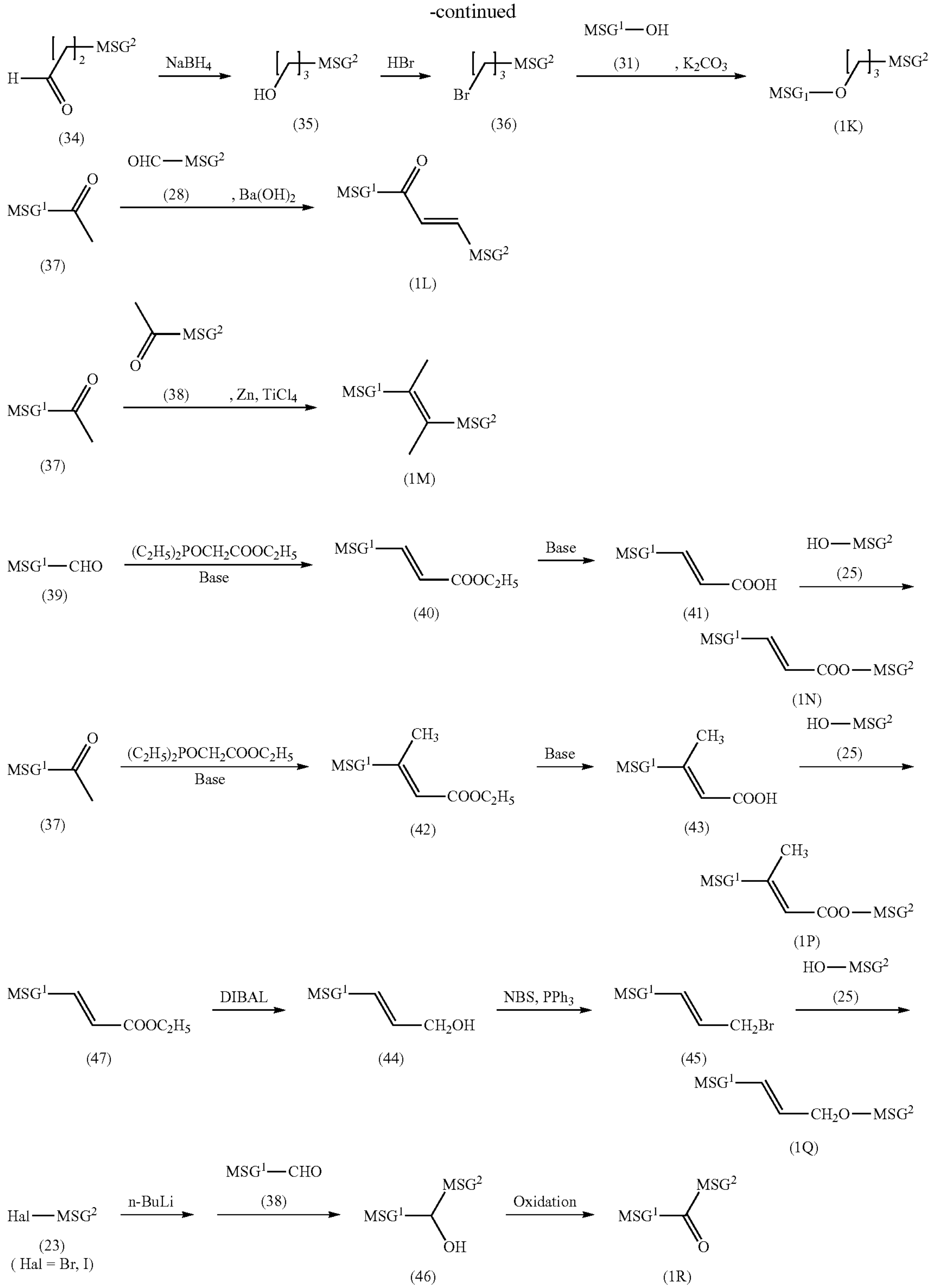

(1) Formation of a Single Bond

Compound (1A) is prepared by allowing arylboronic acid (21) to react, in the presence of a catalyst such as tetrakis (triphenylphosphine)palladium in an aqueous solution of carbonate, with compound (22) to be prepared according to a publicly known method. Compound (1A) is also prepared by allowing compound (23) to be prepared according to a publicly known method to react with n-butyllithium and subsequently with zinc chloride, and further with compound (22) in the presence of a catalyst such as dichlorobis(triphenylphosphine)palladium.

(2) Formation of —COO—

Carboxylic acid (24) is obtained by allowing compound (23) to react with n-butyllithium, and subsequently with carbon dioxide. Compound (1B) is prepared by allowing dehydrating condensation of, in the presence of 1,3-dicyclohexylcarbodiimide (DCC) and N,N-dimethyl-4-aminopyridine (DMAP), compound (24) and phenol (25) to be prepared according to a publicly known method.

(3) Formation of —CH═CH—

Aldehyde (28) is obtained by treating compound (23) with n-butyllithium and then allowing the treated compound to react with formamide such as N,N-dimethylformamide (DMF). Compound (1D) is prepared by allowing aldehyde (28) to react with phosphorus ylide generated by treating phosphonium salt (27) to be prepared according to a publicly known method with a base such as potassium tert-butoxide. Because a cis isomer is formed depending on reaction conditions, the cis isomer is isomerized into a trans isomer according to a publicly known method, when necessary.

(4) Formation of $—(CH_2)_2—$

Compound (1E) is prepared by hydrogenating compound (1D) in the presence of a catalyst such as palladium on carbon.

(5) Formation of $—(CH_2)_4—$

A compound having $—(CH_2)_2—CH═CH—$ is obtained by using phosphonium salt (29) in place of phosphonium salt (27) to perform reaction according to the method in section (III). Compound (1F) is prepared by catalytically hydrogenating the resulting product.

(6) Formation of —C≡C—

Compound (30) is obtained by allowing 2-methyl-3-butyn-2-ol to react with compound (23) in the presence of a catalyst including dichloropalladium and copper halide, and then deprotecting the resulting product under basic conditions. Compound (1G) is prepared by allowing compound (30) to react with compound (22) in the presence of a catalyst including dichloropalladium and copper halide.

(7) Formation of $—CH_2O—$

Compound (32) is obtained by reducing compound (28) with a reducing agent such as sodium borohydride. Compound (33) is obtained by halogenating the resulting product with hydrobromic acid or the like. Compound (1J) is prepared by allowing compound (33) to react with compound (31) in the presence of potassium carbonate or the like.

(8) Formation of $—(CH_2)_3—O—$

Compound (1K) is prepared by using compound (34) in place of compound (28) and according to the method in section (VII).

(9) Formation of —COCH═CH—

Compound (1L) is prepared by allowing compound (37) to react with compound (28) in the presence of barium hydroxide.

(10) Formation of $—C(CH_3)═C(CH_3)—$

Compound (1M) is prepared by allowing compound (37) to react with compound (38) in the presence of zinc and titanium tetrachloride.

(11) Formation of —CH═CH—COO—

Phosphorus ylide is prepared by allowing a base such as sodium hydride to act on ethyl diethylphosphoacetate, and ester (40) is obtained by allowing the phosphorus ylide to react with aldehyde (39). Carboxylic acid (41) is obtained by hydrolyzing ester (40) in the presence of a base such as sodium hydroxide. Compound (1N) is prepared by allowing dehydrating condensation of the compound and alcohol (25).

(12) Formation of $—C(CH_3)═CH—COO—$

Phosphorus ylide is prepared by allowing a base such as sodium hydride to act on ethyl diethylphosphoacetate, and ester (42) is obtained by allowing the phosphorus ylide to react with methyl ketone (37). Carboxylic acid (43) is obtained by hydrolyzing ester (42) in the presence of a base such as sodium hydroxide. Compound (IP) is prepared by allowing dehydrating condensation of the compound and alcohol (25)

(13) Formation of $—CH═CH—CH_2O—$

Alcohol (44) is obtained by reducing ester (47) with diisobutylaluminum hydride (DIBAL). Bromide (45) is obtained by a reaction of alcohol (44) with N-bromosuccinimide (NBS) in the presence of triphenylphosphine. Compound (1Q) is obtained by allowing dehydrating condensation of the compound and alcohol (25).

(14) Formation of —CO—

Alcohol (46) is obtained by allowing compound (23) to react with n-butyllithium, and subsequently with aldehyde (38). Compound (1R) is prepared by allowing alcohol (46) to react with an oxidizing agent such as a Jones reagent.

2-2. Formation of Polymerizable Group P

An example of a method for forming a polymerizable group described below is as described in a scheme below. In the scheme, $MSG^1$ is a monovalent organic group having at least one ring. Compounds (1S) to (1X) correspond to compound (1).

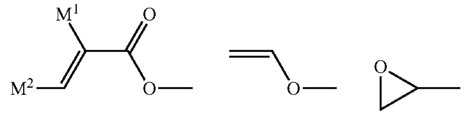

(M1, M2 = H, Me, F, $CF_3$)

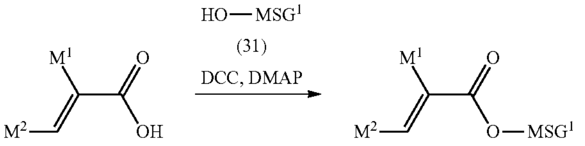

(51) (1S)

(M1, M2 = H, Me, F, $CF_3$)

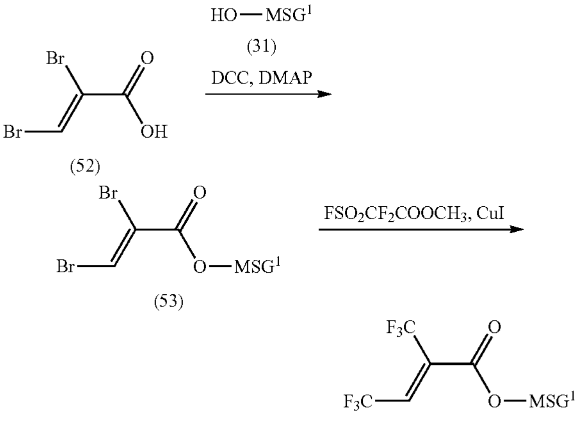

(52)

(53)

(1T)

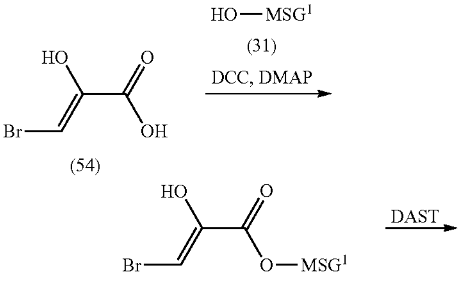

(54)

(55)

-continued

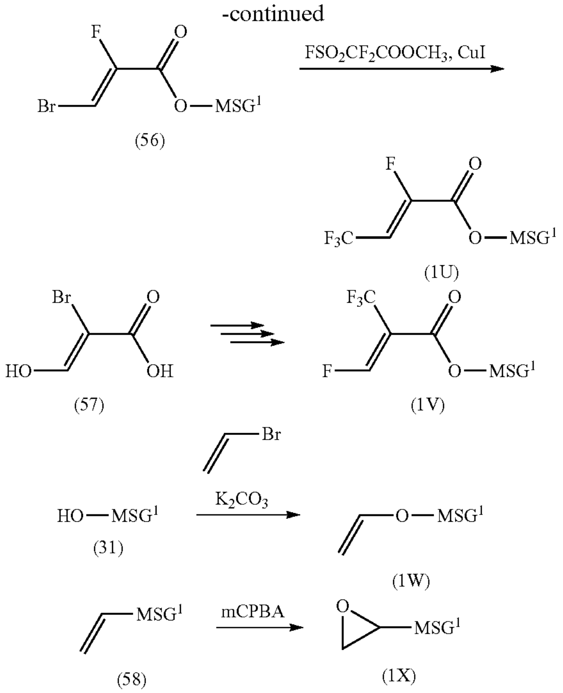

(56) (1U) (57) (1V) (31) (1W) (58) (1X)

(1) Formation of $M^2CH{=}CM^1$-COO—

When neither $M^1$ nor $M^2$ is —$CF_3$, when $M^1$ is fluorine and $M^2$ is not —$CF_3$, or when $M^1$ is —$CF_3$ and $M^2$ is not fluorine, carboxylic acid (51) shown in the scheme above is commercially available. Compound (1S) is prepared by allowing dehydrating condensation of carboxylic acid (51) and compound (31) in the presence of DCC and DMAP.

When both $M^1$ and $M^2$ are —$CF_3$, compound (53) is obtained by allowing dehydrating condensation of carboxylic acid (52) and compound (31) in the presence of DCC and DMAP. Compound (1T) is prepared by allowing compound (53) to react with methyl 2,2-difluoro-2-(fluorosulfonyl)acetate in the presence of an catalyst amount of copper iodide.

When $M^1$ is fluorine and $M^2$ is —$CF_3$, compound (55) is obtained by allowing dehydrating condensation of carboxylic acid (54) and compound (31) in the presence of DCC and DMAP. Compound (56) is obtained by fluorinating compound (55) with a fluorinating agent such as DAST. Compound (1U) is prepared by allowing compound (56) to react with methyl 2,2-difluoro-2-(fluorosulfonyl)acetate in the presence of a catalyst amount of copper iodide.

When $M^1$ is —$CF_3$ and $M^2$ is fluorine, compound (1V) is prepared using carboxylic acid (57) as a starting material and according to the method described above.

(2) Formation of a Vinyloxy Group

Compound (1W) is prepared by allowing compound (31) to react with vinyl bromide in the presence of potassium carbonate or the like.

(3) Formation of an Epoxy Group

Compound (1X) is prepared by oxidizing, with meta-chloroperbenzoic acid (mCPBA) or the like, vinyl compound (58) to be prepared according to a publicly known method.

2-3. Formation of Connecting Group S

An example of a method for forming connecting group S in compound (1) is as described in a scheme below. In the scheme, $MSG^1$ is a monovalent organic group having at least one ring. Compound (1Y) corresponds to compound (1).

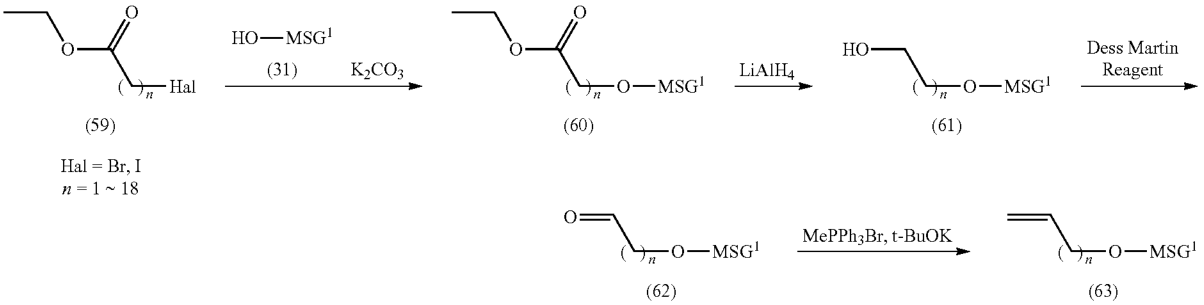

(59) (60) (61)

Hal = Br, I $n$ = 1 ~ 18

(62) (63)

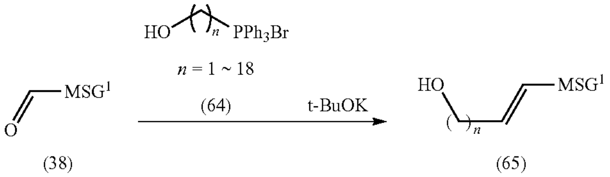

(38) (65)

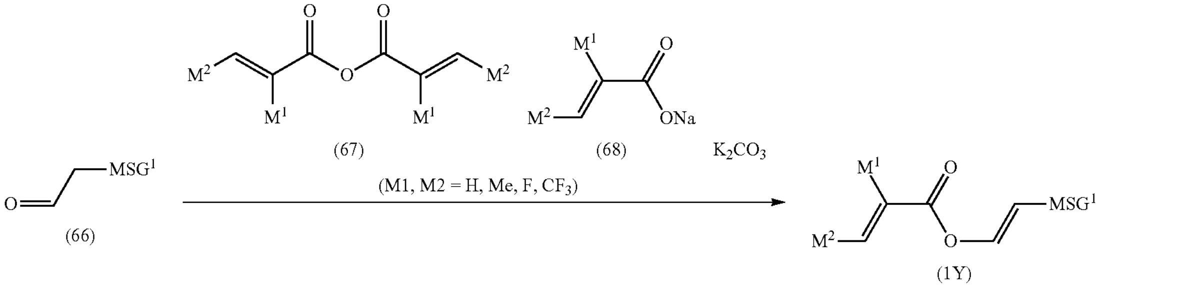

(67) (68) (66) (1Y)

-continued

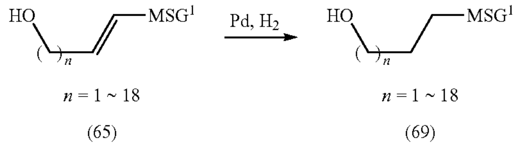

(1) Formation of —$CH_2O$—

Compound (60) is obtained by allowing compound (59) to be prepared according to a publicly known method to react with compound (31) in the presence of potassium carbonate or the like. Compound (61) is obtained by reducing compound (60) with a reducing agent such as lithium hydride aluminum or the like. Aldehyde (62) is obtained by oxidizing compound (61) with an oxidizing agent such as a Dess-Martin reagent or the like. Compound (63) is obtained by allowing phosphorus ylide generated by treating methyltriphenylphosphonium bromide with a base such as potassium tert-butoxide or the like to react with aldehyde (62).

When $M^2CH{=}CM^1$-COO— is introduced into compound (61), dehydrating condensation of compound (61) and compound (51) is performed according to the method describe above. When a vinyloxy group is introduced into compound (61), a reaction of compound (61) and vinyl bromide is performed according to the method described above. When an epoxy group is introduced into compound (63), an epoxidation reaction of compound (63) is performed according to the method described above.

(2) Formation of —CH═CH—

Compound (65) is obtained by allowing phosphorus ylide generated by treating phosphonium salt (64) to be prepared according to a publicly known method with a base such as potassium tert-butoxide to react with aldehyde (38). When $M^2CH{=}CM^1$-COO— is introduced into compound (65), dehydrating condensation of compound (65) and compound (51) is performed according to the method describe above. When a vinyloxy group is introduced into compound (65), a reaction of compound (65) and vinyl bromide is performed according to the method described above. When an epoxy group is introduced into compound (65), —$CH_2OH$ is converted into —CH═$CH_2$, and then an epoxidation reaction is performed according to the method described above.

$M^2CH{=}CM^1$-COO— may be introduced by a method described below. Compound (1Y) is prepared by allowing aldehyde (66) to be prepared according to a publicly known method to react with acid anhydride (67) and sodium carboxylate (68) in the presence of potassium carbonate or the like.

(3) Formation of —$CH_2CH_2$—

Compound (69) is prepared by hydrogenating compound (65) in the presence of a catalyst such as palladium on carbon. A method for introducing $M^2CH{=}CM^1$-COO—, a vinyloxy group or an epoxy group into alcohol is as described above.

2-4. Formation of Ring A

Ring $A^1$ is naphthalene, anthracene or the like, and ring $A^2$ is cyclohexyl, phenyl, naphthyl or the like. A hydroxy derivative of a compound such as naphthalene and anthracene to be required as a starting material upon preparing compound (1) is commercially available. A monovalent group such as cyclohexyl, phenyl and naphthyl can be utilized for a synthesis by selecting a hydroxy compound as a starting material.

3. Polymerizable Composition

A polymerizable composition contains at least one of compound (1) as a first component. A component of the composition may include only the first component. The composition may also contain a second component, a third component or the like. A kind of the second component or the like depends on a kind or application of an objective polymer. The polymerizable composition may further contain any other polymerizable compound different from compound (1) as the second component. Preferred examples of other polymerizable compounds include acrylate, methacrylate, a vinyl compound, a vinyloxy compound, propenyl ether, ethylene oxide (oxirane, oxetane) and vinyl ketone. Further preferred examples include a compound having at least one of acryloyloxy or a compound having at least one of methacryloyloxy. Still further preferred examples include a compound having acryloyloxy and methacryloyloxy.

Additional examples of other polymerizable compounds include compounds (M-1) to (M-12). In compounds (M-1) to (M-12), $R^{25}$, $R^{26}$ and $R^{27}$ are independently hydrogen or methyl; u, x and y are independently 0 or 1; v and w are independently an integer from 1 to 10; and $L^{21}$, $L^{22}$, $L^{23}$, $L^{24}$, $L^{25}$ and $L^{26}$ are independently hydrogen or fluorine.

(M-1)

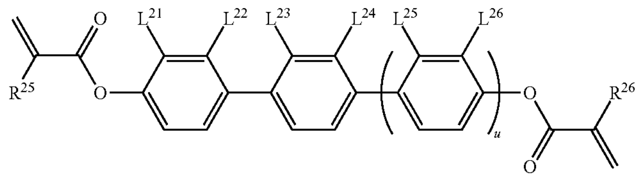

(M-2)

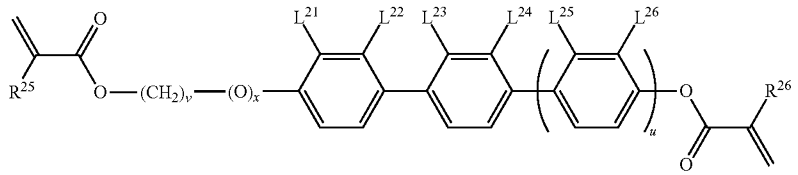

-continued
(M-3)
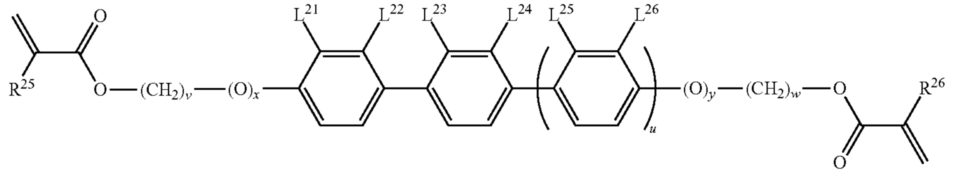
(M-4)
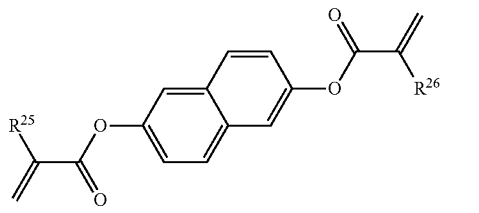
(M-5)
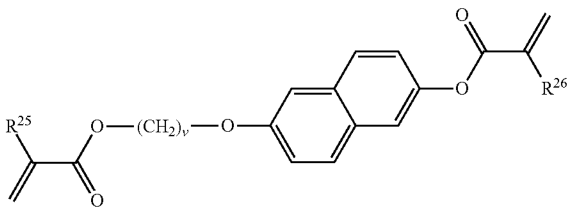
(M-6)
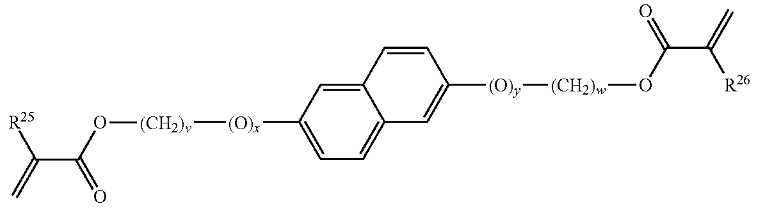
(M-7)
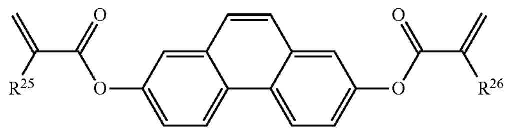
(M-8)
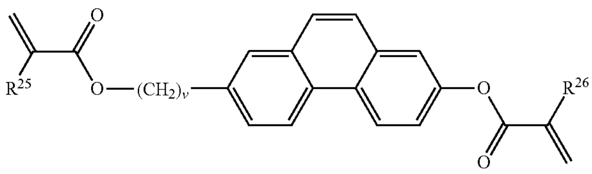
(M-9)
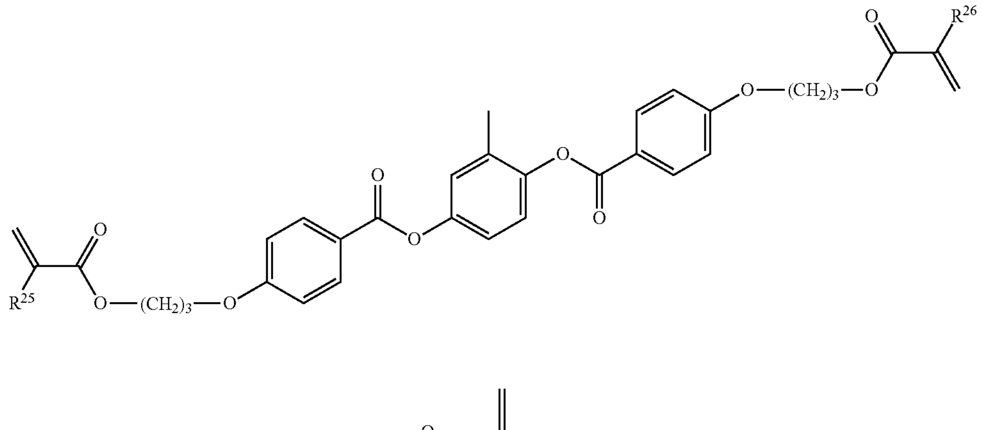
(M-10)
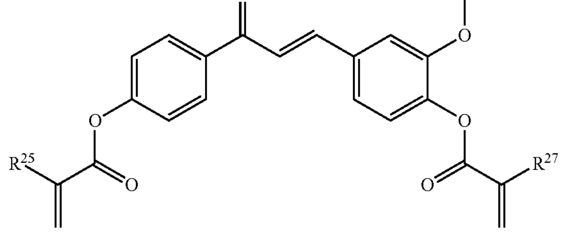

-continued (M-11)

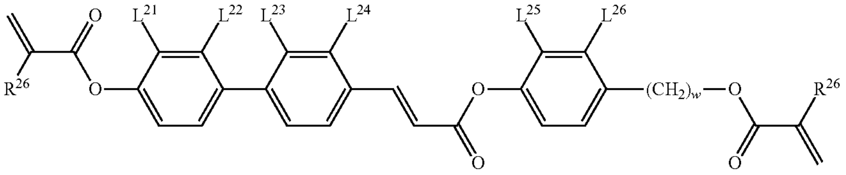

(M-12)

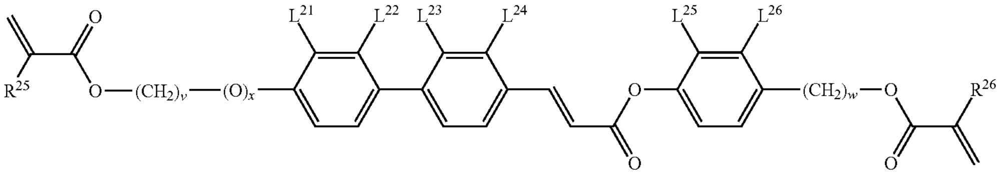

When a second component of the polymerizable composition is a polymerizable compound having a liquid crystal phase, an optical isotropic body is formed by allowing polymerization while controlling alignment of liquid crystal molecules. The optical isotropic body can be used for a phase difference film, a polarized light device, a circularly polarized light device, an elliptically polarized light device, an antireflection film, a selective reflection film, a color compensation film, a viewing angle compensation film or the like. An additive such as a polymerization initiator may be added to the polymerizable composition for the purpose of adjusting physical properties of the optical isotropic body.

The polymerizable composition may also contain a liquid crystal composition as the second component. When a liquid crystal display device having a mode such as PS-TN, PS-IPS, PS-FFS, PSA-VA and PSA-OCB is targeted, the polymerizable composition contains compound (1) as component A, and preferably, further contains a compound selected from components B, C, D and E shown below. Component B includes compounds (2) to (4). Component C includes compound (5). Component D includes compounds (6) to (12). Component E includes compounds (13) to (15). Upon preparing such a polymerizable composition, components B, C, D and E are preferably selected in taking positive or negative dielectric anisotropy, magnitude of dielectric anisotropy, or the like into consideration. The polymerizable composition prepared by properly selecting the component has a high maximum temperature, a low minimum temperature, small viscosity, suitable (namely, large or small) optical anisotropy, large positive or negative dielectric anisotropy and a suitable (namely, large or small) elastic constant.

The polymerizable composition is prepared by adding compound (1) to the liquid crystal composition. In such a polymerizable composition, an amount of addition of compound (1), namely, compound A is in the range from approximately 0.05% by weight to approximately 20% by weight based on the liquid crystal composition. A further preferred amount of addition is in the range from approximately 0.1% by weight to approximately 10% by weight. A still further preferred amount of addition is in the range from approximately 0.2% by weight to approximately 1% by weight. At least one of other polymerizable compounds different from compound (1) may be further added thereto. In the above case, an amount of addition of compound (1) and any other polymerizable compound in total is preferably within the range described above. Physical properties of the polymer to be formed can be adjusted by properly selecting any other polymerizable compound. Examples of other polymerizable compounds include acrylate and methacrylate, as previously described. The examples also include compounds (M-1) to (M-12).

Component B includes a compound having a halogen-containing or fluorine-containing group at a right terminal. Specific preferred examples of component B include compounds (2-1) to (2-16), compounds (3-1) to (3-113) and compounds (4-1) to (4-57). In the compounds of component B, $R^{11}$ and $X^{11}$ are defined in a manner identical with the definitions in item 11.

(2-1)

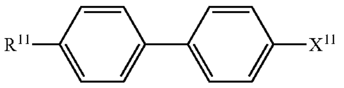

(2-2)

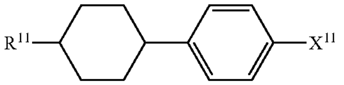

(2-3)

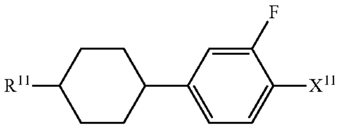

(2-4)

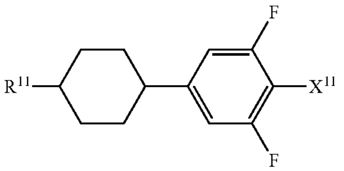

(2-5)

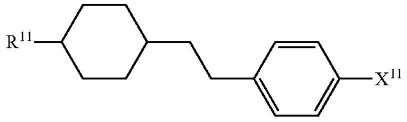

(2-6)

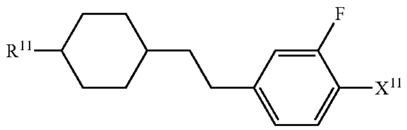

-continued
(2-7)
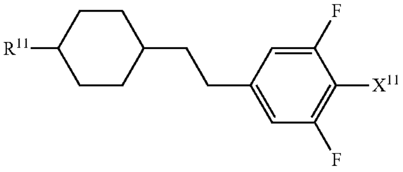
(2-8)
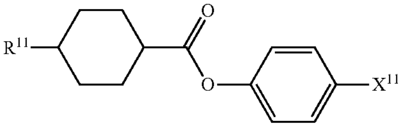
(2-9)
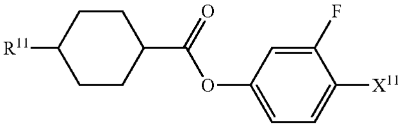
(2-10)
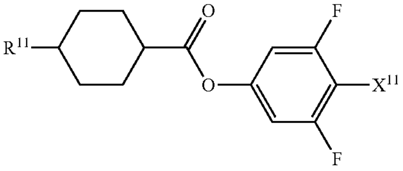
(2-11)
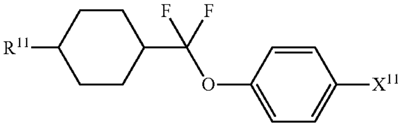
(2-12)
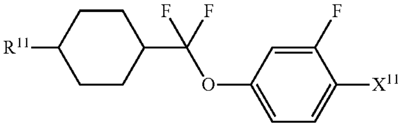
(2-13)
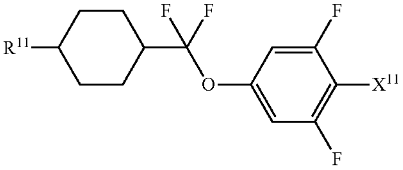
(2-14)
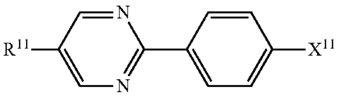
(2-15)
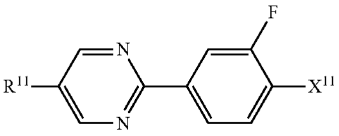
(2-16)
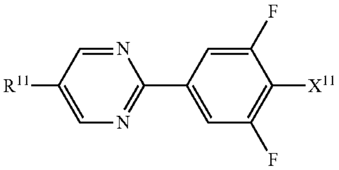
(3-1)
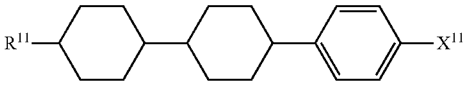
-continued
(3-2)
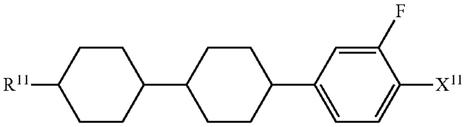
(3-3)
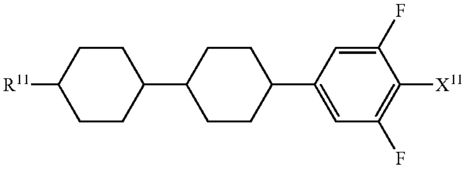
(3-4)
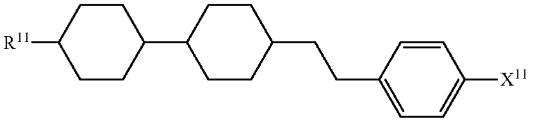
(3-5)
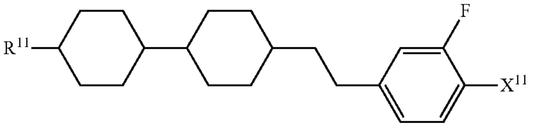
(3-6)
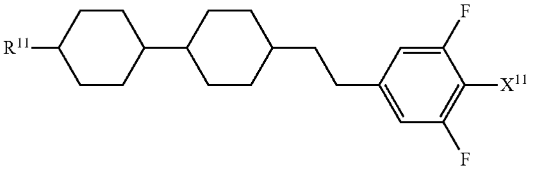
(3-7)
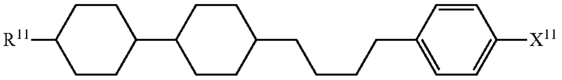
(3-8)
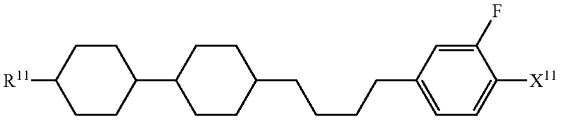
(3-9)
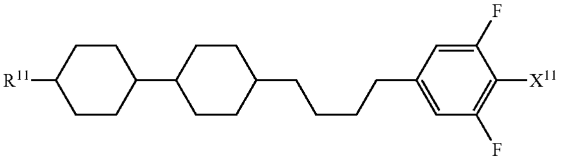
(3-10)
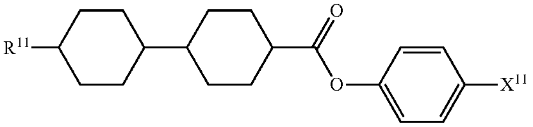
(3-11)
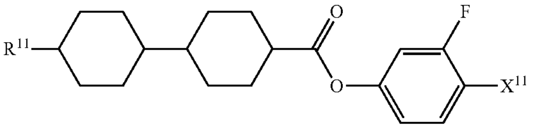

-continued
(3-12)
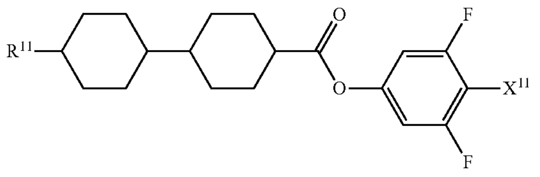
(3-13)
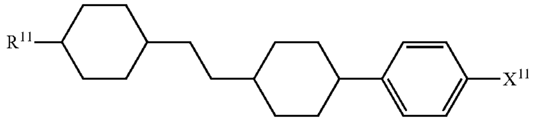
(3-14)
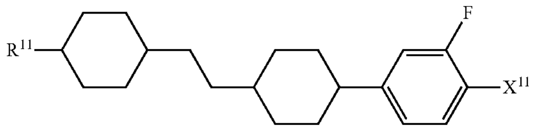
(3-15)
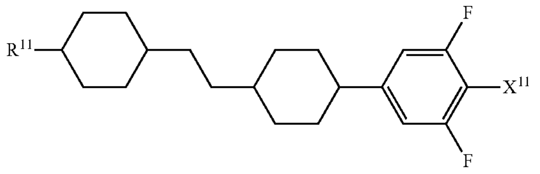
(3-16)
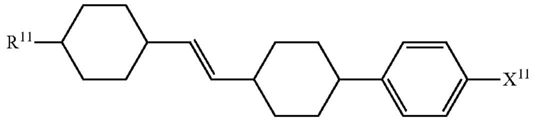
(3-17)
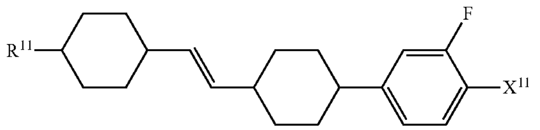
(3-18)
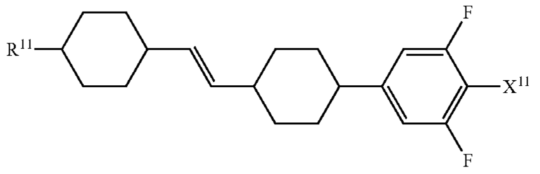
(3-19)
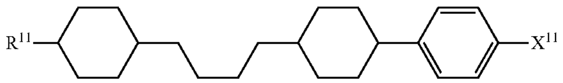
(3-20)
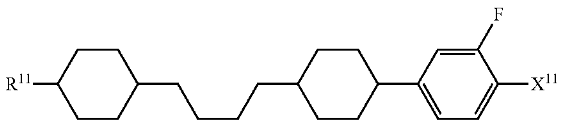
-continued
(3-21)
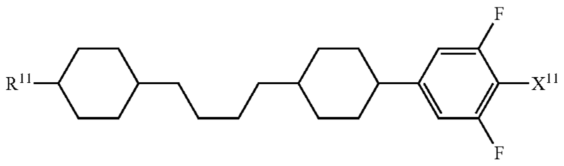
(3-22)
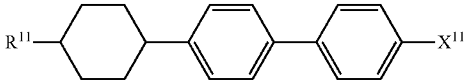
(3-23)
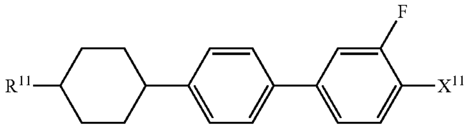
(3-24)
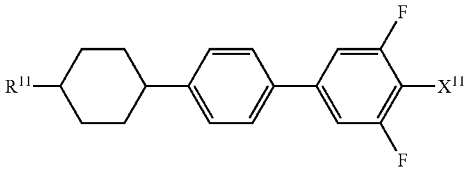
(3-25)
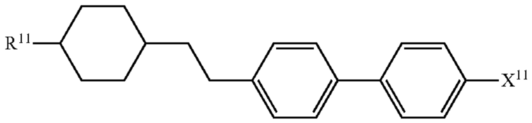
(3-26)
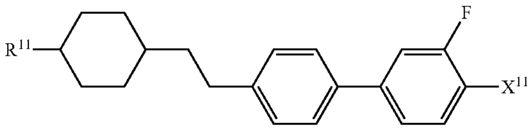
(3-27)
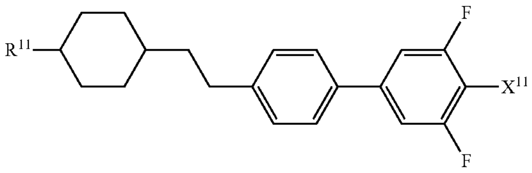
(3-28)
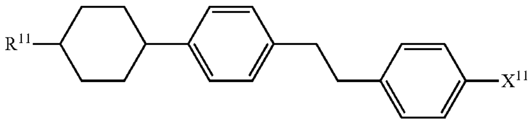
(3-29)
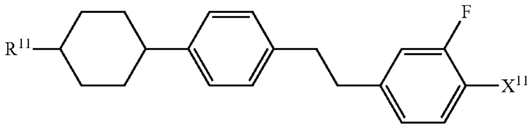
(3-30)
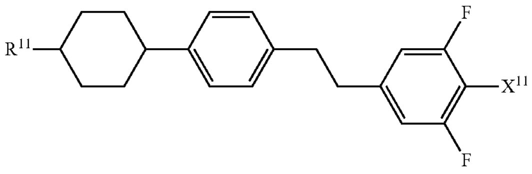

-continued
(3-31)
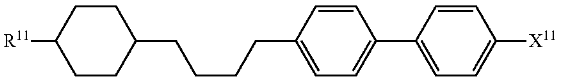
(3-32)
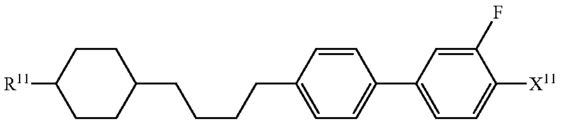
(3-33)
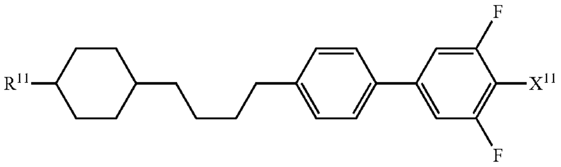
(3-34)
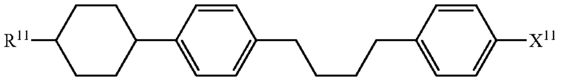
(3-35)
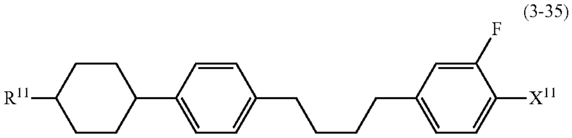
(3-36)
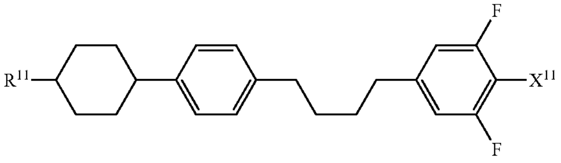
(3-37)
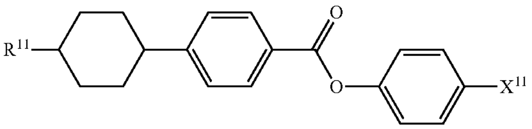
(3-38)
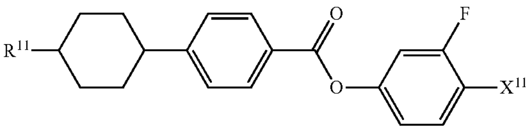
(3-39)
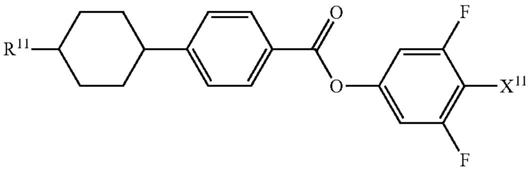
(3-40)
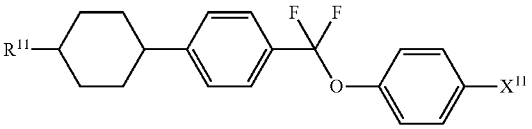
-continued
(3-41)
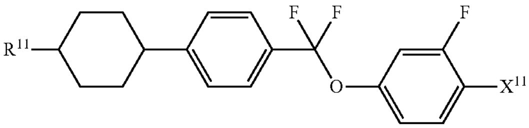
(3-42)
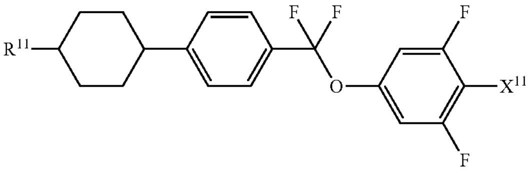
(3-43)
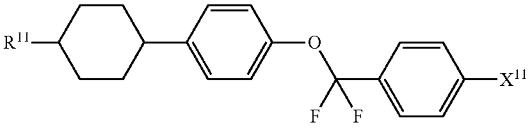
(3-44)
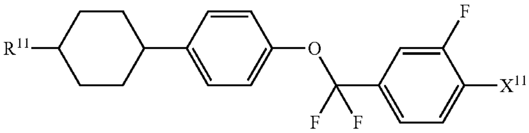
(3-45)
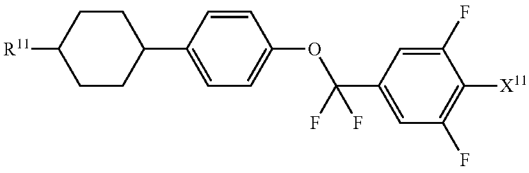
(3-46)
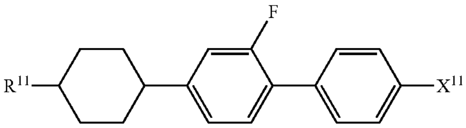
(3-47)
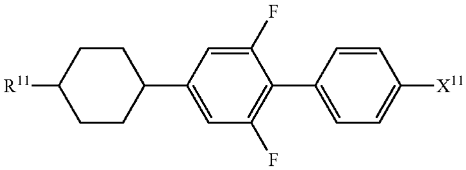
(3-48)
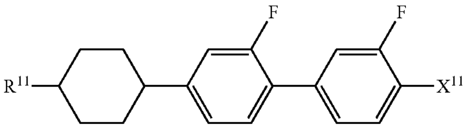
(3-49)
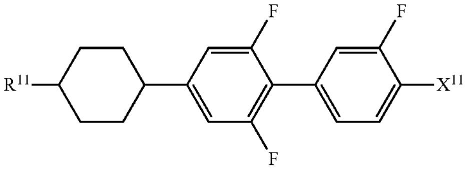

-continued
(3-50)
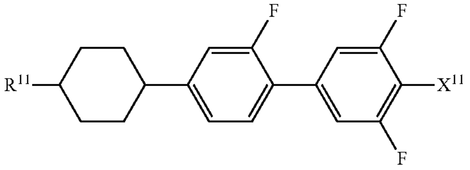
(3-51)
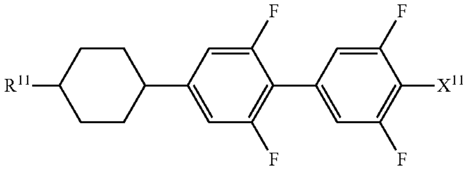
(3-52)
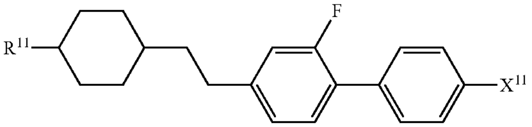
(3-53)
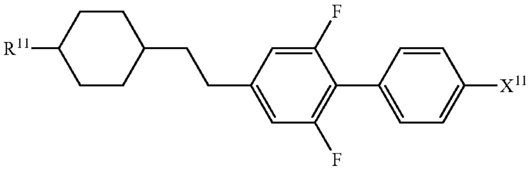
(3-54)
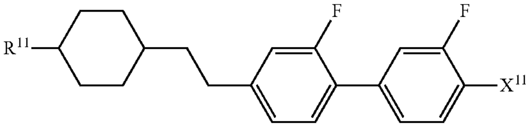
(3-55)
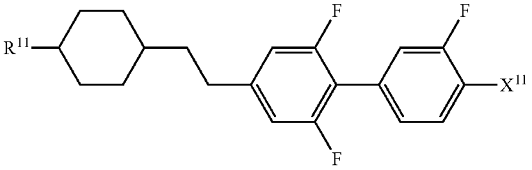
(3-56)
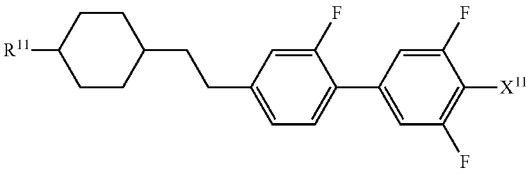
(3-57)
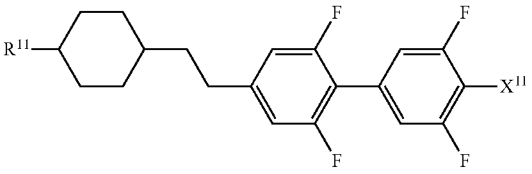
-continued
(3-58)
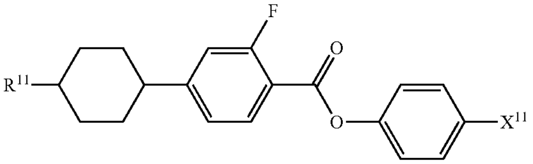
(3-59)
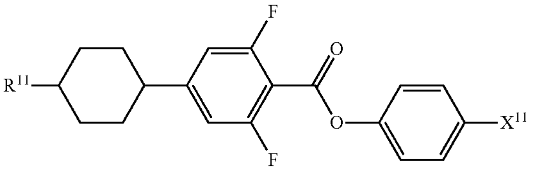
(3-60)
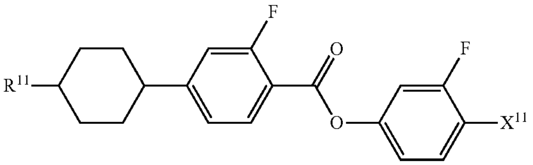
(3-61)
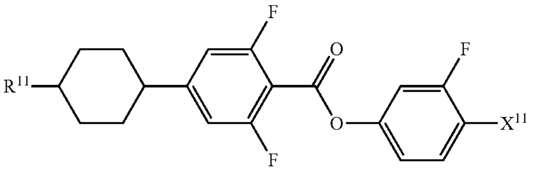
(3-62)
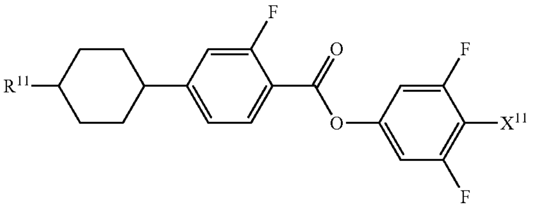
(3-63)
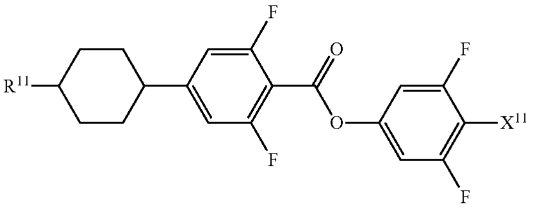
(3-64)
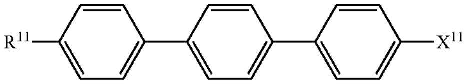
(3-65)
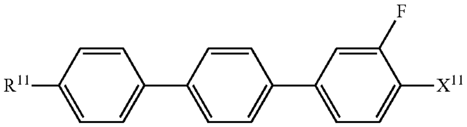

-continued
(3-66)
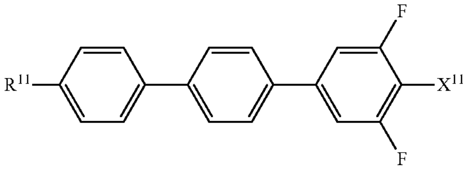
(3-67)
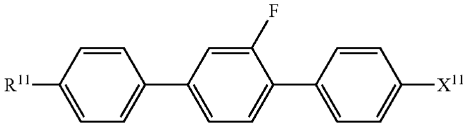
(3-68)
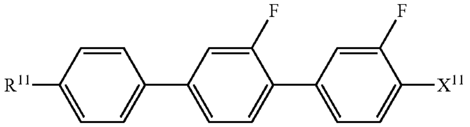
(3-69)
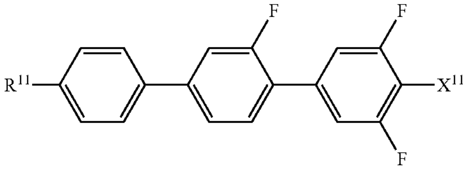
(3-70)
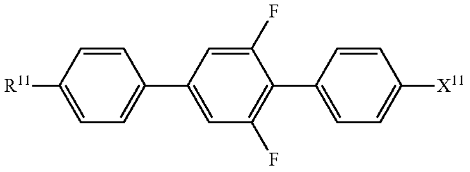
(3-71)
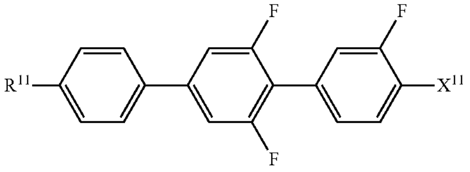
(3-72)
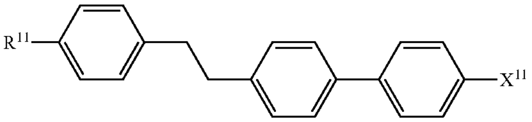
(3-73)
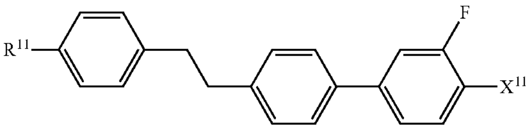
(3-74)
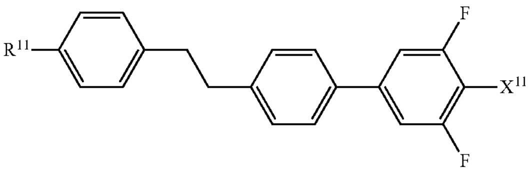
-continued
(3-75)
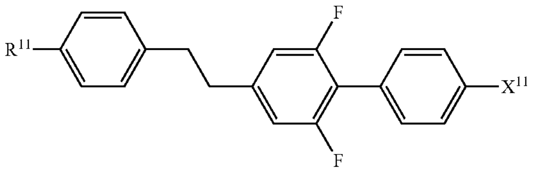
(3-76)
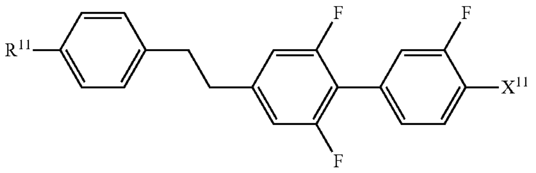
(3-77)
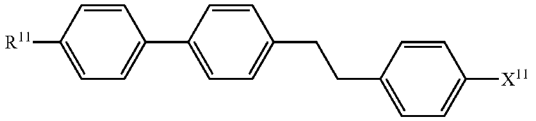
(3-78)
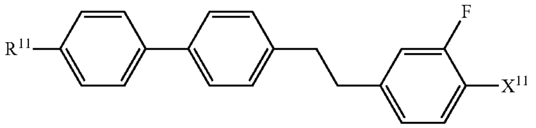
(3-79)
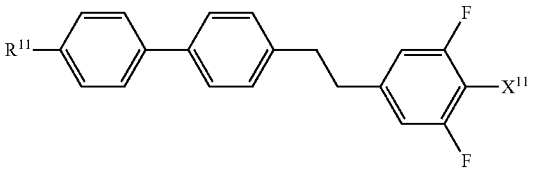
(3-80)
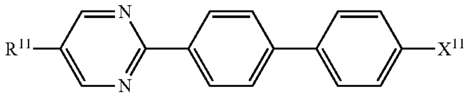
(3-81)
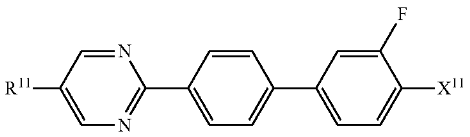
(3-82)
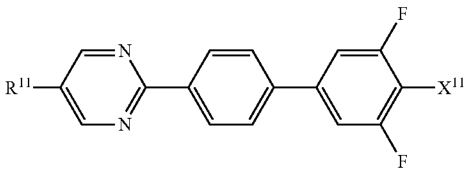
(3-83)
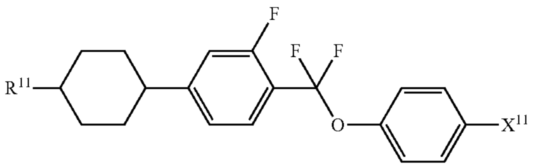

-continued
(3-84)
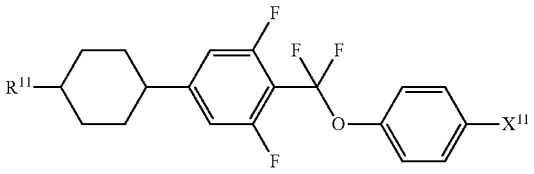
(3-85)
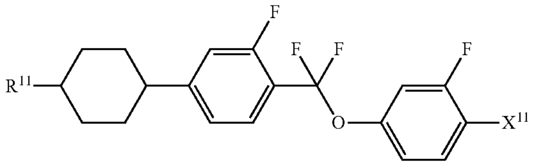
(3-86)
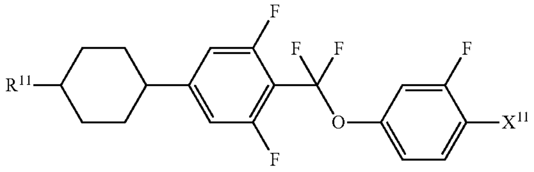
(3-87)
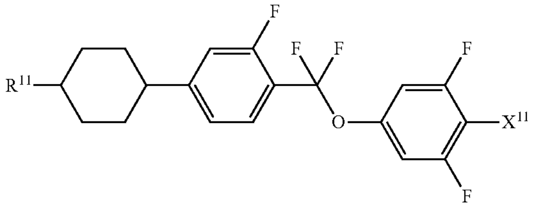
(3-88)
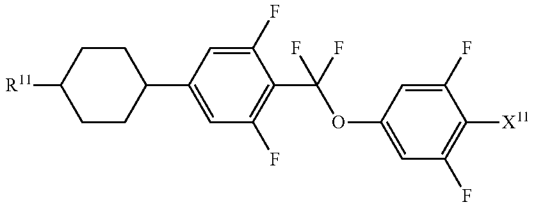
(3-89)
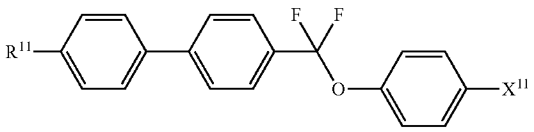
(3-90)
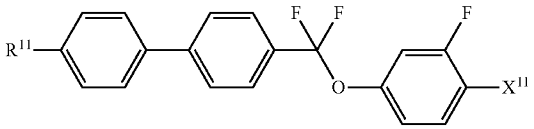
(3-91)
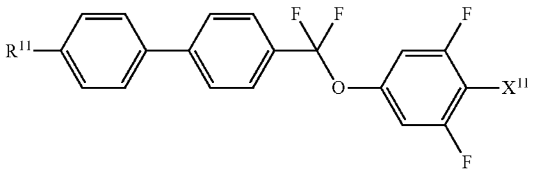
-continued
(3-92)
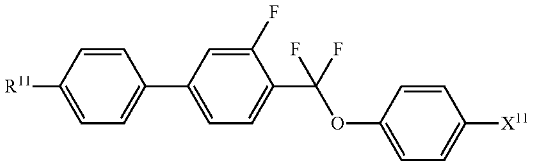
(3-93)
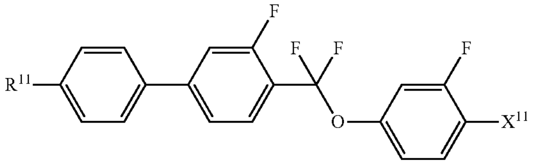
(3-94)
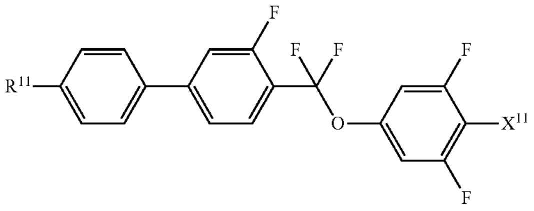
(3-95)
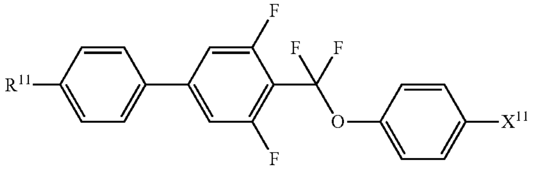
(3-96)
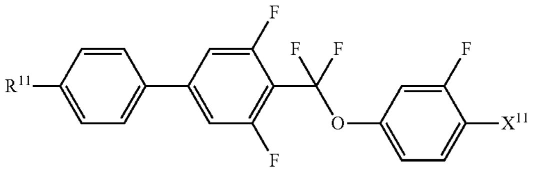
(3-97)
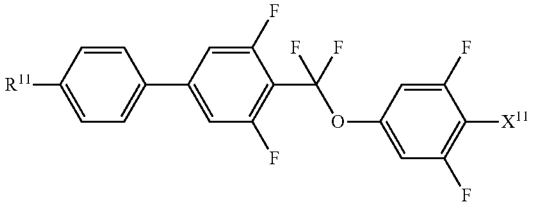
(3-98)
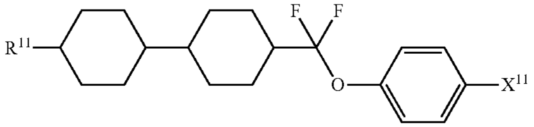
(3-99)
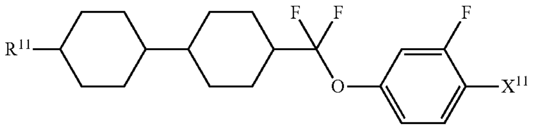

-continued
(3-100)
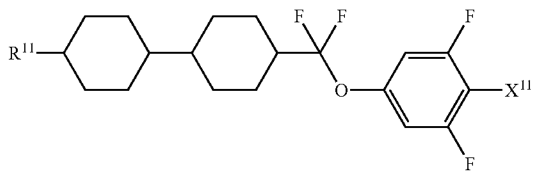
(3-101)
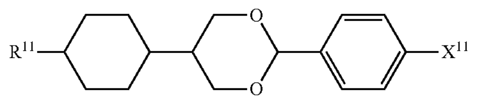
(3-102)
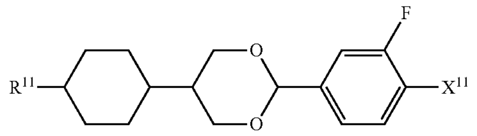
(3-103)
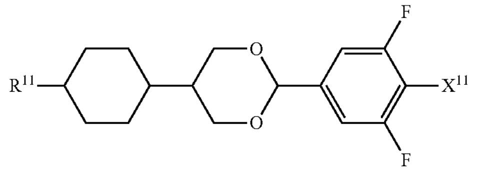
(3-104)
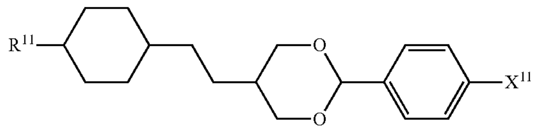
(3-105)
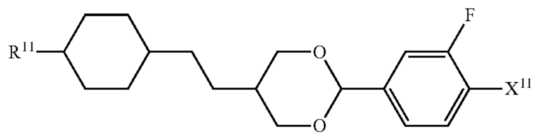
(3-106)
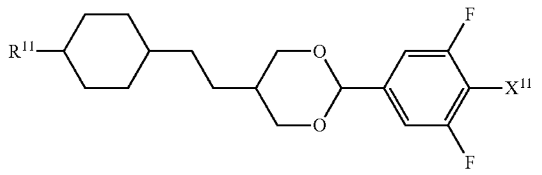
(3-107)
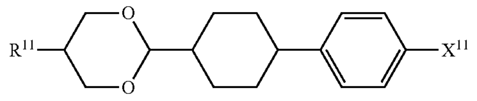
(3-108)
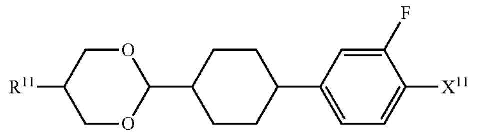
-continued
(3-109)
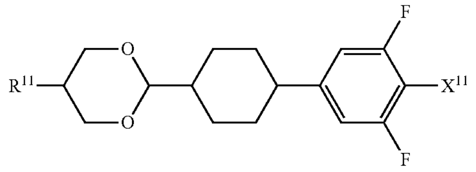
(3-110)
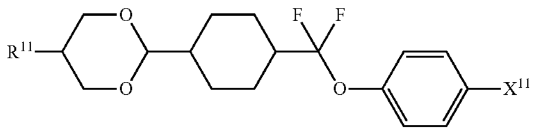
(3-111)
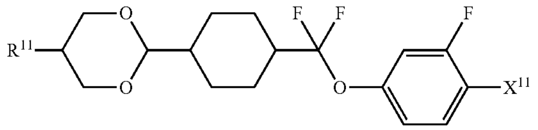
(3-112)
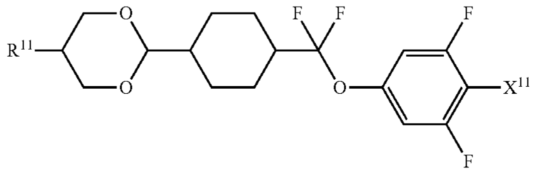
(3-113)
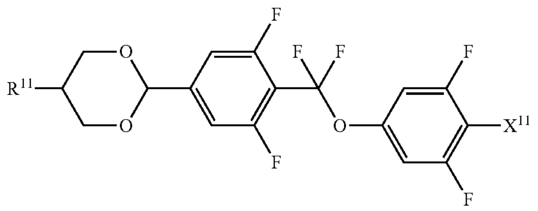
(4-1)
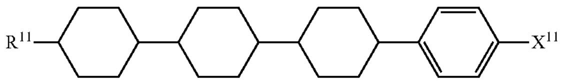
(4-2)
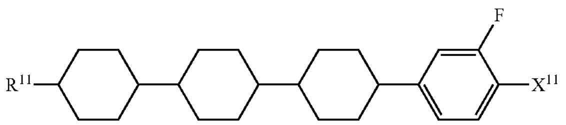
(4-3)
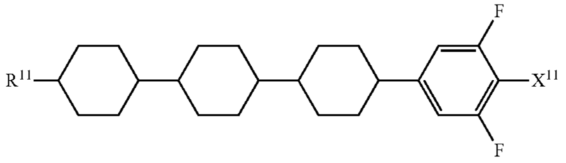
(4-4)
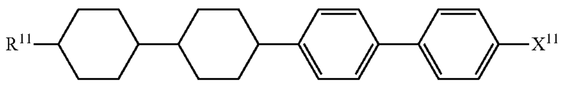

-continued
(4-5)
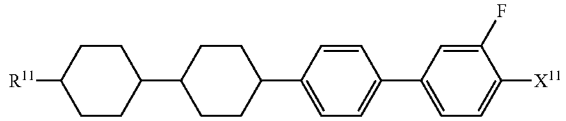
(4-6)
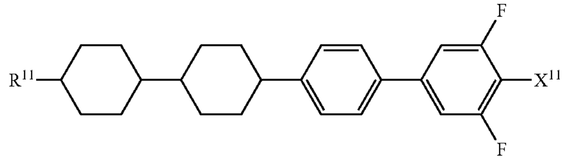
(4-7)
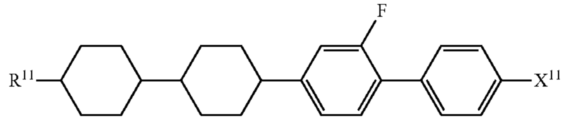
(4-8)
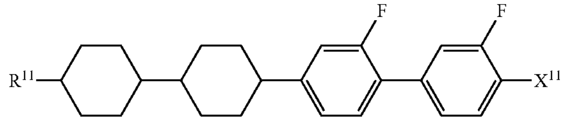
(4-9)
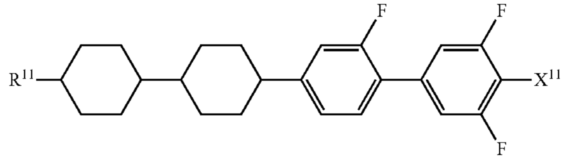
(4-10)
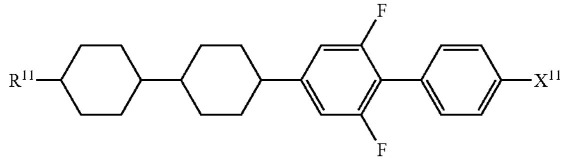
(4-11)
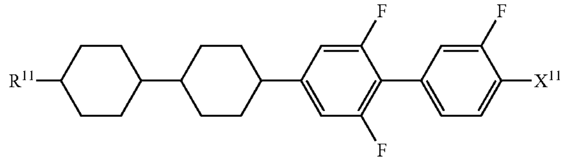
(4-12)
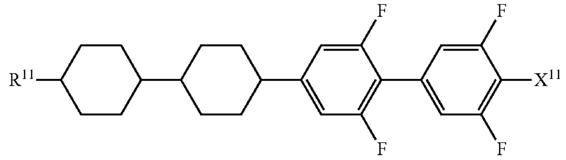
(4-13)
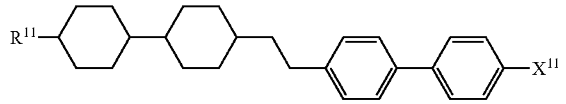
-continued
(4-14)
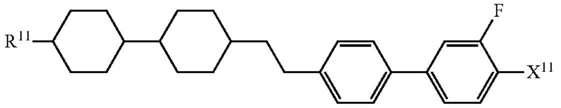
(4-15)
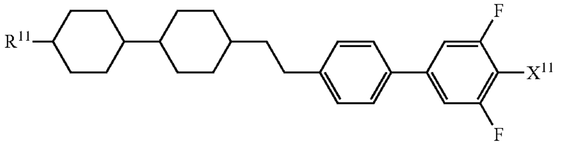
(4-16)
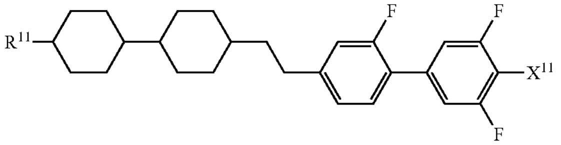
(4-17)
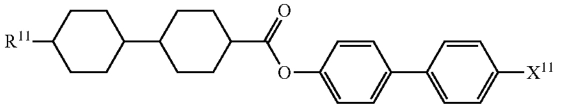
(4-18)
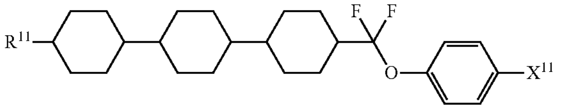
(4-19)
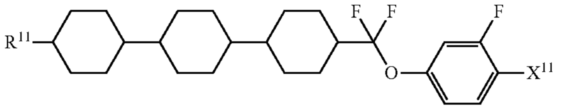
(4-20)
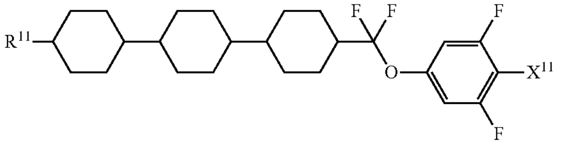
(4-21)
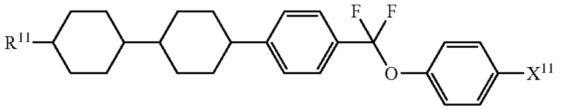
(4-22)
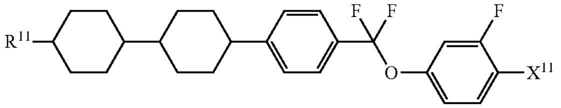
(4-23)
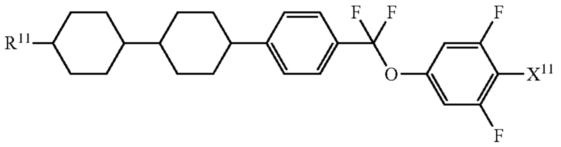

-continued
(4-24)
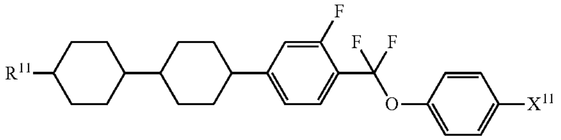
(4-25)
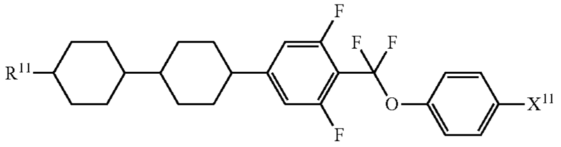
(4-26)
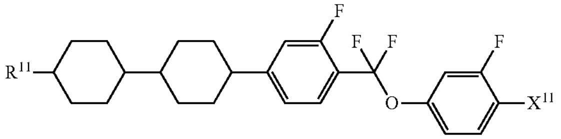
(4-27)
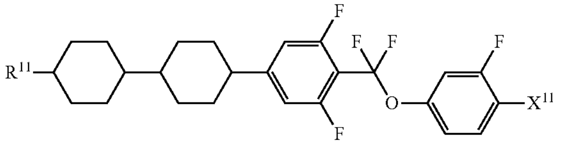
(4-28)
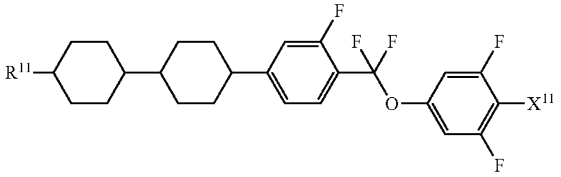
(4-29)
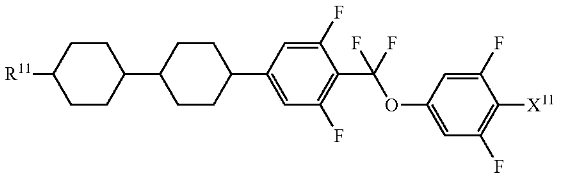
(4-30)
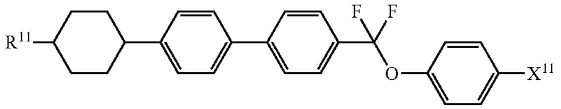
(4-31)
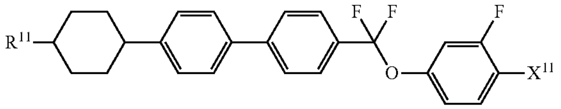
(4-32)
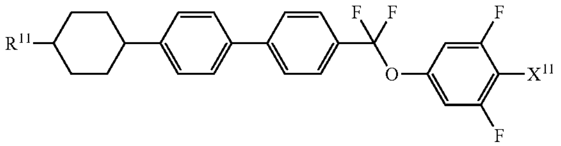
-continued
(4-33)
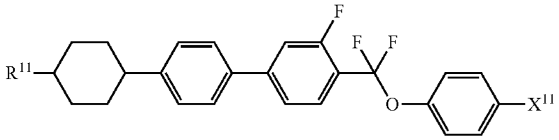
(4-34)
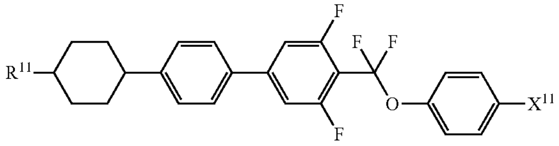
(4-35)
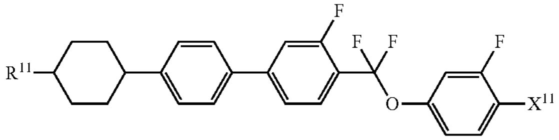
(4-36)
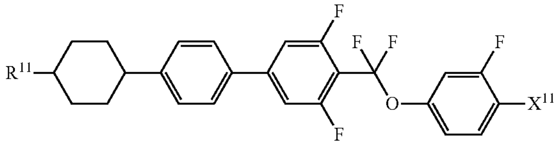
(4-37)
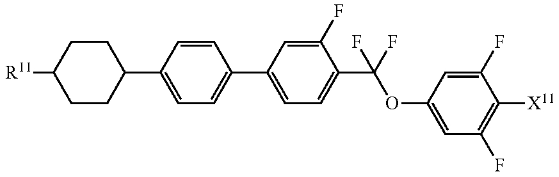
(4-38)
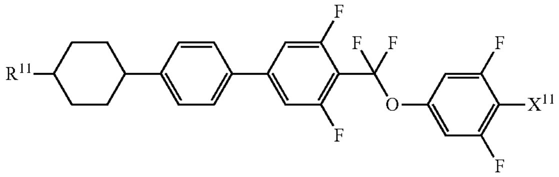
(4-39)
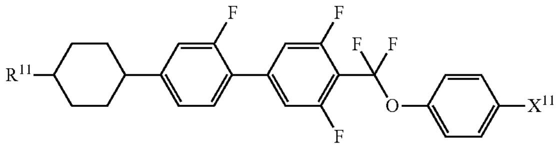
(4-40)
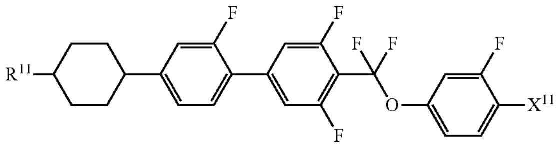

-continued
(4-41)
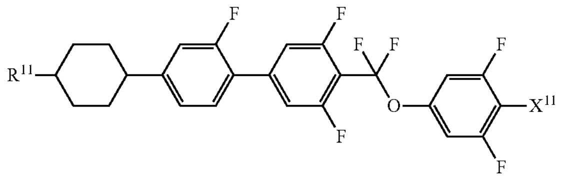
(4-42)
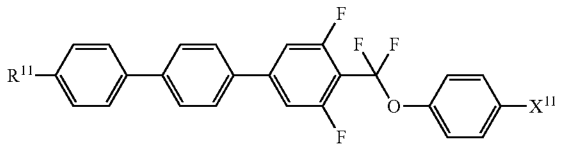
(4-43)
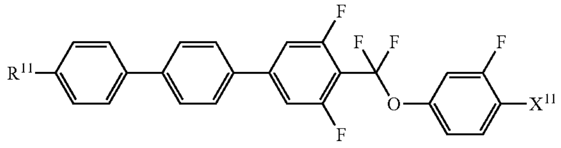
(4-44)
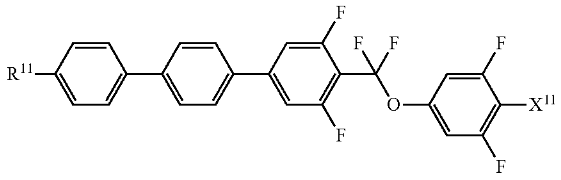
(4-45)
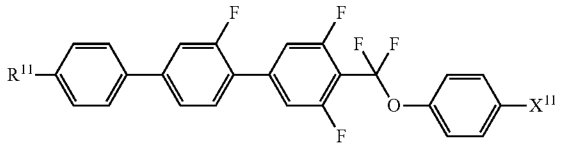
(4-46)
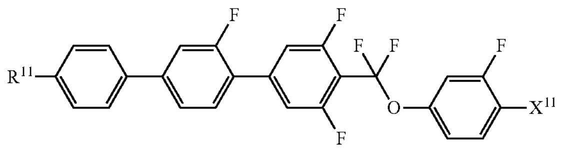
(4-47)
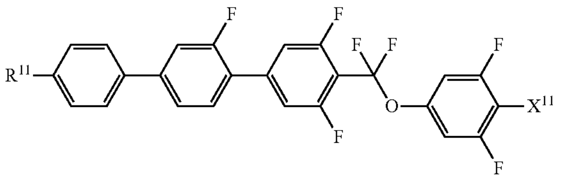
(4-48)
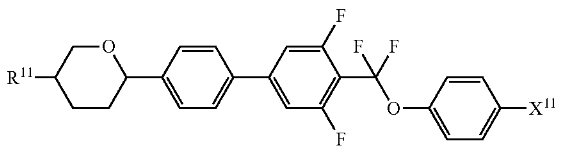
-continued
(4-49)
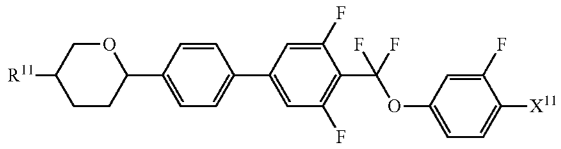
(4-50)
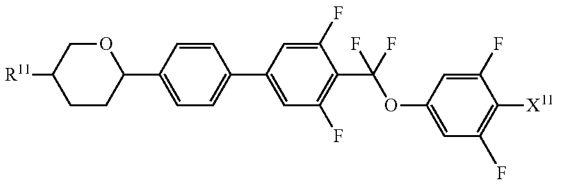
(4-51)
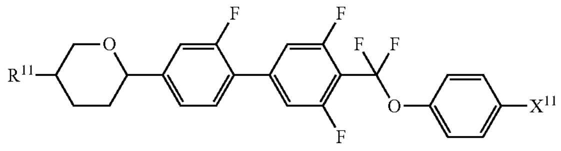
(4-52)
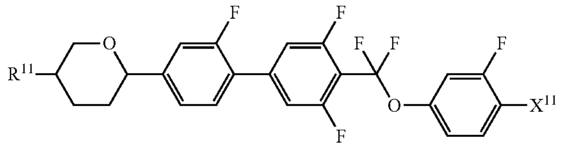
(4-53)
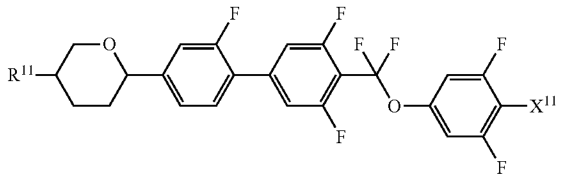
(4-54)
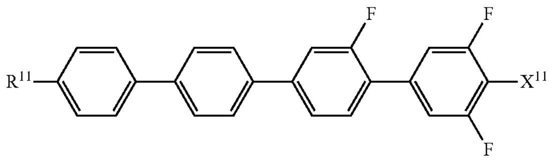
(4-55)
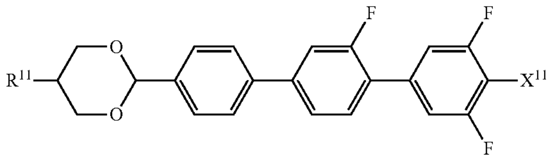
(4-56)
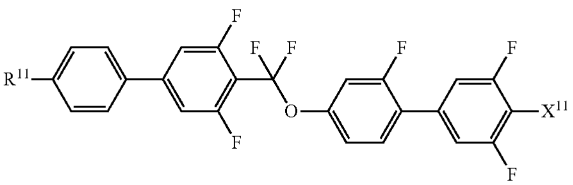

-continued (4-57)

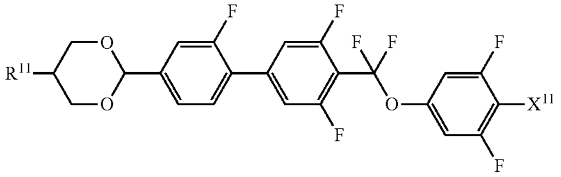

Component B has positive dielectric anisotropy and superb stability to heat, light or the like, and therefore is used when preparing a composition for a mode such as PS-IPS, PS-FFS and PSA-OCB. A content of component B is suitably, based on the liquid crystal composition, in the range from approximately 1% by weight to approximately 99% by weight, preferably, in the range from approximately 10% by weight to approximately 97% by weight, and further preferably, in the range from approximately 40% by weight to approximately 95% by weight. Further addition of compounds (13) to (15) (component E) allows adjustment of viscosity of the composition. When component B is added to a composition having negative dielectric anisotropy, a content of component B is preferably in the range of approximately 30% by weight or less based on the liquid crystal composition. Addition of component B allows adjustment of an elastic constant of the composition and adjustment of a voltage-transmittance curve of a device.

Component C includes compound (5) in which a right-terminal group is $-C\equiv N$ or $-C\equiv C-C\equiv N$. Specific preferred examples of component C include compounds (5-1) to (5-64). In the compounds of component C, $R^{12}$ and $X^{12}$ are defined in a manner identical with the definitions in item 12.

(5-1)

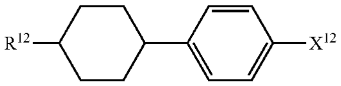

(5-2)

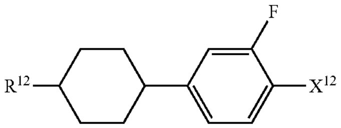

(5-3)

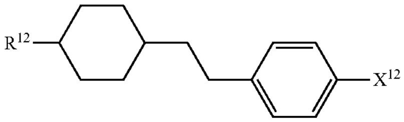

(5-4)

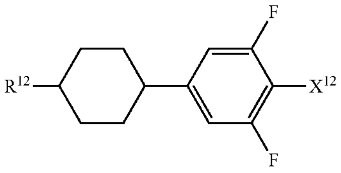

(5-5)

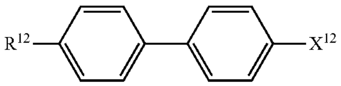

-continued (5-6)

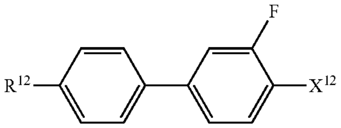

(5-7)

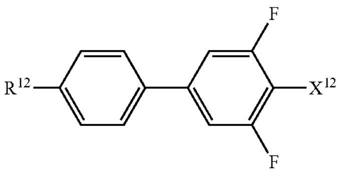

(5-8)

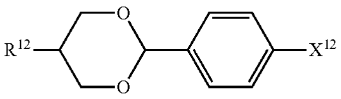

(5-9)

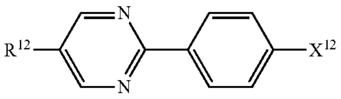

(5-10)

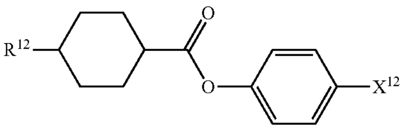

(5-11)

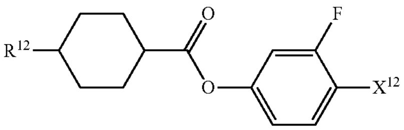

(5-12)

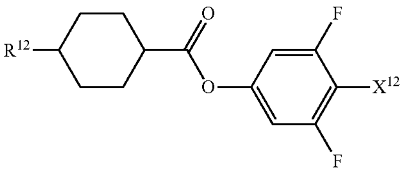

(5-13)

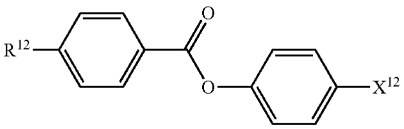

(5-14)

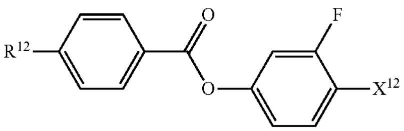

(5-15)

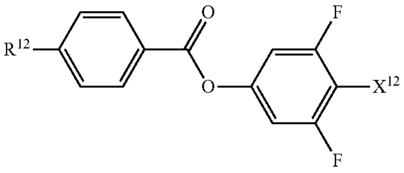

(5-16)

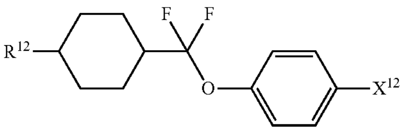

-continued
(5-17)
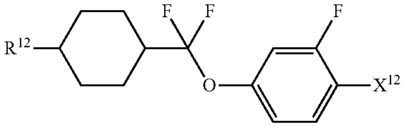
(5-18)
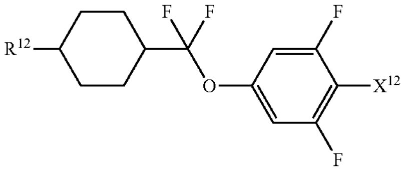
(5-19)
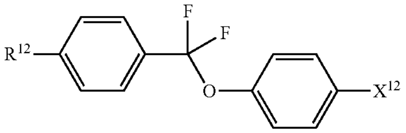
(5-20)
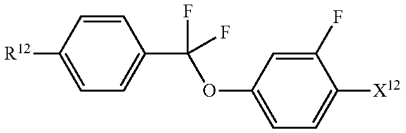
(5-21)
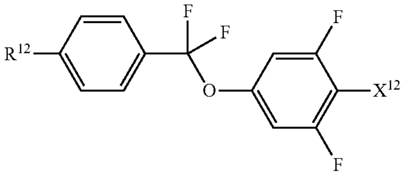
(5-22)
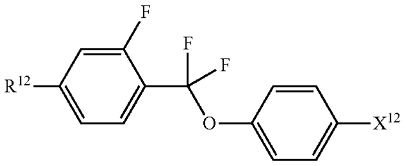
(5-23)
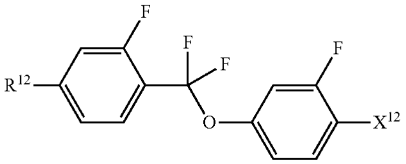
(5-24)
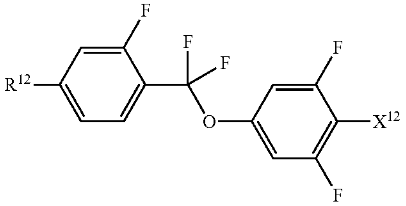
(5-25)
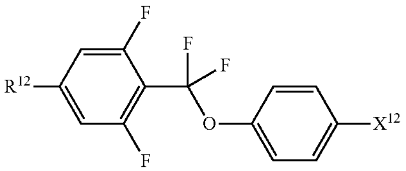
-continued
(5-26)
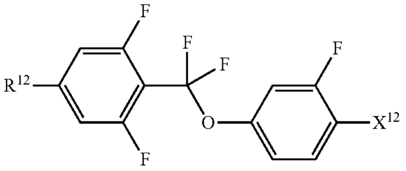
(5-27)
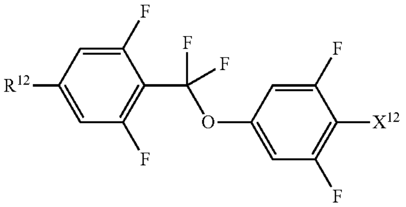
(5-28)
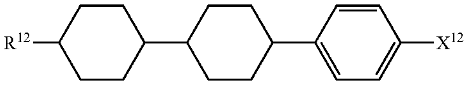
(5-29)
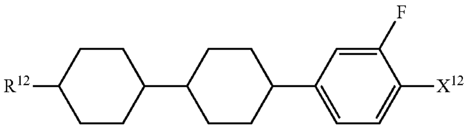
(5-30)
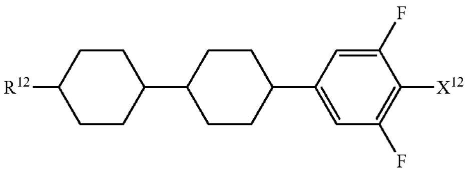
(5-31)
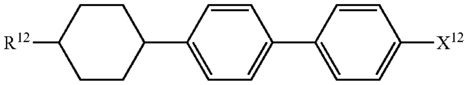
(5-32)
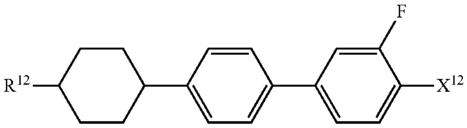
(5-33)
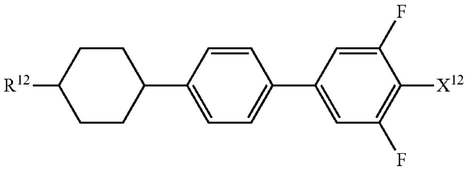
(5-34)
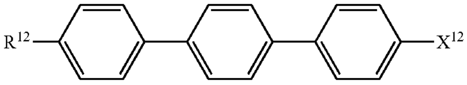
(5-35)
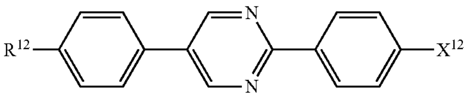
(5-36)
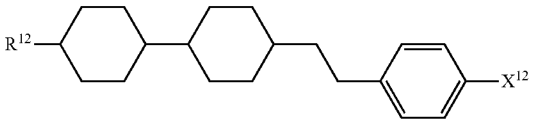

-continued
(5-37)
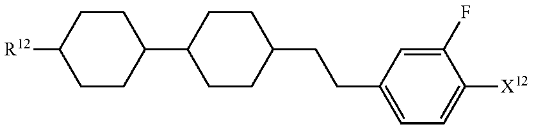
(5-38)
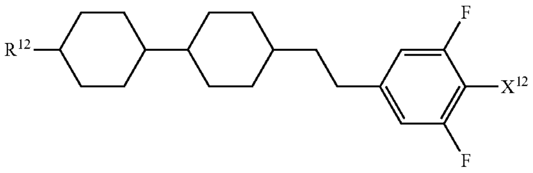
(5-39)
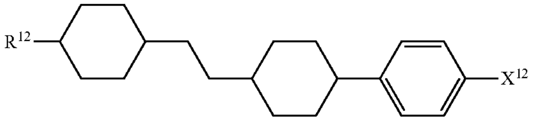
(5-40)
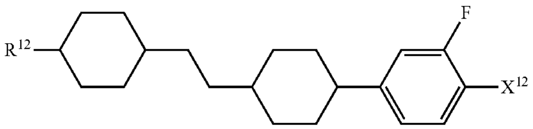
(5-41)
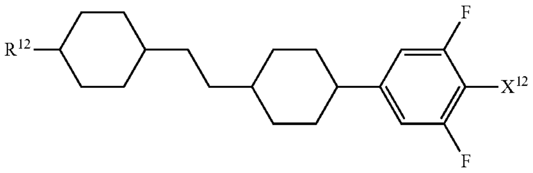
(5-42)
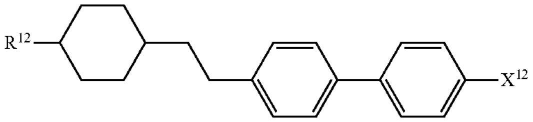
(5-43)
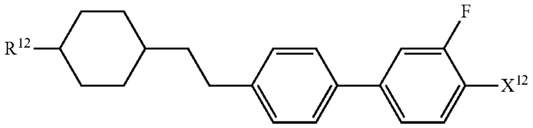
(5-44)
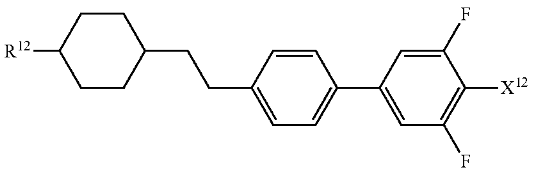
(5-45)
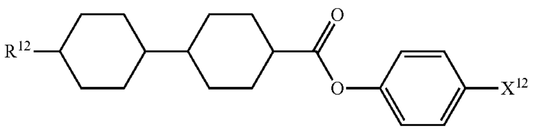
-continued
(5-46)
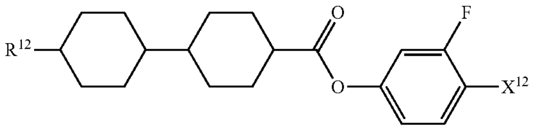
(5-47)
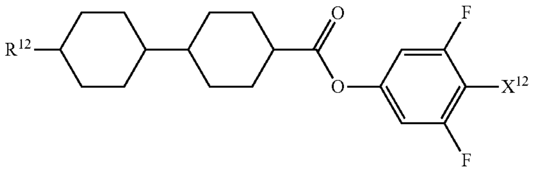
(5-48)
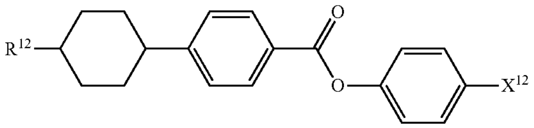
(5-49)
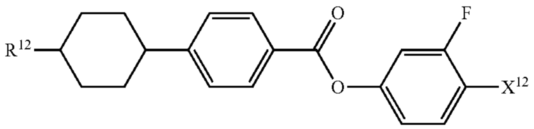
(5-50)
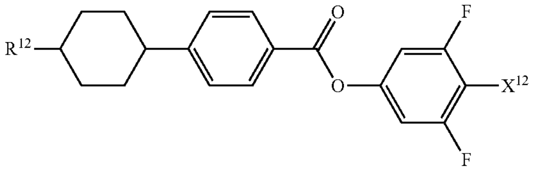
(5-51)
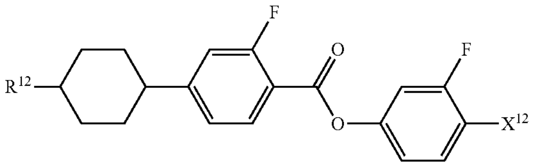
(5-52)
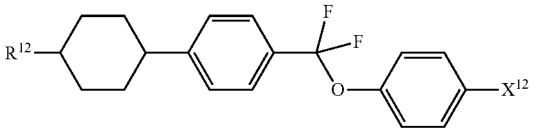
(5-53)
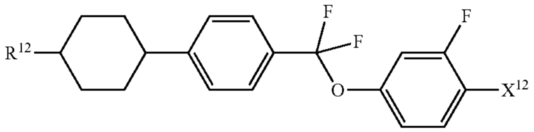
(5-54)
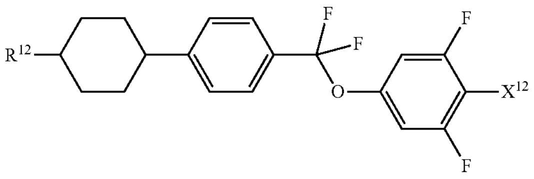

-continued (5-55)

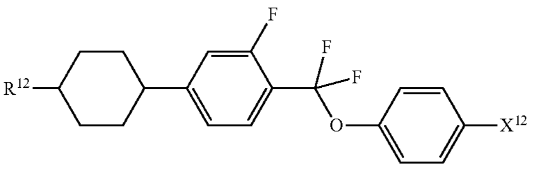

(5-56)

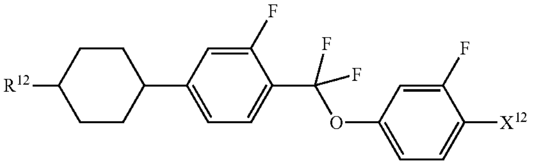

(5-57)

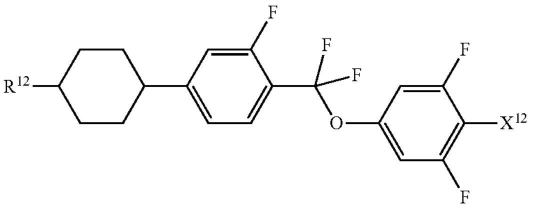

(5-58)

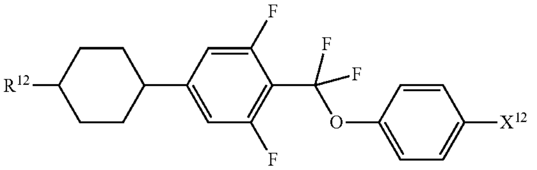

(5-59)

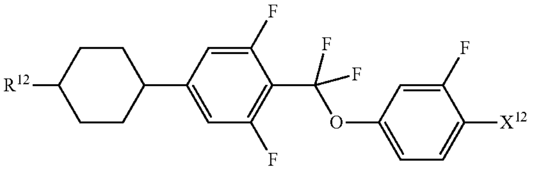

(5-60)

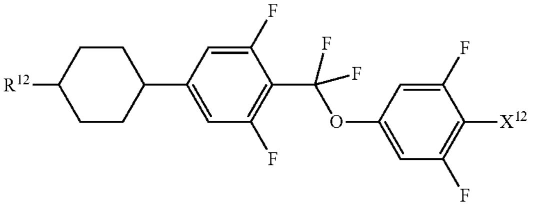

(5-61)

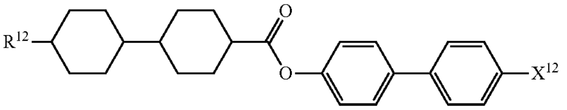

(5-62)

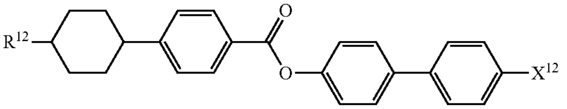

-continued (5-63)

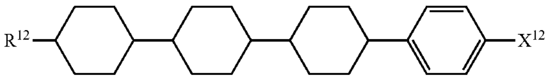

(5-64)

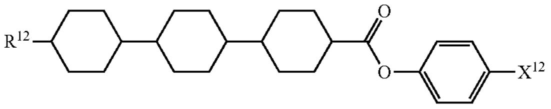

Component C has a large value of positive dielectric anisotropy, and therefore is mainly used when preparing a composition for a mode such as PS-TN. Dielectric anisotropy of the composition can be increased by adding component C. Component C is effective in extending a temperature range of the liquid crystal phase, adjusting viscosity or adjusting optical anisotropy. Component C is also useful to adjustment of the voltage-transmittance curve of the device.

When preparing the composition for the mode such as PS-TN, a content of component C is suitably, based on the liquid crystal composition, in the range from approximately 1% by weight to approximately 99% by weight, preferably, in the range from approximately 10% by weight to approximately 97% by weight, and further preferably, in the range from approximately 40% by weight to approximately 95% by weight. Further addition of component E allows adjustment of the temperature range of the liquid crystal phase, the viscosity, the optical anisotropy, the dielectric anisotropy or the like. When component C is added to a composition having negative dielectric anisotropy, a content of component C is preferably in the range of approximately 30% by weight or less based on the liquid crystal composition. Addition of component C allows adjustment of the elastic constant of the composition and adjustment of the voltage-transmittance curve of the device.

Component D includes compounds (6) to (12). The compounds have a benzene ring lateral positions of which are replaced by two of halogen, such as 2,3-difluoro-1,4-phenylene. Specific preferred examples of component D include compounds (6-1) to (6-8), compounds (7-1) to (7-17), compound (8-1), compounds (9-1) to (9-3), compounds (10-1) to (10-11), compounds (11-1) to (11-3) and compounds (12-1) to (12-3). In the compounds of component D, $R^{13}$, $R^{14}$ and $R^{15}$ are defined in a manner identical with the definitions in item 13 described above.

(6-1)

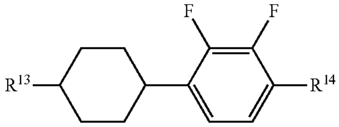

(6-2)

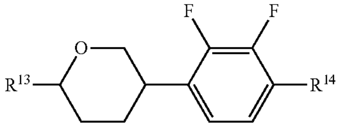

-continued
(6-3)
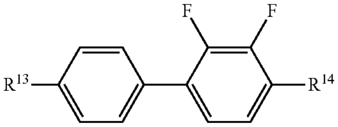
(6-4)
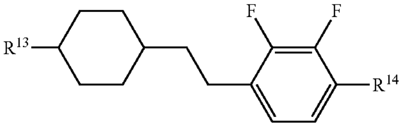
(6-5)
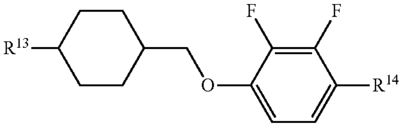
(6-6)
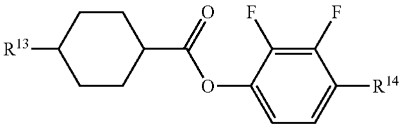
(6-7)
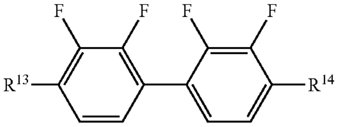
(6-8)
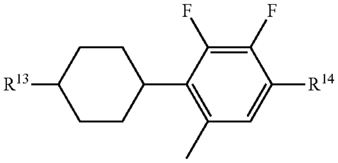
(7-1)
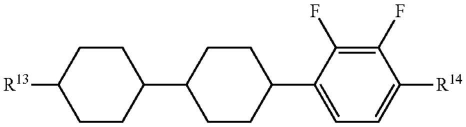
(7-2)
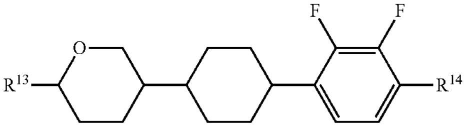
(7-3)
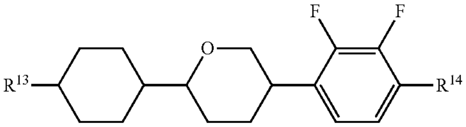
(7-4)
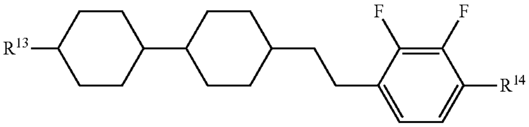
-continued
(7-5)
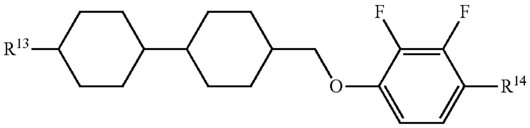
(7-6)
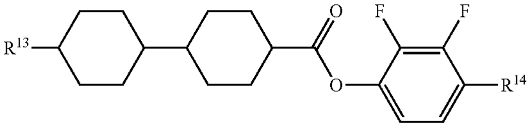
(7-7)
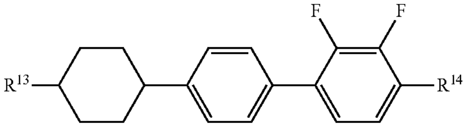
(7-8)
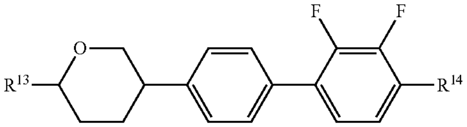
(7-9)
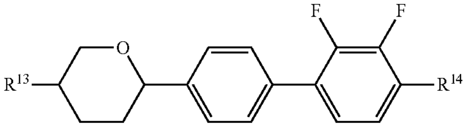
(7-10)
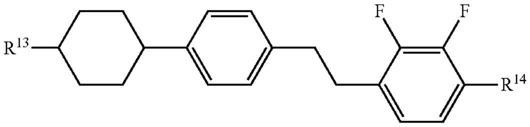
(7-11)
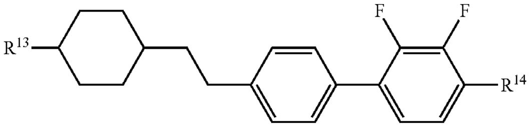
(7-12)
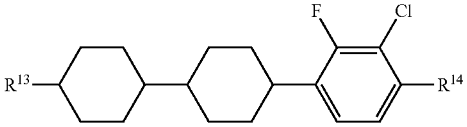
(7-13)
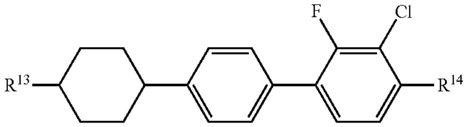
(7-14)
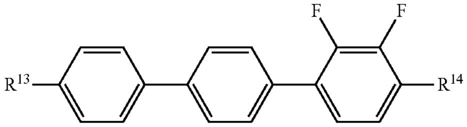
(7-15)
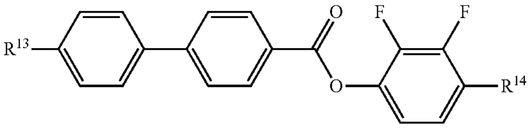

-continued
(7-16)
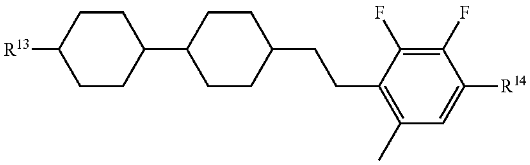
(7-17)
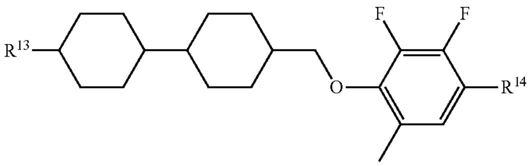
(8-1)
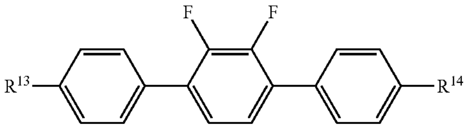
(9-1)
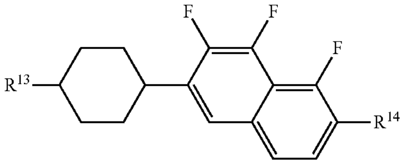
(9-2)
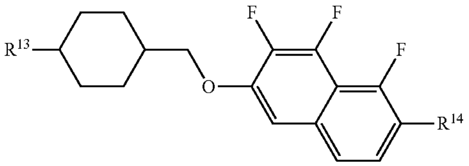
(9-3)
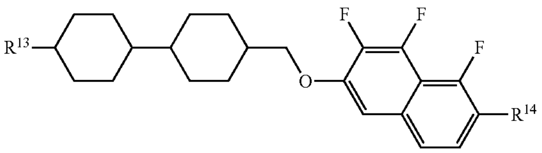
(10-1)
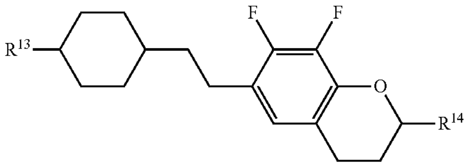
(10-2)
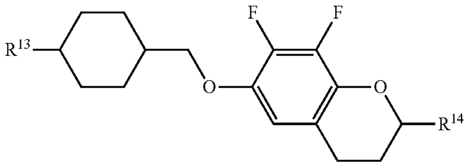
(10-3)
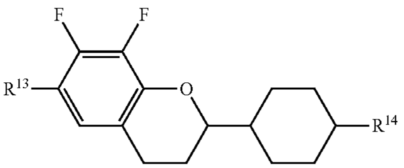
-continued
(10-4)
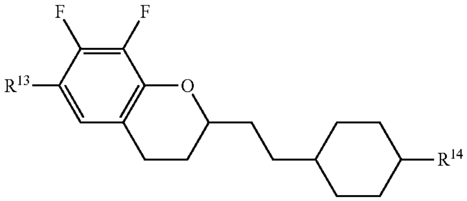
(10-5)
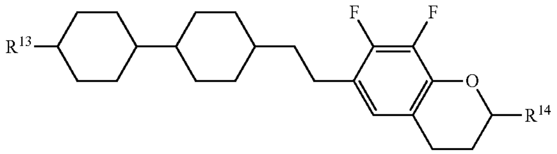
(10-6)
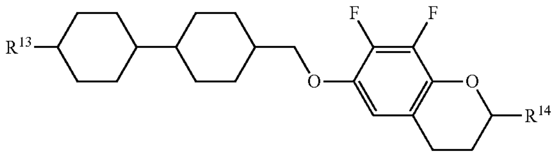
(10-7)
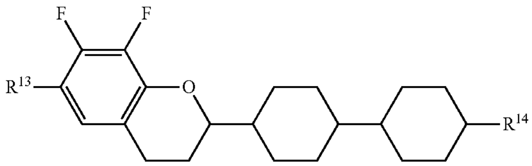
(10-8)
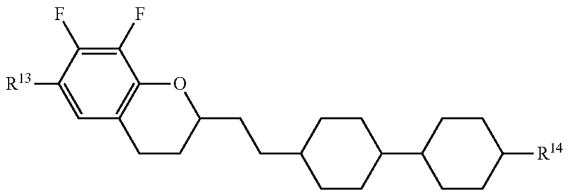
(10-9)
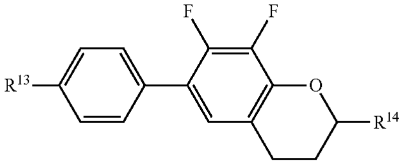
(10-10)
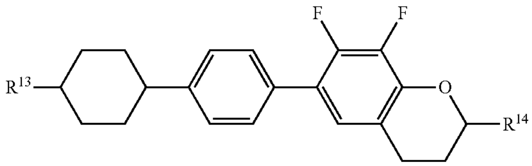
(10-11)
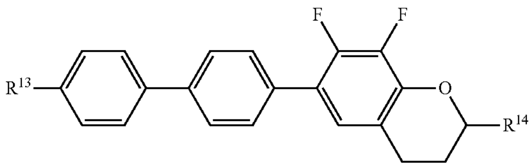

-continued (11-1)

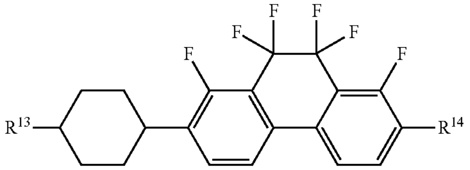

(11-2)

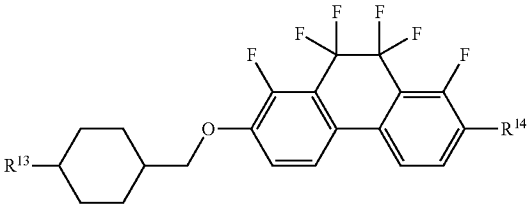

(11-3)

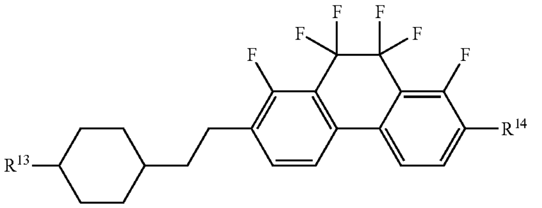

(12-1)

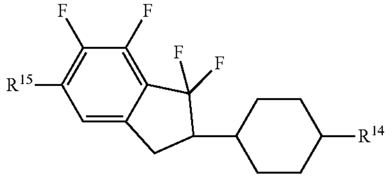

(12-2)

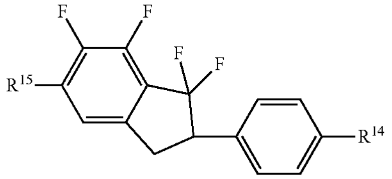

(12-3)

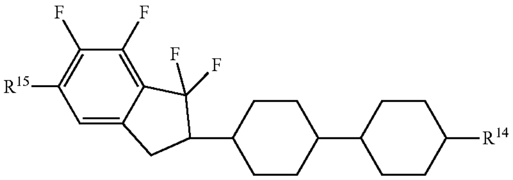

Component D includes a compound having negative dielectric anisotropy. Component D is used when preparing a composition for a mode such as PS-IPS, PS-FFS and PSA-VA. If a content of component D is increased, dielectric anisotropy of the composition is negatively increased, but viscosity increases. Thus, the content is preferably decreased, as long as a required value of threshold voltage of a device is satisfied. Accordingly, in consideration of approximately 5 of an absolute value of dielectric anisotropy, the content is preferably in the range of approximately 40% by weight or more in order to allow sufficient voltage driving.

Among types of compound D, compound (6) is a bicyclic compound, and therefore effective mainly in adjusting the viscosity, the optical anisotropy or the dielectric anisotropy. Compounds (7) and (8) each are a tricyclic compound, and therefore effective in increasing the maximum temperature, the optical anisotropy or the dielectric anisotropy. Compounds (9) to (12) each are effective in increasing the dielectric anisotropy.

When preparing the composition for the mode such as PS-IPS, PS-FFS and PSA-VA, the content of component D is preferably, based on the liquid crystal composition, in the range of approximately 40% by weight or more, and further preferably, in the range from approximately 40% by weight to approximately 95% by weight. Addition of component D allows adjustment of the elastic constant of the composition and adjustment of the voltage-transmittance curve of the device. When component D is added to a composition having positive dielectric anisotropy, a content of component D is preferably in the range of approximately 30% by weight or less based on the liquid crystal composition. Addition of component D allows adjustment of the elastic constant of the composition and adjustment of the voltage-transmittance curve of the device.

Component E includes a compound in which two terminal groups are alkyl or the like. Specific preferred examples of component E include compounds (13-1) to (13-11), compounds (14-1) to (14-19) and compounds (15-1) to (15-7). In the compounds of component E, $R^{16}$ and $R^{17}$ are defined in a manner identical with the definitions in item 14.

(13-1)

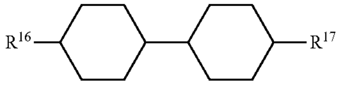

(13-2)

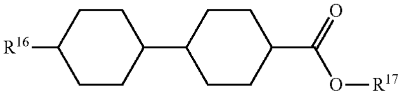

(13-3)

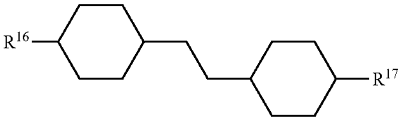

(13-4)

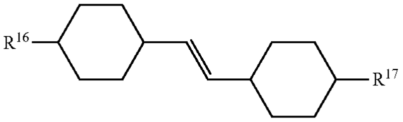

(13-5)

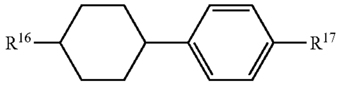

(13-6)

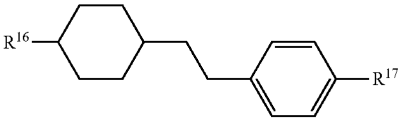

(13-7)

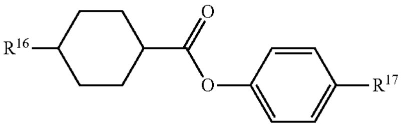

(13-8)

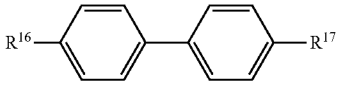

-continued
(13-9)
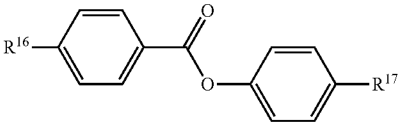
(13-10)
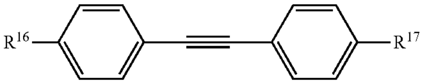
(13-11)
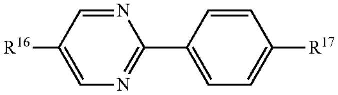
(14-1)
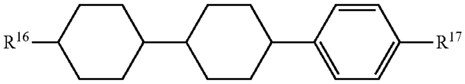
(14-2)
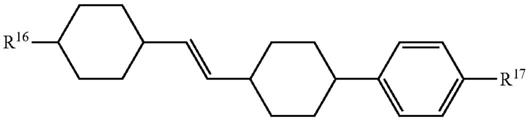
(14-3)
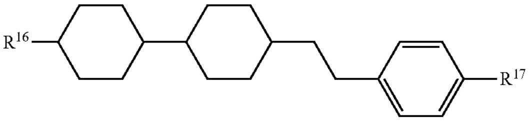
(14-4)
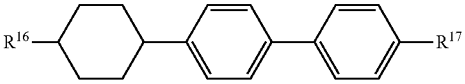
(14-5)
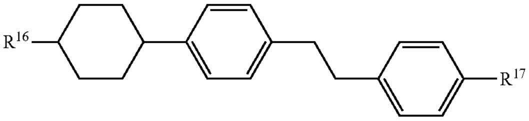
(14-6)
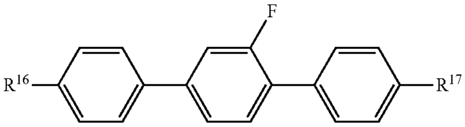
(14-7)
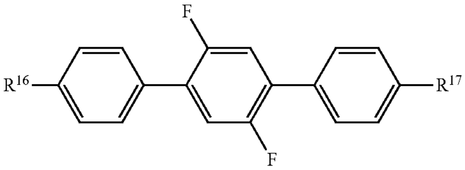
(14-8)
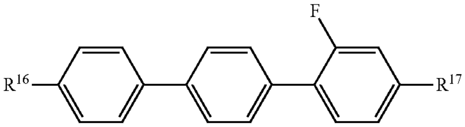
(14-9)
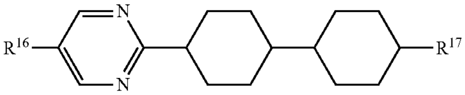
-continued
(14-10)
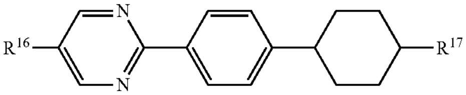
(14-11)
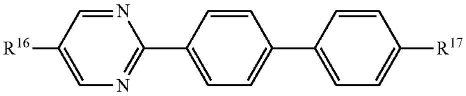
(14-12)
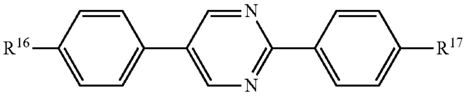
(14-13)
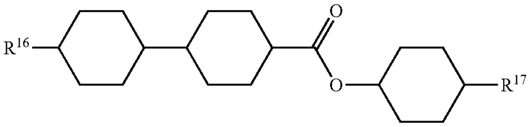
(14-14)
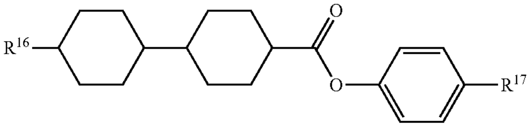
(14-15)
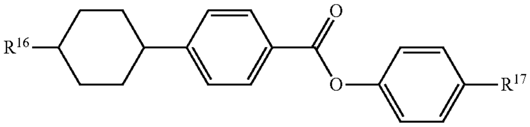
(14-16)
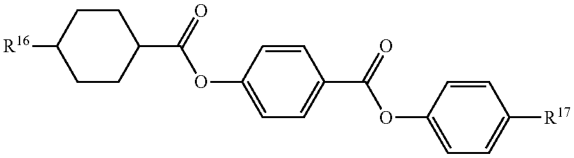
(14-17)
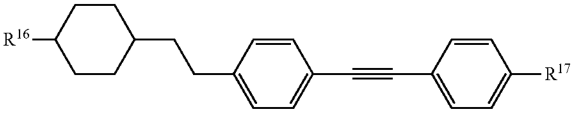
(14-18)
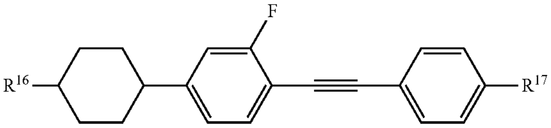
(14-19)
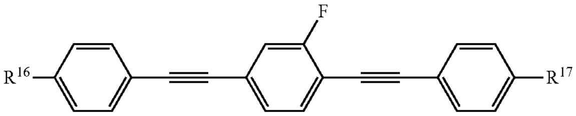
(15-1)
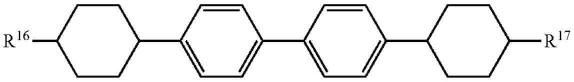

-continued (15-2)

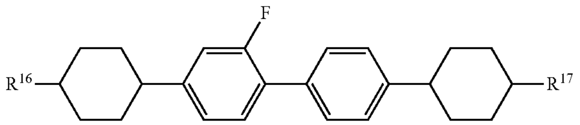

(15-3)

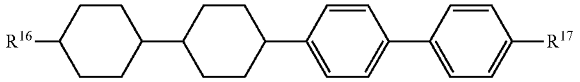

(15-4)

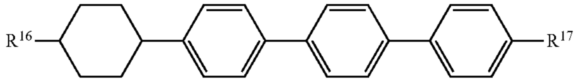

(15-5)

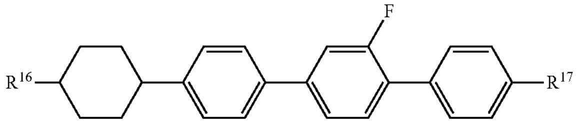

(15-6)

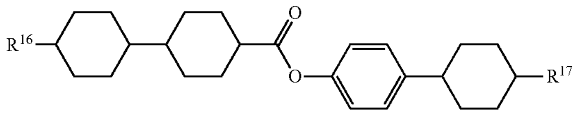

(15-7)

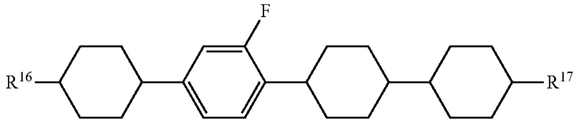

Component E has a small absolute value of dielectric anisotropy, and therefore is a compound close to neutrality. Compound (13) is effective mainly in adjusting the viscosity or the optical anisotropy. Compounds (14) and (15) are effective in extending the temperature range of the nematic phase by increasing the maximum temperature, or effective in adjusting the optical anisotropy.

If the content of component E is increased, the viscosity of the composition decreases, but the dielectric anisotropy decreases. Thus, the content is preferably increased, as long as a required value of threshold voltage of the device is satisfied. Accordingly, when preparing a composition for a mode such as PS-IPS and PSA-VA, the content of component E is preferably, based on the composition, in the range of approximately 30% by weight or more, and further preferably, in the range of approximately 40% by weight or more.

The polymerizable composition is prepared according to a method for dissolving required components at temperature higher than room temperature, or the like. According to an application, an additive may be added to the composition. Examples of the additives include an optically active compound, an antioxidant, an ultraviolet light absorber, a light stabilizer, a heat stabilizer, an antifoaming agent, a polymerization initiator and a polymerization inhibitor. Such additives are well known to those skilled in the art, and are described in literature.

The optically active compound is effective in inducing helical structure to provide liquid crystal molecules with a required twist angle, thereby preventing inverted twist. Addition of the optically active compound allows adjustment of a helical pitch. Two or more optically active compounds may be added thereto for the purpose of adjusting temperature dependence of the helical pitch. Specific preferred examples of the optically active compound include compounds (Op-1) to (Op-18) described below. In compound (Op-18), ring J is 1,4-cyclohexylene or 1,4-phenylene, and $R^{28}$ is alkyl having 1 to 10 carbons.

(Op-1)

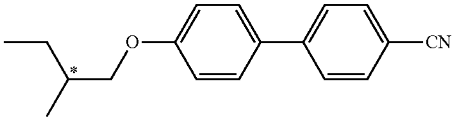

(Op-2)

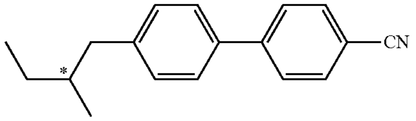

(Op-3)

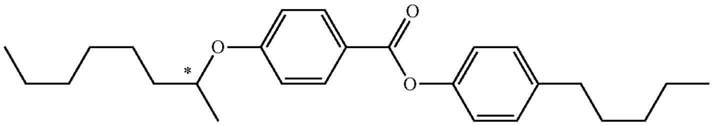

(Op-4)

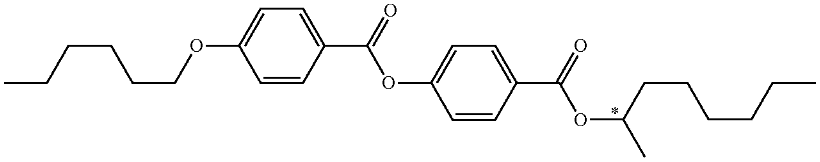

(Op-5)

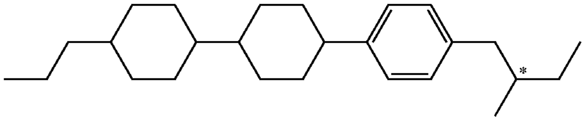

(Op-6)

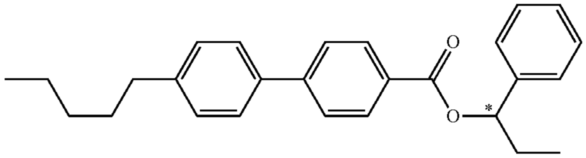

-continued
(Op-7)
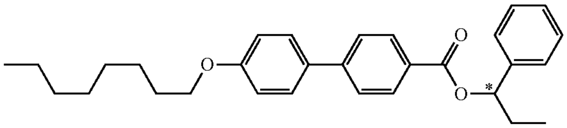
(Op-8)
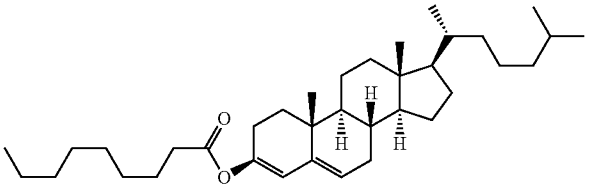
(Op-9)
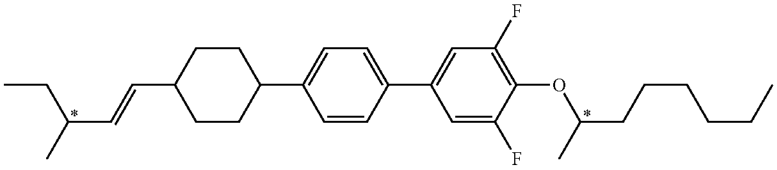
(Op-10)
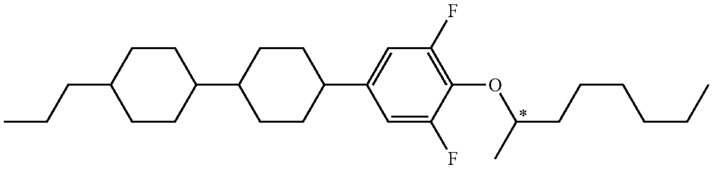
(Op-11)
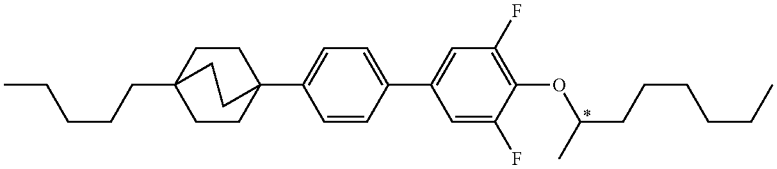
(Op-12)
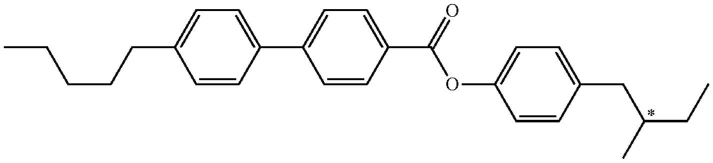
(Op-13)
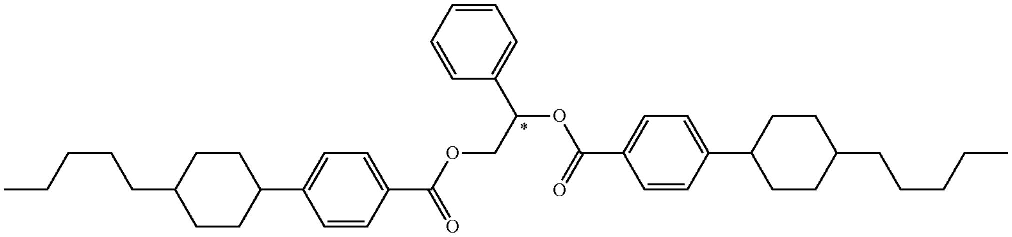
(Op-14)
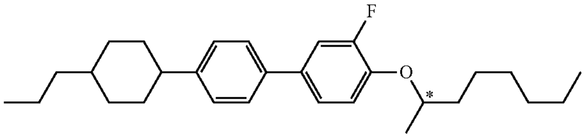
(Op-15)
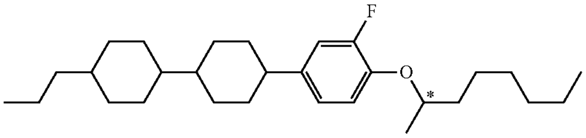
(Op-16)
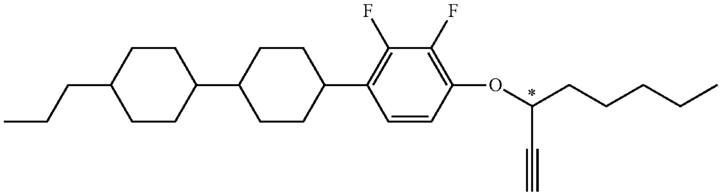

-continued (Op-17)

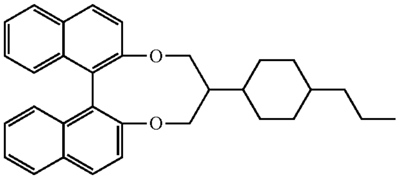

(Op-18)

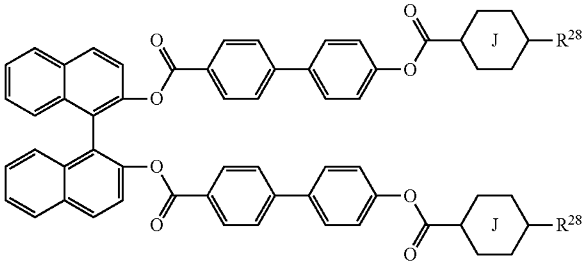

The antioxidant is effective in order to maintain a large voltage holding ratio. Specific preferred examples of the antioxidants include compounds (AO-1) and (AO-2) described below, IRGANOX 415, IRGANOX 565, IRGANOX 1010, IRGANOX 1035, IRGANOX 3114 and IRGANOX 1098 (trade name: BASF SE). The ultraviolet light absorber is effective in preventing a decrease in the maximum temperature. Preferred examples of the ultraviolet light absorbers include a benzophenone derivative, a benzoate derivative and a triazole derivative. Specific examples include compounds (AO-3) and (AO-4) described below, TINUVIN 329, TINUVIN P, TINUVIN 326, TINUVIN 234, TINUVIN 213, TINUVIN 400, TINUVIN 328 and TINUVIN99-2 (trade name: BASF SE) and 1,4-diazabicyclo[2.2.2]octane (DABCO). A light stabilizer such as an amine having steric hindrance is also preferred in order to maintain a large voltage holding ratio. Specific preferred examples of the light stabilizers include compounds (AO-5) and (AO-6) described below, TINUVIN 144, TINUVIN 765 and TINUVIN 770DF (trade name: BASF SE). Moreover, the heat stabilizer is also effective in order to maintain a large voltage holding ratio, and specific preferred examples include IRGAFOS 168 (trade name: BASF SE). The antifoaming agent is effective in order to prevent foam formation. Preferred examples of the antifoaming agent include dimethyl silicone oil and methylphenyl silicone oil.

(AO-1)

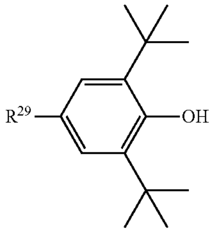

(AO-2)

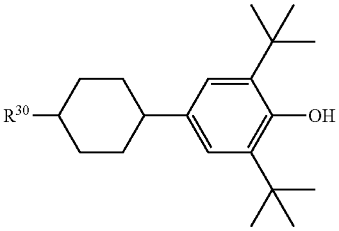

-continued (AO-3)

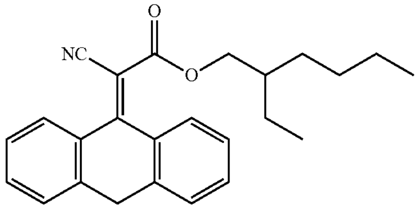

(AO-4)

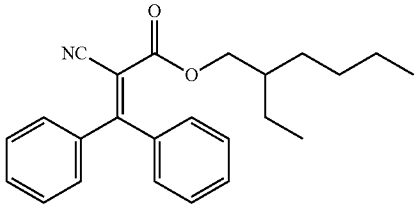

(AO-5)

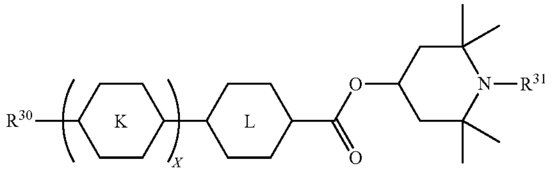

(AO-6)

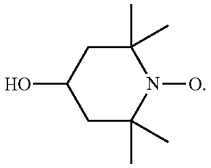

In compound (AO-1), $R^{29}$ is alkyl having 1 to 20 carbons, alkoxy having 1 to 20 carbons, $-COOR^{32}$ or $-CH_2CH_2COOR^{32}$, and $R^{32}$ is alkyl having 1 to 20 carbons herein. In compounds (AO-2) and (AO-5), $R^{30}$ is alkyl having 1 to 20 carbons. In compound (AO-5), $R^{31}$ is hydrogen, methyl or O. (oxygen radical), ring K and ring L are 1,4-cyclohexylene or 1,4-phenylene, and x is 0, 1 or 2.

4. Liquid Crystal Composite

Compound (1) has high polymerization reactivity, a high conversion ratio and high solubility in the liquid crystal composition. A liquid crystal composite is formed by polymerizing the polymerizable composition containing compound (1) and the liquid crystal composition. Compound (1) forms a polymer in the liquid crystal composition by polymerization of the composition. The polymer is effective in generating pretilt in the liquid crystal molecules. The polymerization is preferably performed at temperature at which the polymerizable composition exhibits the liquid crystal phase. The polymerization progresses by heat, light or the like. A preferred reaction includes photopolymerization. The photopolymerization is preferably performed at 100° C. or lower in order to prevent simultaneous occurrence of thermopolymerization. The polymerization may be allowed in a state in which an electric field or a magnetic field is applied.

The polymerization reactivity and the conversion ratio of compound (1) can be adjusted. Compound (1) is suitable for radical polymerization. An amount of remaining compound (1) can be reduced by optimizing reaction temperature. Compound (1) can be rapidly polymerized by adding the polymerization initiator. Examples of a photoradical polymerization initiator include TPO, and 1173 and 4265 from Darocur series of Ciba Specialty Chemicals Inc., and 184, 369, 500, 651, 784, 819, 907, 1300, 1700, 1800, 1850 and 2959 from Irgacure series thereof.

Additional examples of the photoradical polymerization initiator include 4-methoxyphenyl-2,4-bis(trichloromethyl) triazine, 2-(4-butoxystyryl)-5-trichloromethyl-1,3,4-oxadiazole, 9-phenylacridine, 9,10-benzphenazine, a benzophenone-Michler's ketone mixture, a hexaarylbiimidazole-mercaptobenzimidazole mixture, 1-(4-isopropylphenyl)-2-hydroxy-2-methylpropane-1-one, benzyl dimethyl ketal, 2-methyl-1-[4-(methylthio)phenyl]-2-morpholinopropane-1-one, a 2,4-diethylxanthone-methyl p-dimethylaminobenzoate mixture and a benzophenone-methyltriethanolamine mixture.

The polymerization can be performed by adding the photoradical polymerization initiator to the polymerizable composition, and then irradiating the resulting mixture with ultraviolet light in a state in which the electric field is applied. However, an unreacted polymerization initiator or a decomposition product of the polymerization initiator might cause poor display to the device, such as image sticking. In order to prevent such a poor display, photopolymerization may be performed without adding the polymerization initiator. A preferred wavelength of irradiating light is in the range from approximately 150 nanometers to approximately 500 nanometers. A further preferred wavelength is in the range from approximately 250 nanometers to approximately 450 nanometers, and a most preferred wavelength is in the range from approximately 300 nanometers to approximately 400 nanometers.

When storing the polymerizable compound, the polymerization inhibitor may be added thereto in order to inhibit the polymerization. The polymerizable compound is ordinarily added to the composition without removing the polymerization inhibitor. Examples of the polymerization inhibitor include hydroquinone, a hydroquinone derivative such as methylhydroquinone, 4-tert-butylcatechol, 4-methoxyphenol and phenothiazine.

5. Liquid Crystal Display Device

An effect of the polymer in the liquid crystal display device is interpreted as described below. The polymerizable composition is a mixture of the liquid crystal compound, the polymerizable compound and so forth. Application of the electric field to the composition causes alignment of the liquid crystal molecules in the direction of the electric field. The polymerizable compound is also aligned according to the alignment. The polymerizable compound is polymerized by irradiating the composition with ultraviolet light, while maintaining the alignment, to form three-dimensional network structure. Even when the electric field is removed, the alignment of the polymer is maintained. The liquid crystal molecules are stabilized in a state of being aligned in the direction of the electric field by the effect of the polymer. Accordingly, a response time of the device is to be shortened.

The polymerizable composition is preferably polymerized in the display device. One example is as described below. A display device having two glass substrates provided with transparent electrodes and an alignment film is arranged. A polymerizable composition containing compound (1), a liquid crystal composition, an additive and so forth as a component is prepared. The composition is injected into the display device. The display device is irradiated with ultraviolet light while applying the electric field to polymerize compound (1). A liquid crystal composite is formed by the polymerization. A liquid crystal display device having the liquid crystal composite can be easily produced by the method. Rubbing treatment to the alignment film may be omitted in the method. In addition, a method for stabilizing the liquid crystal molecules in a state without the electric field may be adopted.

When the amount of addition of the polymer is the range from approximately 0.1% by weight to approximately 2% by weight based on the liquid crystal composition, a liquid crystal display device having a PSA mode is prepared. The device having the PSA mode can be driven by a driving mode such as active matrix (AM) and passive matrix (PM). Such a device can be applied to any mode of a reflective mode, a transmissive mode and a transflective mode. An increase in the amount of addition of the polymer also allows preparation of a device having a polymer dispersed mode.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLES

The invention will be described in more detail by way of Examples.

The invention is not restricted by the Examples.

1. Example of Compound (1)

Compound (1) was synthesized by procedures presented in Example 1 or the like. The compound synthesized was identified by a method such as an NMR analysis. Physical properties of the compound were measured by methods described below.

NMR Analysis

As a measuring apparatus, DRX-500 (made by Bruker BioSpin Corporation) was used. In measurement of $^{1}H$-NMR, a sample was dissolved in a deuterated solvent such as $CDCl_3$, and measurement was carried out under the conditions of room temperature, 500 MHz and 16 times of accumulation. Tetramethylsilane was used as an internal standard. In measurement of $^{19}F$-NMR, $CFCl_3$ was used as an internal standard, and measurement was carried out under the conditions of 24 times of accumulation. In the explanation of a nuclear magnetic resonance spectrum, s, d, t, q, quin, sex, m and br stand for a singlet, a doublet, a triplet, a quartet, a quintet, a sextet, a multiplet and being broad, respectively.

HPLC Analysis

As a measuring apparatus, Prominence (LC-20AD; SPD-20A) made by Shimadzu Corporation was used. As a column, YMC-Pack ODS-A (length 150 mm, bore 4.6 mm, particle diameter 5 μm) made by YMC Co., Ltd. was used. As an eluate, acetonitrile and water were appropriately mixed and used. As a detector, a UV detector, an RI detector and a CORONA detector or the like was appropriately used. When the UV detector was used, a detection wavelength was set at 254 nanometers. A sample was dissolved in acetonitrile to prepare a solution having 0.1% by weight, and 1 microliter of the solution obtained was introduced into a sample injector. As a recorder, C-R7Aplus made by Shimadzu Corporation was used.

Ultraviolet-Visible Spectrophotometry

As a measuring apparatus, PharmaSpec UV-1700 made by Shimadzu Corporation was used. A detection wavelength was adjusted in the range from 190 nanometers to 700 nanometers. A sample was dissolved in acetonitrile and prepared to be a solution having 0.01 millimole per liter, and measurement was carried out by putting the solution in a quartz cell (optical path length 1 cm).

Sample for Measurement

When measuring phase structure and transition temperature (a clearing point, a melting point, polymerization starting temperature, or the like), a compound itself was used as a sample. When measuring physical properties such as a maximum temperature of a nematic phase, viscosity, optical anisotropy and dielectric anisotropy, a mixture of a compound and a base liquid crystal was used as a sample.

Measurement Method

Physical properties were measured by methods described below. Most of the measurement methods are applied as described in the Standard of the Japan Electronics and Information Technology Industries Association (JEITA) (JEITA ED-2521B) discussed and established by JEITA, or modified thereon. No thin film transistor (TFT) was attached to a TN device used for measurement.

(1) Phase Structure

A sample was placed on a hot plate in a melting point apparatus equipped with a polarizing microscope (FP-52 Hot Stage made by Mettler-Toledo International Inc.), a state of phase and a change thereof were observed by the polarizing microscope while heating the sample at a rate of 3° C. per minute, and a type of phase was specified.

(2) Transition Temperature (° C.)

Measurement was carried out using a differential scanning calorimeter, Diamond DSC System, made by PerkinElmer, Inc., or a high-sensitivity differential scanning calorimeter, X-DSC7000, made by SII NanoTechnology Inc. A sample was heated and then cooled at a rate of 3° C. per minute, and a starting point of an endothermic peak or an exothermic peak caused by a phase change of the sample was determined by extrapolation, and thus a transition temperature was determined. A melting point and a polymerization starting temperature of the compound were also measured using the apparatus. Temperature at which a compound transits from a solid to a liquid crystal phase such as a smectic phase and a nematic phase may be occasionally abbreviated as "minimum temperature of the liquid crystal phase." Temperature at which a compound transits from the liquid crystal phase to a liquid may be occasionally abbreviated as "clearing point."

The crystal was expressed as C. When kinds of the crystals were further distinguishable, each of the crystals was expressed as C, or $C_2$. The smectic phase was expressed as S and the nematic phase as N. When smectic A phase, smectic B phase, smectic C phase or smectic F phase was distinguishable among the smectic phases, the phases were expressed as $S_A$, $S_B$, $S_C$ or $S_F$, respectively. A liquid (isotropic) was expressed as I. The transition temperature was expressed, for example, as "C 50.0 N 100.0 I." The expression shows that a transition temperature from the crystal to the nematic phase is 50.0° C., and a transition temperature from the nematic phase to the liquid is 100.0° C.

(3) Maximum Temperature of a Nematic Phase ($T_{NI}$ or NI; ° C.)

A sample was placed on a hot plate in a melting point apparatus equipped with a polarizing microscope and was heated at a rate of 1° C. per minute. Temperature was measured when part of the sample began to change from a nematic phase to an isotropic liquid. A higher limit of a temperature range of the nematic phase may be occasionally abbreviated as "maximum temperature." When the sample was a mixture of a compound and a base liquid crystal, the maximum temperature was expressed using a symbol $T_{NI}$. When the sample was a mixture of a compound and component B, C, D or E, the maximum temperature was expressed using a symbol NI.

(4) Minimum Temperature of a Nematic Phase (Tc; ° C.)

Samples each having a nematic phase were kept in freezers at temperatures of 0° C., −10° C., −20° C., −30° C. and −40° C. for 10 days, and then liquid crystal phases were observed. For example, when a sample maintained the nematic phase at −20° C. and changed to crystals or a smectic phase at −30° C., $T_c$ was expressed as $T_c \leq -20°$ C. A lower limit of the temperature range of the nematic phase may be occasionally abbreviated as "minimum temperature."

(5) Viscosity (Bulk Viscosity; η; Measured at 20° C.; mPa·s)

A cone-plate (E-type) rotational viscometer made by Tokyo Keiki Co., Ltd was used for measurement.

(6) Optical Anisotropy (Refractive Index Anisotropy; Δn; Measured at 25° C.; Δn)

Measurement was carried out by an Abbe refractometer with a polarizing plate mounted on an ocular by using light at a wavelength of 589 nanometers. A surface of a main prism was rubbed in one direction, and then a sample was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of refractive index anisotropy (Δn) was calculated from an equation: $\Delta n = n\| - n\perp$.

(7) Specific Resistance (ρ; Measured at 25° C.; Ωcm)

Into a vessel provided with electrodes, 1.0 mL of sample was injected. Direct current voltage (10 V) was applied to the vessel, and a direct current after 10 seconds was measured. The specific resistance was calculated from an expression described below.

(Specific resistance)={(voltage)×(electric capacity of a vessel)}/{(direct current)×(dielectric constant of vacuum)}.

(8) Voltage Holding Ratio (VHR-1; Measured at 25° C.; %)

A TN device used for measurement had a polyimide alignment film and a distance (cell gap) between two glass substrates was 5 micrometers. A sample was put in the device, and then the device was sealed with an ultraviolet-curable adhesive. The device was charged by applying pulse voltage (60 microseconds at 5 V). A decaying voltage was measured for 16.7 milliseconds with a high-speed voltmeter, and area A between a voltage curve and a horizontal axis in a unit cycle was determined. Area B was an area without decay. A voltage holding ratio is expressed in terms of a percentage of area A to area B.

(9) Voltage Holding Ratio (VHR-2; Measured at 80° C.; %)

A voltage holding ratio was measured in procedures identical with the procedures described above except that the voltage holding ratio was measured at 80° C. in place of 25° C. The results obtained were presented using a symbol of VHR-2.

Methods for measuring physical properties may be occasionally different between a sample having positive dielectric anisotropy and a sample having negative dielectric anisotropy. Measurement methods when dielectric anisotropy is positive are described in sections (10a) to (14a). When the dielectric anisotropy is negative, the methods are described in sections (10b) to (14b).

(10a) Viscosity (Rotational Viscosity; γ1; Measured at 25° C.; mPa·s)

Positive dielectric anisotropy: Measurement was carried out according to a method described in M. Imai et al., Molecular Crystals and Liquid Crystals, Vol. 259, 37 (1995). A sample was put in a TN device in which a twist angle was 0 degrees and a distance (cell gap) between two glass substrates was 5 micrometers. Voltage was stepwise applied to the device in the range from 16 V to 19.5 V at an increment of 0.5 V. After a period of 0.2 second with no voltage application, application was repeated under conditions of only one of rectangular waves (rectangular pulse; 0.2 second) and no application (2 seconds). A peak current and a peak time of a transient current generated by the applied voltage were measured. A value of rotational viscosity was obtained from the measured values according to calculating equation (8) on page 40 of the paper presented by Imai et al. A value of dielectric anisotropy necessary for the calculation was determined by using the device used for measuring the rotational viscosity according to the method as described below.

(10b) Viscosity (Rotational Viscosity; γ1; Measured at 25° C.; mPa·s)

Negative dielectric anisotropy: Measurement was carried out according to a method described in M. Imai et al., Molecular Crystals and Liquid Crystals, Vol. 259, 37 (1995). A sample was put in a VA device in which a distance (cell gap) between two glass substrates was 20 micrometers. Voltage was applied stepwise to the device in the range of 39 V to 50 V at an increment of 1 V. After a period of 0.2 second with no voltage, application was repeated under conditions of only one of rectangular waves (rectangular pulse; 0.2 second) and no voltage (2 seconds). A peak current and a peak time of a transient current generated by the applied voltage were measured. A value of rotational viscosity was obtained from the measured values according to calculating equation (8) on page 40 of the paper presented by M. Imai et al. As dielectric anisotropy required for the calculation, a value measured in a section of dielectric anisotropy described below was used.

(11a) Dielectric Anisotropy (Δ∈; Measured at 25° C.)

Positive dielectric anisotropy: A sample was put in a TN device in which a distance (cell gap) between two glass substrates was 9 micrometers and a twist angle was 80 degrees. Sine waves (10 V, 1 kHz) were applied to the device, and after 2 seconds, a dielectric constant (∈||) in the major axis direction of liquid crystal molecules was measured. Sine waves (0.5V, 1 kHz) were applied to the device, and after 2 seconds, a dielectric constant (∈⊥) in the minor axis direction of the liquid crystal molecules was measured. A value of dielectric anisotropy was calculated from an equation: Δ∈=∈||−∈⊥.

(11b) Dielectric Anisotropy (Δ∈; Measured at 25° C.)

Negative dielectric anisotropy: A value of dielectric anisotropy was calculated from an equation: Δ∈=∈||−∈⊥. A dielectric constant (∈|| and ∈⊥) was measured as described below.

(1) Measurement of dielectric constant (∈||): An ethanol (20 mL) solution of octadecyl triethoxysilane (0.16 mL) was applied to a well-cleaned glass substrate. The glass substrate was rotated with a spinner, and then heated at 150° C. for 1 hour. A sample was put in a VA device in which a distance (cell gap) between two glass substrates was 4 micrometers, and the device was sealed with an ultraviolet-curable adhesive. Sine waves (0.5 V, 1 kHz) were applied to the device, and after 2 seconds, a dielectric constant (∈||) in the major axis direction of liquid crystal molecules was measured.

(2) Measurement of dielectric constant (∈⊥): A polyimide solution was applied to a well-cleaned glass substrate. After calcining the glass substrate, rubbing treatment was applied to the alignment film obtained. A sample was put in a TN device in which a distance (cell gap) between two glass substrates was 9 micrometers and a twist angle was 80 degrees. Sine waves (0.5 V, 1 kHz) were applied to the device, and after 2 seconds, a dielectric constant (∈⊥) in the minor axis direction of the liquid crystal molecules was measured.

(12a) Elastic Constant (K; Measured at 25° C.; pN)

Positive dielectric anisotropy: HP4284A LCR Meter made by Yokogawa-Hewlett-Packard Co. was used for measurement. A sample was put in a horizontal alignment device in which a distance (cell gap) between two glass substrates was 20 micrometers. An electric charge from 0 V to 20 V was applied to the device, and electrostatic capacity and applied voltage were measured. Measured values of the electrostatic capacity (C) and the applied voltage (V) were fitted to equation (2.98) and equation (2.101) on page 75 of "Liquid Crystal Device Handbook" (Ekisho Debaisu Handobukku in Japanese) (The Nikkan Kogyo Shimbun, Ltd.), and values of $K_{11}$ and $K_{33}$ were obtained from equation (2.99). Next, $K_{22}$ was calculated using the previously determined values of $K_{11}$ and $K_{33}$ in equation (3.18) on page 171. An elastic constant K is expressed using a mean value of the thus determined $K_{11}$, $K_{22}$ and $K_{33}$.

(12b) Elastic Constant ($K_{11}$ and $K_{33}$; Measured at 25° C.; pN)

Negative dielectric anisotropy: Elastic Constant Measurement System Model EC-1 made by TOYO Corporation was used for measurement. A sample was put in a vertical alignment device in which a distance (cell gap) between two glass substrates was 20 micrometers. An electric charge of 20 V to 0 V was applied to the device, and electrostatic capacity and applied voltage were measured. Values of electrostatic capacity (C) and applied voltage (V) were fitted to equation (2.98) and equation (2.101) on page 75 of "Liquid Crystal Device Handbook (Ekisho Debaisu Handobukku, in Japanese)" (The Nikkan Kogyo Shimbun, Ltd.), and a value of elastic constant was obtained from equation (2.100).

(13a) Threshold Voltage (Vth; Measured at 25° C.; V)

Positive dielectric anisotropy: An LCD-5100 luminance meter made by Otsuka Electronics Co., Ltd. was used for measurement. A light source was a halogen lamp. A sample was put in a normally white mode TN device in which a distance (cell gap) between two glass substrates was 0.45/Δn (μm) and a twist angle was 80 degrees. Voltage (32 Hz, rectangular waves) to be applied to the device was stepwise increased from 0 V to 10 V at an increment of 0.02 V. On the occasion, the device was irradiated with light from a direction perpendicular to the device, and an amount of light transmitted through the device was measured. A voltage-transmittance curve was prepared, in which the maximum amount of light corresponds to 100% transmittance and the minimum amount of light corresponds to 0% transmittance. A threshold voltage is expressed in terms of a voltage at 90% transmittance.

(13b) Threshold Voltage (Vth; Measured at 25° C.; V)

Negative dielectric anisotropy: An LCD-5100 luminance meter made by Otsuka Electronics Co., Ltd. was used for measurement. A light source was a halogen lamp. A sample was put in a normally black mode VA device in which a distance (cell gap) between two glass substrates was 4 micrometers and a rubbing direction was anti-parallel, and the device was sealed with an ultraviolet-curable adhesive. Voltage (60 Hz, rectangular waves) applied to the device was increased stepwise from 0 V to 20 V at an increment of 0.02 V. On the occasion, the device was irradiated with light from a direction perpendicular to the device, and an amount of light transmitted through the device was measured. A voltage-transmittance curve was prepared, in which the maximum value of the amount of light corresponded to 100% transmittance and the minimum value of the amount of light corresponded to 0% transmittance. A threshold voltage is expressed in terms of a voltage at 10% transmittance.

(14a) Response Time (τ; Measured at 25° C.; ms)

Positive dielectric anisotropy: An LCD-5100 luminance meter made by Otsuka Electronics Co., Ltd. was used for measurement. A light source was a halogen lamp. A low-pass filter was set to 5 kHz. A sample was put in a normally white mode TN device in which a distance (cell gap) between two glass substrates was 5.0 micrometers and a twist angle was 80 degrees. Rectangular waves (60 Hz, 5V, 0.5 second) were applied to the device. On the occasion, the device was irradiated with light from a direction perpendicular to the device, and an amount of light transmitted through the device was measured. Transmittance at a maximum was regarded to be 100%, and transmittance at a minimum was regarded to be 0%. A rise time (τr: rise time; millisecond) is a period of time required for the change in transmittance from 90% to 10%. A fall time (τf: fall time; millisecond) is a period of time required for the change in transmittance from 10% to 90%. The response time was expressed in terms of a sum of the rise time and the fall time thus obtained.

(14b) Response Time (τ; Measured at 25° C.; ms)

Negative dielectric anisotropy: An LCD-5100 luminance meter made by Otsuka Electronics Co., Ltd. was used for measurement. A light source was a halogen lamp. A low-pass filter was set to 5 kHz. A sample was put in a normally black mode PVA device in which a distance (cell gap) between two glass substrates was 3.2 micrometers and a rubbing direction was anti-parallel, and the device was sealed using an ultraviolet-curable adhesive. A voltage having a degree a little over a threshold voltage was applied to the device for 1 minute, and then the device was irradiated with ultraviolet light having 23.5 $mW/cm^2$ for 8 minutes while applying a voltage of 5.6 V. Rectangular waves (60 Hz, 10 V, 0.5 second) were applied to the device. On the occasion, the device was irradiated with light from a direction perpendicular to the device, and an amount of light transmitted through the device was measured. Transmittance at a maximum was regarded to be 100%, and transmittance at a minimum was regarded to be 0%. A response time was expressed in terms of a period of time required for the change in transmittance from 90% to 10% (fall time; millisecond).

Example 1

Synthesis of Compound (No. 1)

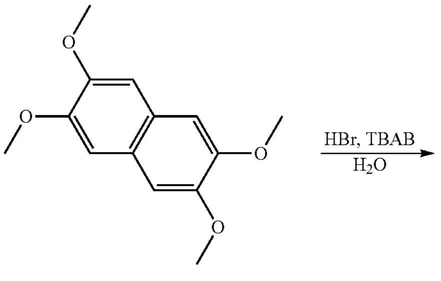

(T-1)

-continued

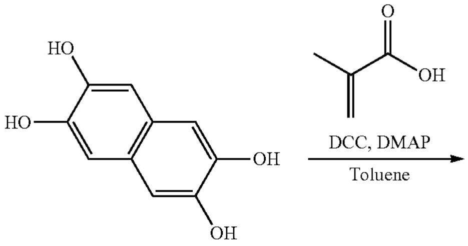

(T-2)

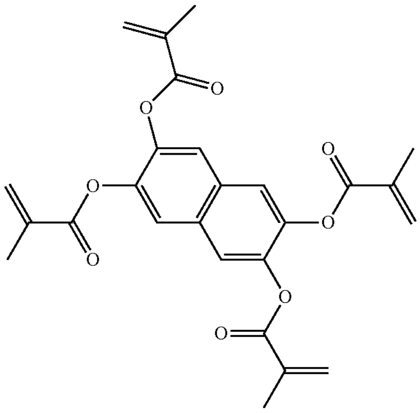

No. 1

First Step

Under a nitrogen atmosphere, compound (T-1) (10.0 g, 40.3 mmol) and tetrabutylammonium bromide (TBAB) (0.2 g, 18.4 mmol) were added to concentrated hydrobromic acid (100 mL), and the resulting mixture was heated and refluxed for 1 hour. The resulting reaction mixture was returned to 25° C., and then poured into ice water (100 mL). After adding zinc powder, filtration was performed. The resulting filtrate was concentrated to give compound (T-2) (7.7 g, 40.3 mmol, 100.0%).

Second Step

Under a nitrogen atmosphere, methacrylic acid (15.3 g, 177.2 mmol), dicyclohexylcarbodiimide (DCC) (36.6 g, 177.2 mmol) and N,N-dimethyl-4-aminopyridine (DMAP) (4.9 g, 40.3 mmol) were dissolved into toluene (200 ml) under ice-cooling. To the resulting solution, a toluene (30 mL) solution of compound (T-2) (7.7 g, 40.3 mmol) was added dropwise under ice-cooling, and the resulting mixture was stirred at 25° C. for 16 hours. After reaction completion, a formed insoluble matter was filtered off, the resulting filtrate was subjected to extraction with toluene, the combined organic layer was sequentially washed with water and a saturated aqueous solution of sodium chloride, and dried over anhydrous magnesium sulfate. The resulting solution was concentrated under reduced pressure, and the resulting residue was purified by silica gel chromatography (toluene:ethyl acetate=10:1 (volume ratio)). Further, the resulting product was purified by recrystallization from a mixed solvent of heptane and ethyl acetate (9:1 (volume ratio)) to give compound (No. 1) (11.8 g, 25.5 mmol, 63.2%).

$^1$H-NMR ($CDCl_3$; δ ppm): 7.84 (d, 2H), 7.48 (m, 2H), 6.50 (d, 2H), 6.35 (d, 2H), 5.88-5.87 (m, 2H), 5.78-5.77 (m, 2H), 2.13 (s, 6H), 2.06 (s, 6H).

Physical properties of compound (No. 1) were as described below. Melting point: 160.4° C., polymerization starting temperature: 167° C.

Example 2

Synthesis of Compound (No. 51)

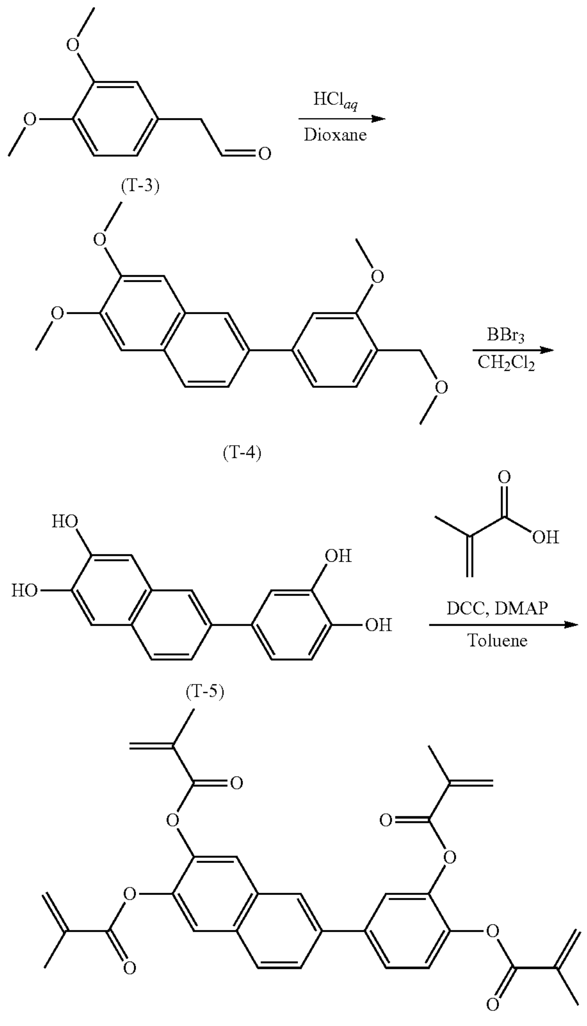

(T-3)

(T-4)

(T-5)

No. 51

First Step

Under a nitrogen atmosphere, compound (T-3) (5.0 g, 27.7 mmol) was dissolved into dioxane (60 mL). Then, 12 M hydrochloric acid (90 mL) was added thereto. The resulting mixture was stirred at 25° C. for 1 hour, and then the resulting reaction mixture was poured into water (100 mL). After a deposit was filtered off, the resulting filtrate was subjected to extraction with dimethyl ether. The combined organic layer was washed sequentially by water, a saturated aqueous solution of sodium hydrogencarbonate and a saturated aqueous solution of sodium chloride, and dried over anhydrous magnesium sulfate. The resulting solution was concentrated under reduced pressure, and the resulting residue was purified by silica gel chromatography (heptane:ethyl acetate=7:3 (volume ratio)) to give compound (T-4) (3.4 g, 10.6 mmol, 76.3%).

Second Step

Under a nitrogen atmosphere, compound (T-4) (3.4 g, 10.6 mmol) was dissolved into dichloromethane (35 mL). The resulting mixture was cooled to −60° C., and then boron tribromide (11.9 g, 47.7 mmol) was added dropwise thereto in the temperature range of −60° C. to −50° C., and the resulting mixture was further stirred for 1 hour. The resulting reaction mixture was returned to 25° C., and then further stirred for 16 hours. Then, the resulting reaction mixture was poured into water (100 mL). The resulting mixture was subjected to extraction with ethyl acetate, the combined organic layer was washed with water, and dried over anhydrous magnesium sulfate. The resulting solution was concentrated under reduced pressure to give compound (T-5) (2.8 g, 10.3 mmol, 97.2%).

Third Step

Under a nitrogen atmosphere, methacrylic acid (3.9 g, 45.3 mmol), dicyclohexylcarbodiimide (DCC) (9.4 g, 45.3 mmol) and N,N-dimethyl-4-aminopyridine (DMAP) (1.3 g, 10.3 mmol) were dissolved into toluene (100 mL) under ice-cooling. To the resulting solution, a toluene (20 mL) solution of compound (T-5) (2.8 g, 10.3 mmol) was added dropwise under ice-cooling, and the resulting mixture was stirred at 25° C. for 16 hours. After reaction completion, a formed insoluble matter was filtered off, the resulting filtrate was subjected to extraction with toluene, and the combined organic layer was washed sequentially with water and a saturated aqueous solution of sodium chloride, and dried over anhydrous magnesium sulfate. The resulting solution was concentrated under reduced pressure, and the resulting residue was purified by silica gel chromatography (toluene:ethyl acetate=10:1 (volume ratio)). Further, the resulting product was purified by recrystallization from a mixed solvent of heptane and ethyl acetate (9:1 (volume ratio)) to give compound (No. 51) (3.9 g, 7.3 mmol, 70.6%).

$^1H$-NMR ($CDCl_3$; δ ppm): 7.87 (d, 1H), 7.80 (s, 1H), 7.65 (d, 1H), 7.52-7.49 (m, 1H), 7.46-7.42 (m, 1H), 7.37-7.35 (m, 1H), 7.28-7.24 (m, 2H), 6.32 (s, 2H), 6.28 (s, 1H), 6.08 (s, 1H), 5.75-5.74 (m, 2H), 5.72 (m, 1H), 5.59 (m, 1H), 2.04 (s, 3H), 2.03 (s, 3H), 2.00 (s, 3H), 1.86 (s, 3H).

Physical properties of compound (No. 51) were as described below. Liquid at an ordinary temperature, and polymerization starting temperature: 248° C.

Example 3

Synthesis of Compound (No. 151)

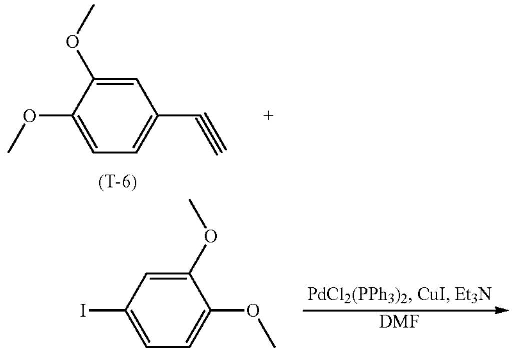

(T-6)

(T-7)

-continued

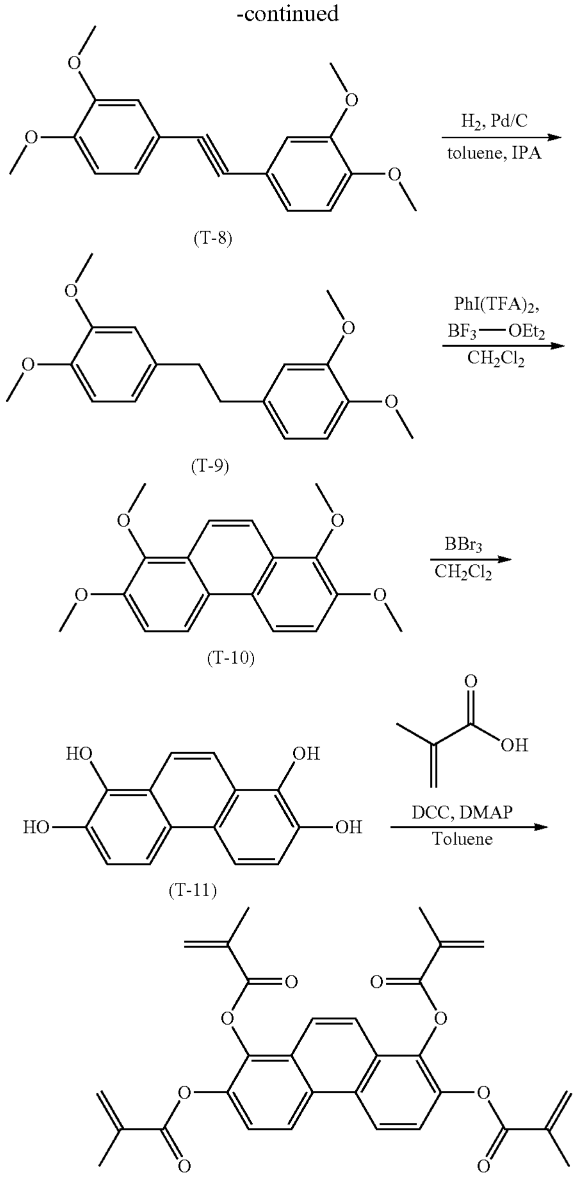

(T-8)

(T-9)

(T-10)

(T-11)

No. 151

First Step

Under a nitrogen atmosphere, compound (T-6) (5.0 g, 30.8 mmol), compound (T-7) (9.0 g, 33.9 mmol), triethylamine (9.4 g, 92.5 mmol), copper iodide (0.6 g, 3.1 mmol) and bistriphenylphosphinepalladium dichloride (1.1 g, 1.5 mmol) were dissolved into DMF (60 mL). The resulting reaction mixture was heated to 81° C., and stirred for 16 hours. The resulting reaction mixture was returned to 25° C., and then poured into water (100 mL). The resulting mixture was subjected to extraction with dichloromethane, and then the combined organic layer was washed sequentially with an aqueous solution of ammonium chloride and water, and dried over anhydrous magnesium sulfate. The resulting solution was concentrated under reduced pressure, and the resulting residue was purified by silica gel chromatography (cyclohexane: ethyl acetate=5:1 (volume ratio)) to give compound (T-8) (7.6 g, 25.5 mmol, 82.6%).

Second Step

Under a nitrogen atmosphere, compound (T-8) (7.6 g, 25.5 mmol) was dissolved into a mixed solvent of toluene (40 mL) and IPA (40 mL). Further, Pd/C (0.40 g) was added thereto, and the resulting mixture was stirred under a hydrogen atmosphere at room temperature until hydrogen was not absorbed any more. After reaction completion, Pd/C was removed, and a solvent was further distilled off. The resulting residue was purified by silica gel chromatography (cyclohexane:ethyl acetate=5:1 (volume ratio)) to give compound (T-9) (7.7 g, 25.4 mmol, 99.8%).

Third Step

Under a nitrogen atmosphere, bistrifluoroacetoxyiodobenzene (13.1 g, 30.5 mmol) and a boron trifluoride-diethyl ether complex (8.3 g, 58.4 mmol) were dissolved into dichloromethane (200 mL). The resulting mixture was cooled to −20° C., and then a dichloromethane solution (50 mL) of compound (T-9) (7.7 g, 25.4 mmol) was added dropwise thereto in the temperature range from −20° C. to −15° C., and the resulting mixture was further stirred for 40 minutes. The resulting reaction mixture was returned to 25° C., and then poured into water (200 mL). The resulting mixture was subjected to extraction with dichloromethane, and then the combined organic layer was washed with water, and then dried over anhydrous magnesium sulfate. The resulting solution was concentrated under reduced pressure, and the resulting residue was purified by recrystallization from a mixed solvent of heptane and ethyl acetate (9:1 (volume ratio)) to give compound (T-10) (6.0 g, 20.0 mmol, 78.9%).

Fourth Step

Under a nitrogen atmosphere, compound (T-10) (6.0 g, 20.0 mmol) was dissolved into dichloromethane (60 mL). The resulting mixture was cooled to −60° C., and then boron tribromide (22.5 g, 90.0 mmol) was added dropwise thereto in the temperature range from −60° C. to −50° C., and the resulting mixture was further stirred for 1 hour. The resulting reaction mixture was returned to 25° C., and then further stirred for 16 hours. Then, the resulting reaction mixture was poured into water (200 mL). The resulting mixture was subjected to extraction with ethyl acetate, and then the combined organic layer was washed with water and dried over anhydrous magnesium sulfate. The resulting solution was concentrated under reduced pressure to give compound (T-11) (4.8 g, 19.7 mmol, 98.5%).

Fifth Step

Under a nitrogen atmosphere, methacrylic acid (7.5 g, 86.7 mmol), dicyclohexylcarbodiimide (DCC) (17.9 g, 86.7 mmol) and N,N-dimethyl-4-aminopyridine (DMAP) (2.2 g, 19.7 mmol) were dissolved into toluene (200 mL) under ice-cooling. To the resulting solution, a toluene (20 mL) solution of compound (T-11) (4.8 g, 19.7 mmol) was added dropwise under ice-cooling, and the resulting mixture was stirred at 25° C. for 16 hours. After reaction completion, a formed insoluble matter was filtered off, the resulting filtrate was subjected to extraction with toluene, and the combined organic layer was washed sequentially with water and a saturated aqueous solution of sodium chloride, and then dried over anhydrous magnesium sulfate. The resulting solution was concentrated under reduced pressure, and the resulting residue was purified by silica gel chromatography (toluene: ethyl acetate=10:1 (volume ratio)). Further, the resulting product was purified by recrystallization from a mixed solvent of heptane and ethyl acetate (9:1 (volume ratio)) to give compound (No. 151) (6.5 g, 12.5 mmol, 63.7%).

$^1$H-NMR ($CDCl_3$; δ ppm): 8.40 (s, 2H), 7.80 (s, 2H), 7.71 (s, 2H), 6.36 (d, 4H), 5.79-5.77 (m, 4H), 2.07-2.06 (m, 12H).

Physical properties of compound (No. 151) were as described below. Melting point: 134.1° C., polymerization starting temperature: 148° C.

Comparative Example 1

For a comparison, comparative compound (R-1) was synthesized.

(R-1)

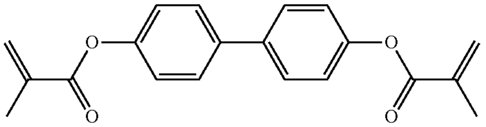 [SMILES: C=C(C)C(=O)Oc1ccc(-c2ccc(OC(=O)C(=C)C)cc2)cc1]

1H-NMR (DMSO-d; δ ppm): 7.24 (d, 4H), 6.96 (d, 4H), 6.41 (d, 2H), 6.26 (d, 2H), 1.98 (s, 6H).

Physical properties of compound (R-1) were as described below. Melting point: 150° C., polymerization starting temperature: 152° C.

Example 4

Comparative Experiments 1

Unreacted Polymerizable Compound

To liquid crystal composition A described below, polymerizable compound (No. 1) was added at a ratio of 0.3% by weight and dissolved thereinto. The resulting polymerizable composition was irradiated with ultraviolet light of 75 $mW/cm^2$ for 200 seconds (15,000 mJ). A mercury-xenon lamp, EXECURE4000-D, made by HOYA CANDEO OPTRONICS Corporation was used for irradiation with ultraviolet light. An amount of remaining polymerizable compound in the resulting liquid crystal composite was measured by HPLC. The results are summarized in Table 1 collectively with the results obtained by irradiation with ultraviolet light for 400 seconds (30,000 mJ). Meanwhile, an unreacted material was also measured on comparative compound (R-2) in a similar manner. The results are summarized in Table 1.

Components of liquid crystal composition A were as described below.

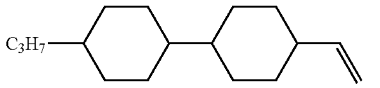

28 wt %

-continued

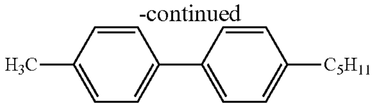

11 wt %

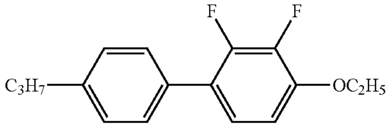

13 wt %

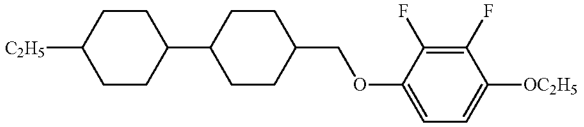

18 wt %

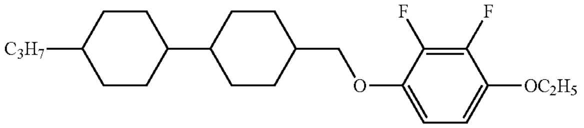

16 wt %

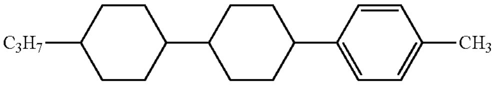

4 wt %

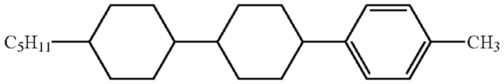

4 wt %

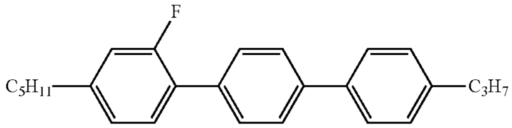

6 wt %

TABLE 1

| Amount of unreacted material | | | |
|---|---|---|---|
| Polymerizable | | Unreacted material (% by weight) | |
| compound | Structural formula | 15,000 mJ | 30,000 mJ |
| No. 1 | 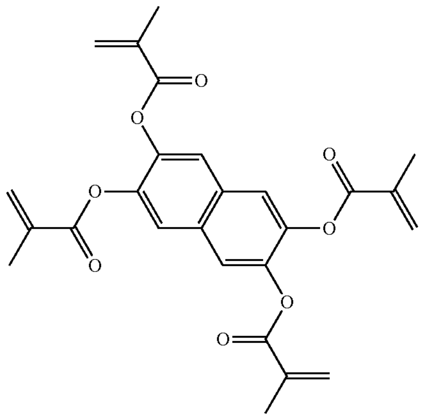 | 80.2 | 66.1 |

TABLE 1-continued

| Amount of unreacted material | | | |
|---|---|---|---|
| Polymerizable | | Unreacted material (% by weight) | |
| compound | Structural formula | 15,000 mJ | 30,000 mJ |
| Comparative compound (R-1) | 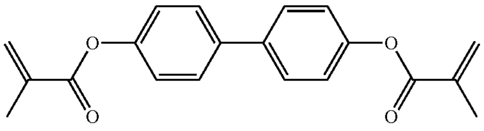 | 90.5 | 88.9 |

Table 1 shows that the amount of unreacted material remained in the liquid crystal composite is smaller in the case of compound (No. 1). Therefore, the polymerizable compound in the invention is concluded to have a larger conversion ratio in comparison with a conventional compound.

Example 5

Compound (No. 1) to compound (No. 199) shown below can be synthesized with reference to the experimental operations described in Example 1 and "2. Synthesis method."

No.1

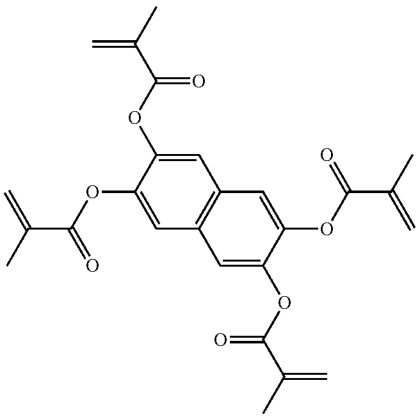

No.2

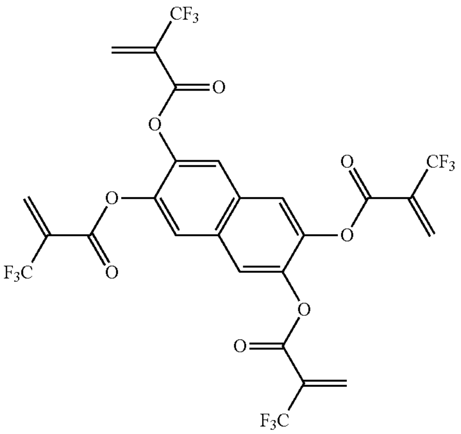

No.3

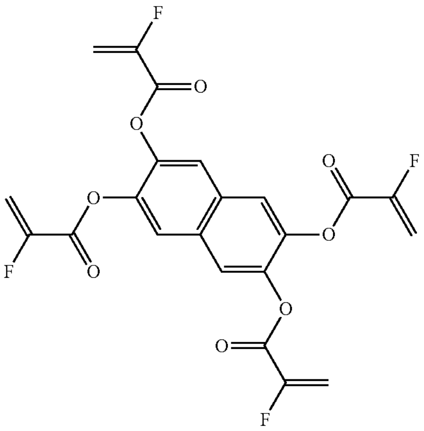

No.4

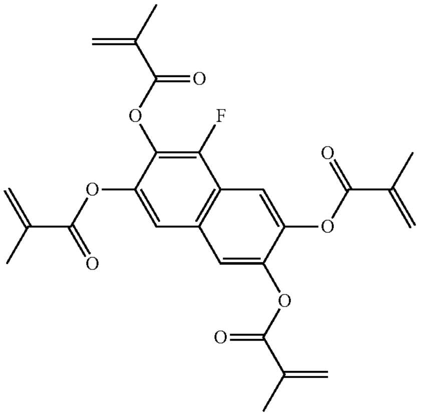

-continued
No.5
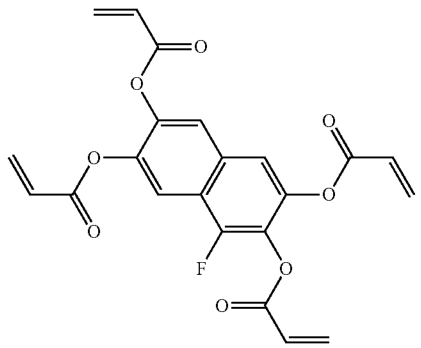
No.6
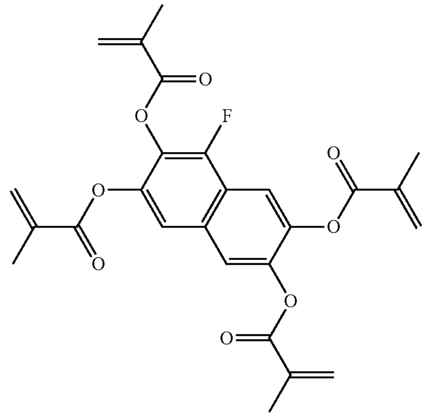
No.7
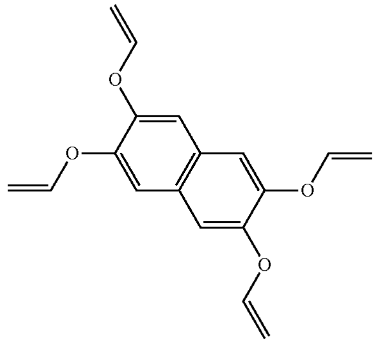
No.8
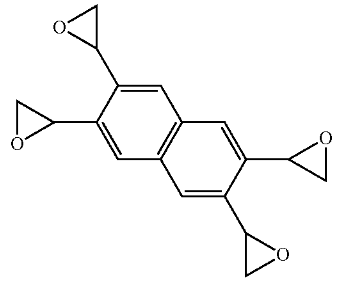
No.9
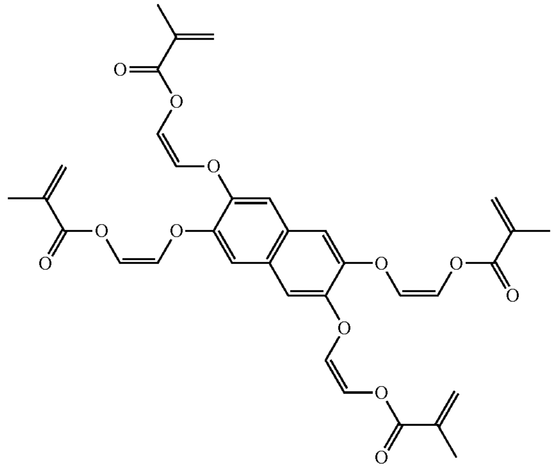
No.10
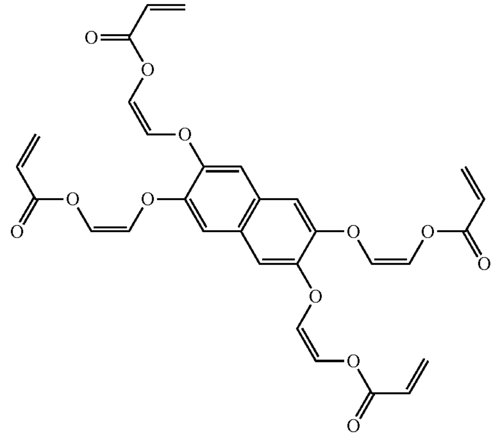

-continued
No.11
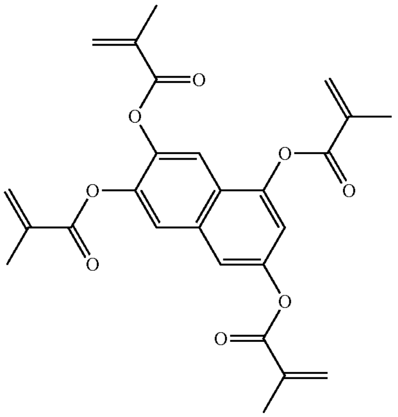
No.12
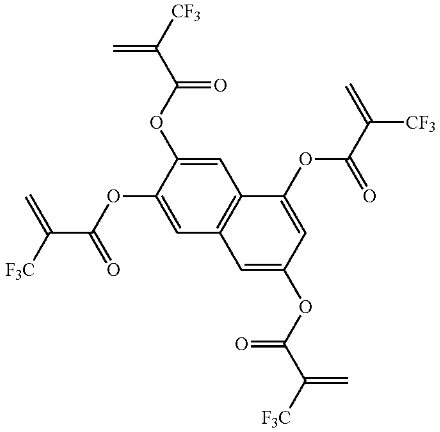
No.13
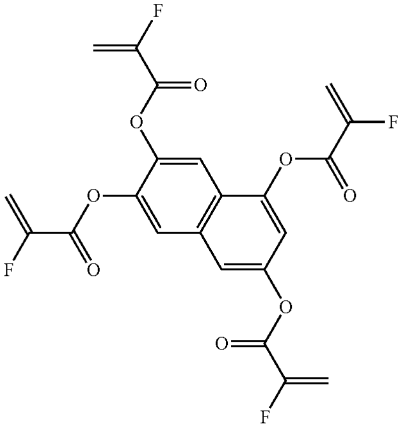
No.14
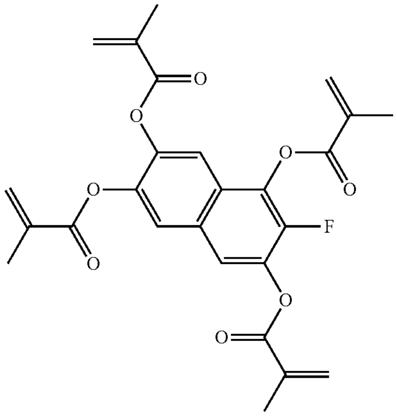
No.15
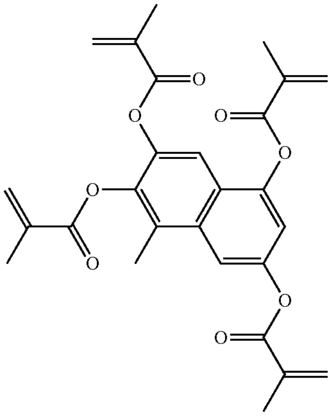
No.16
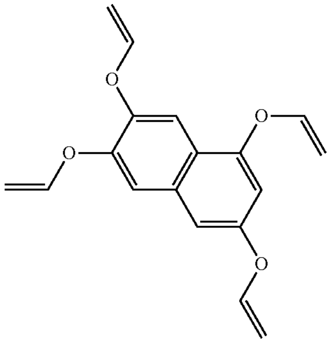

-continued
No.17
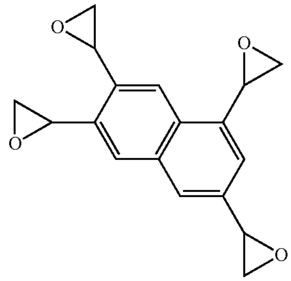
No.18
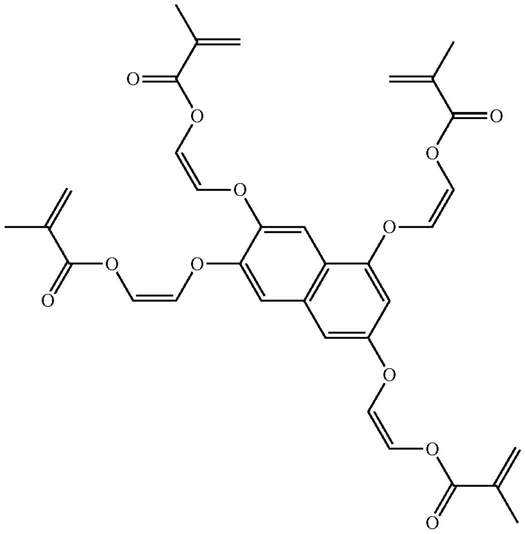
No.19
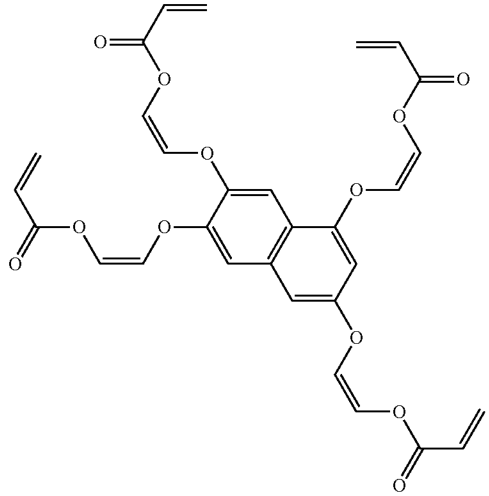
No.20
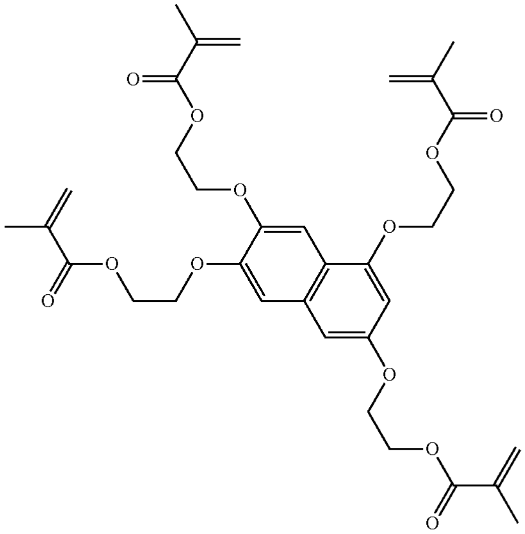
No.21
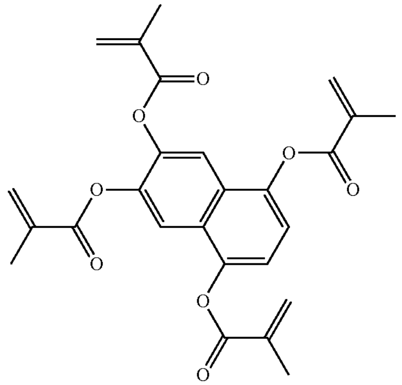
No.22
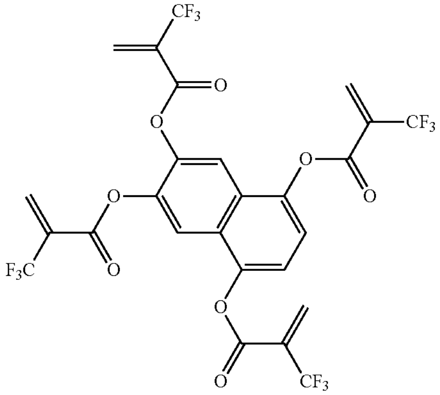

-continued
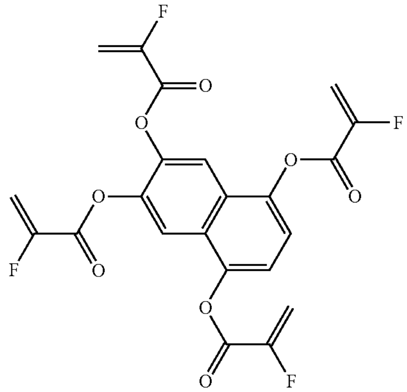
No.23
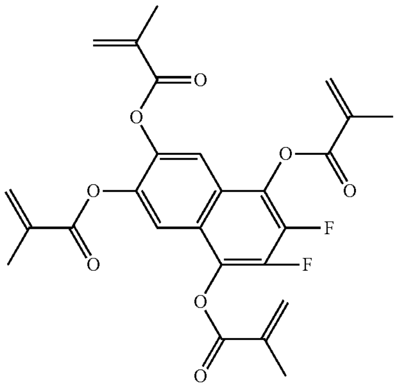
No.24
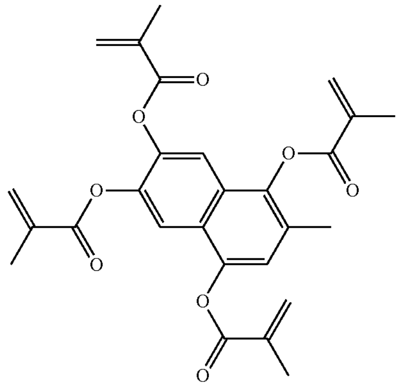
No.25
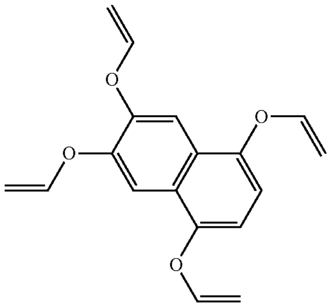
No.26
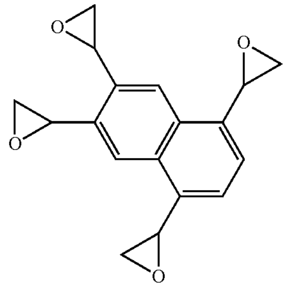
No.27
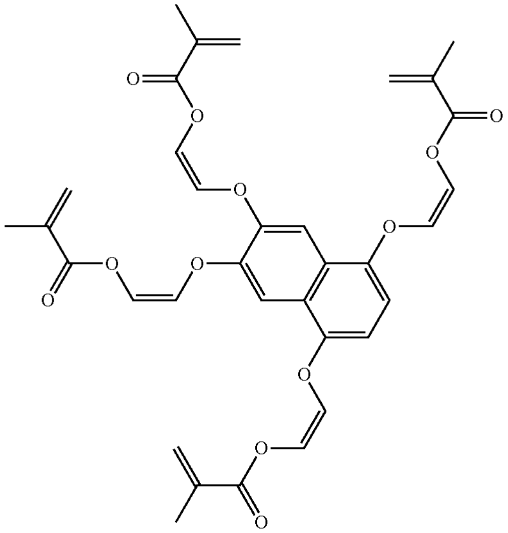
No.28

-continued
No.29
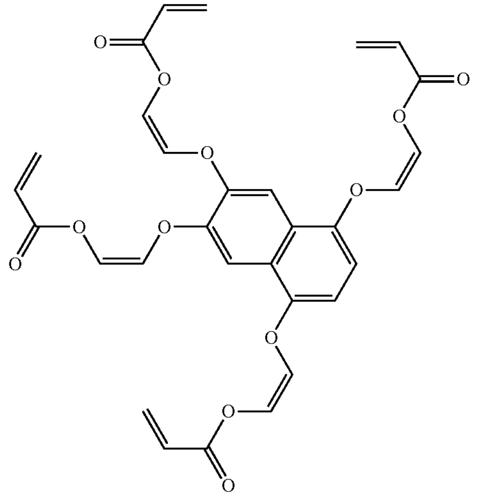
No.30
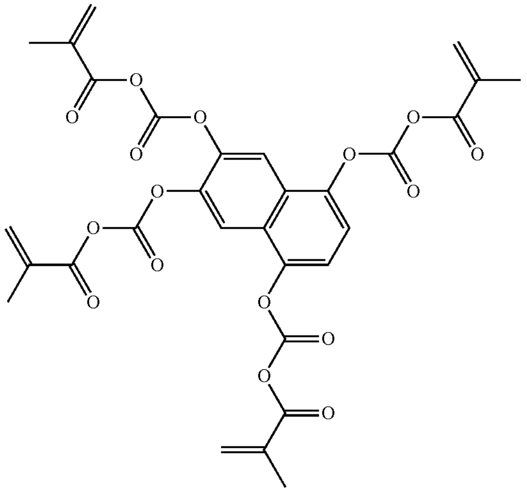
No.31
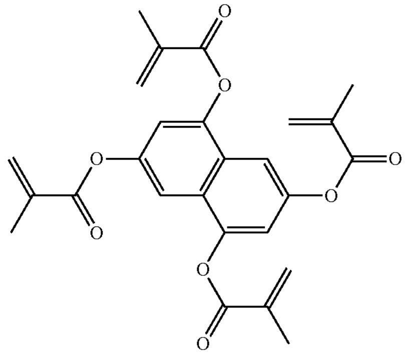
No.32
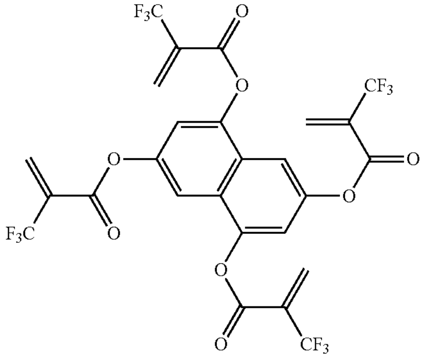
No.33
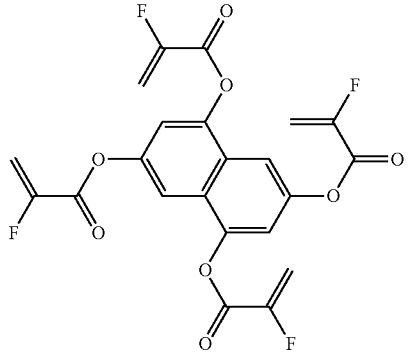
No.34
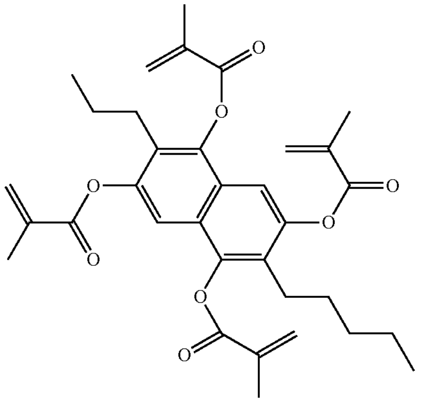
No.35
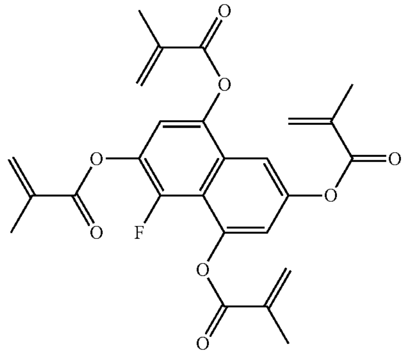
No.36
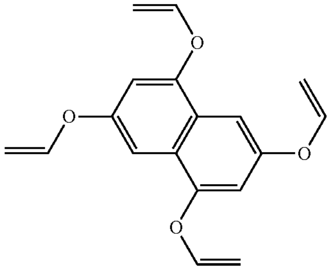

-continued
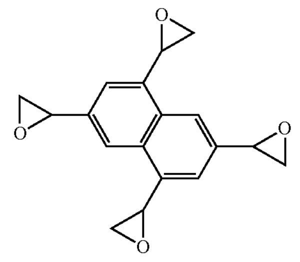
No.37
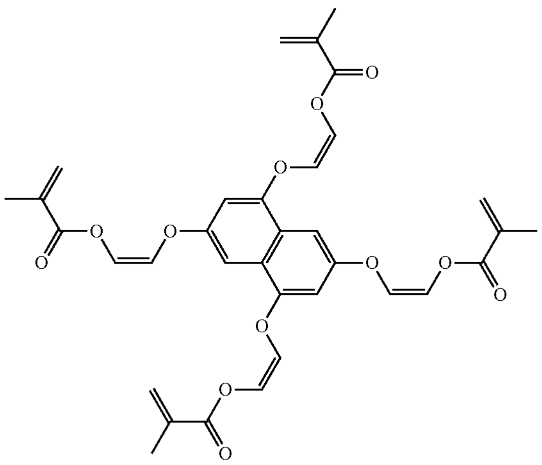
No.38
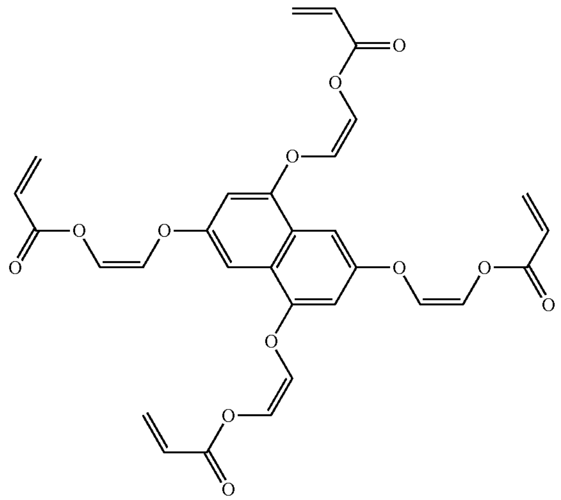
No.39
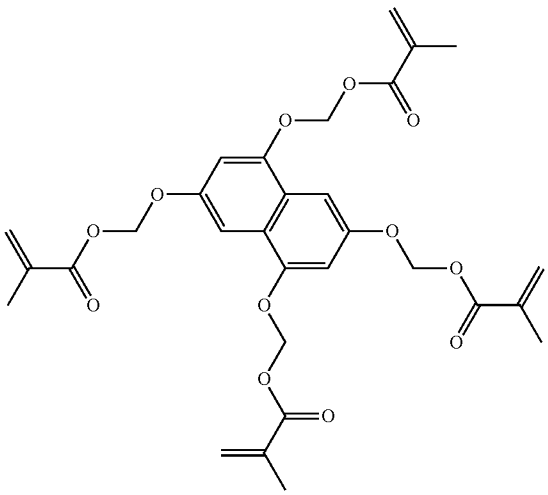
No.40
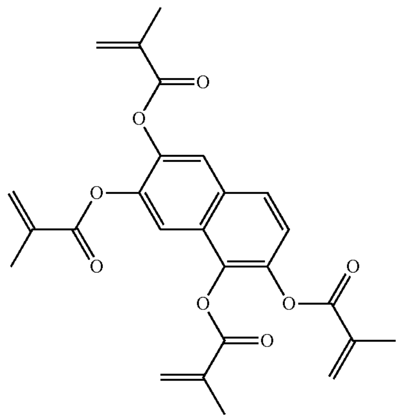
No.41
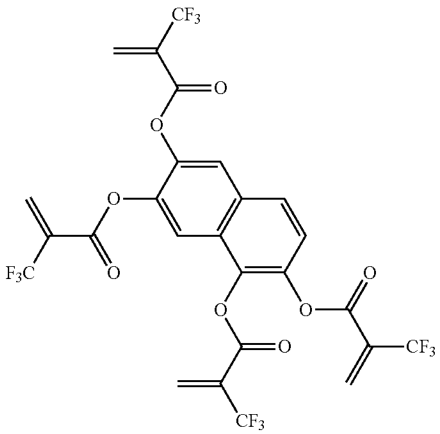
No.42

-continued
No.43
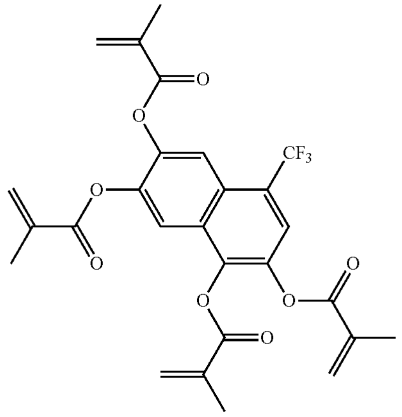
No.44
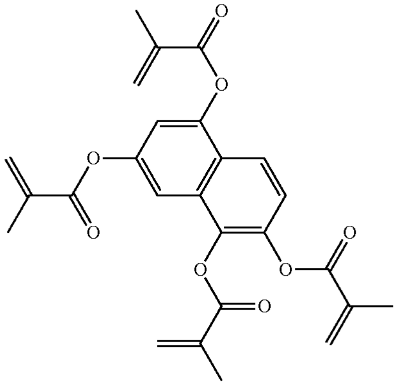
No.45
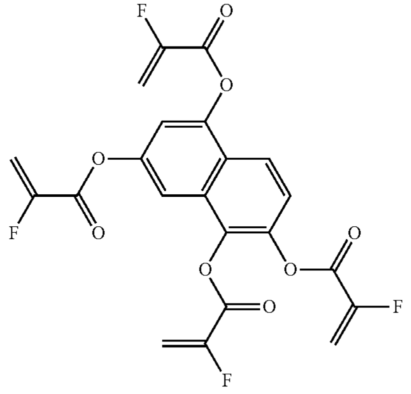
No.46
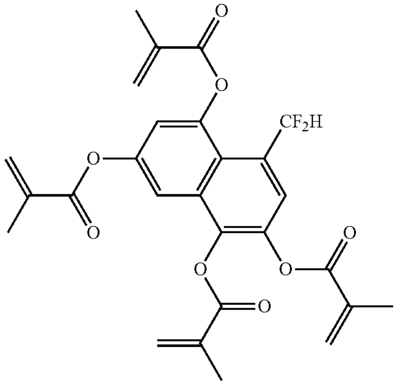
No.47
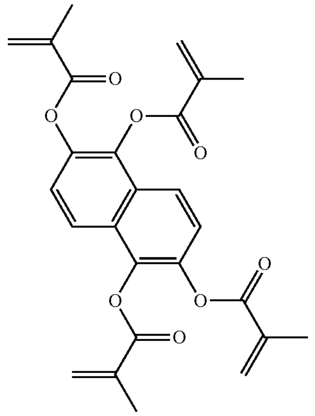
No.48
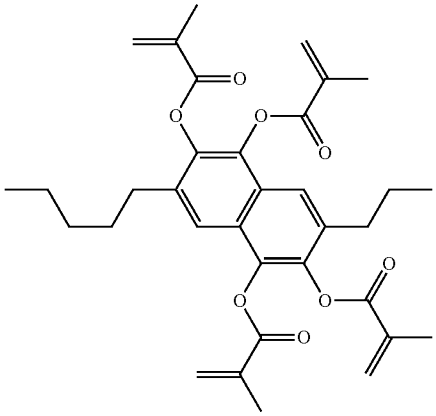

-continued
No.49
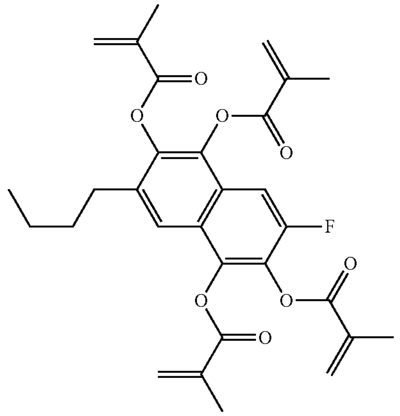
No.50
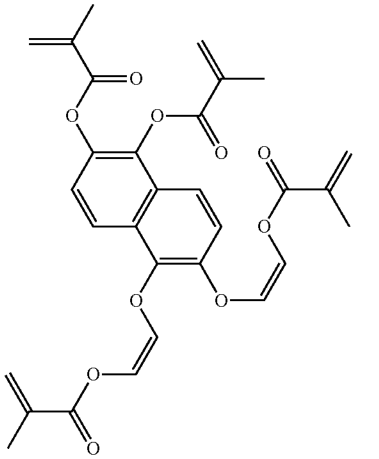
No.51
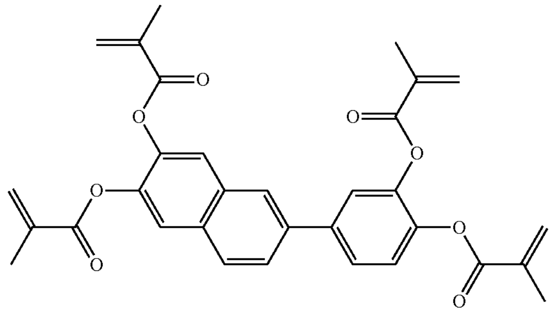
No.52
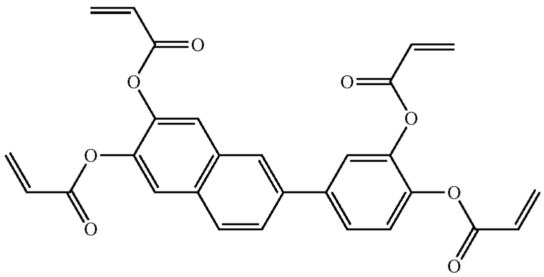
No.53
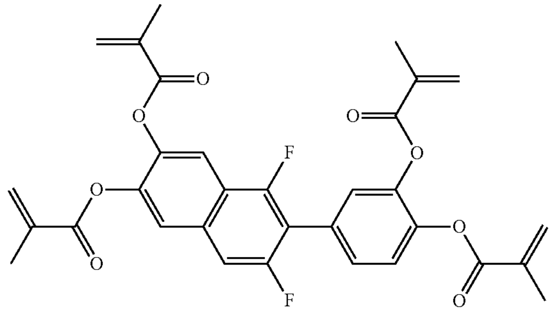
No.54
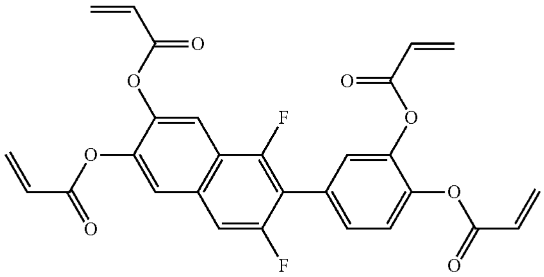
No.55
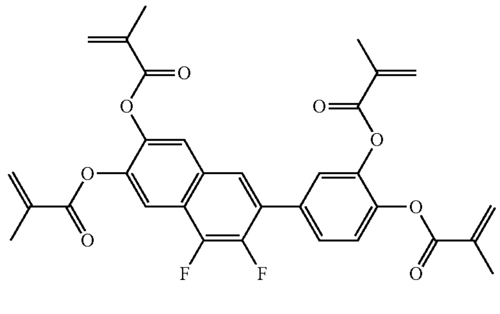
No.56
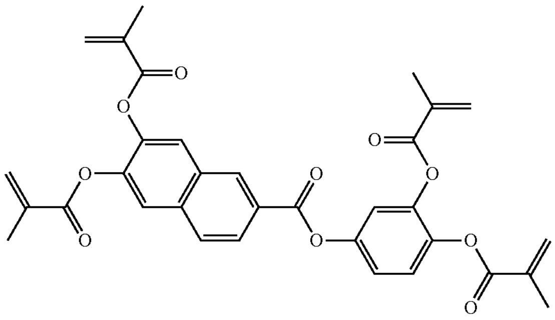

-continued
No.57
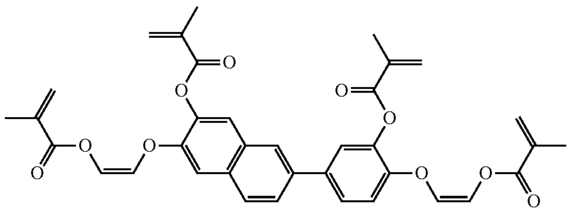
No.58
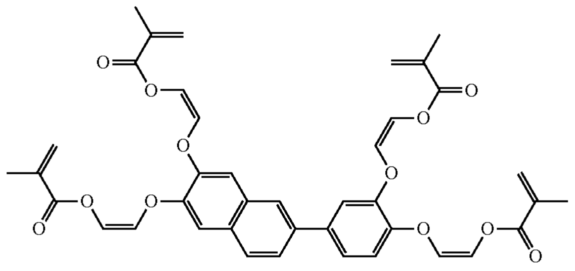
No.59
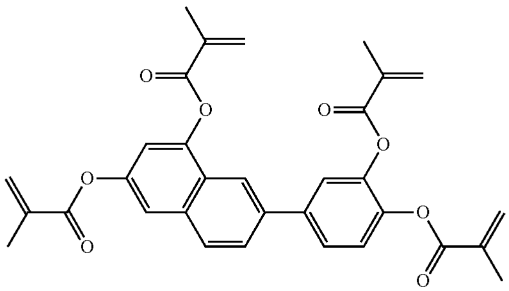
No.60
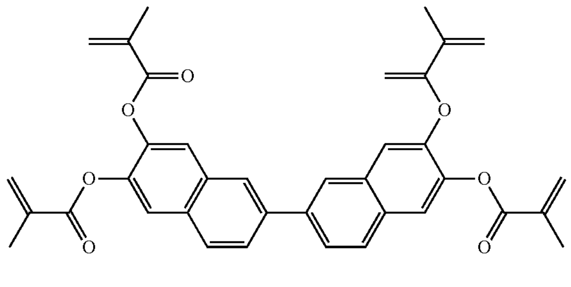
No.61
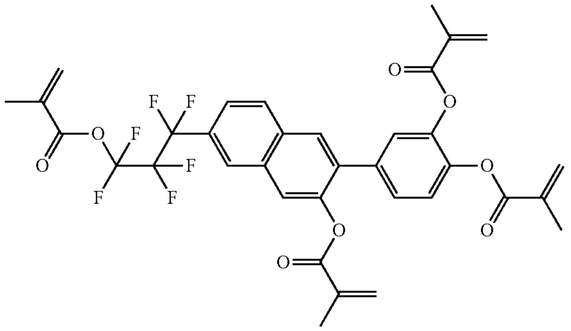
No.62
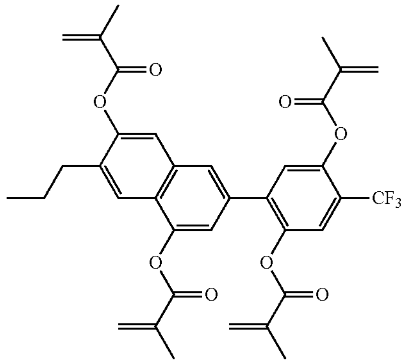
No.63
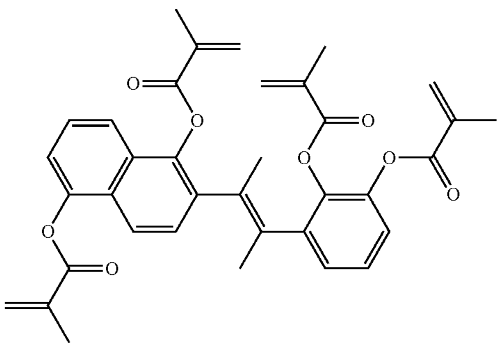
No.64
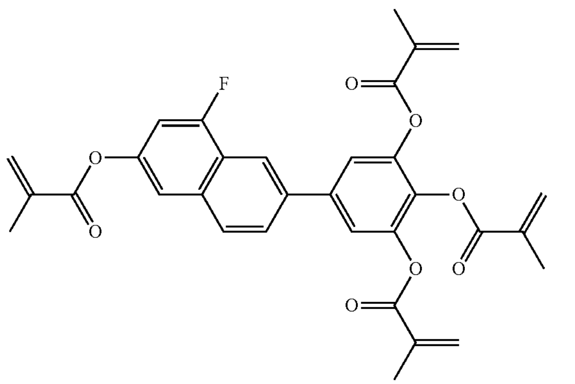

-continued
No.65
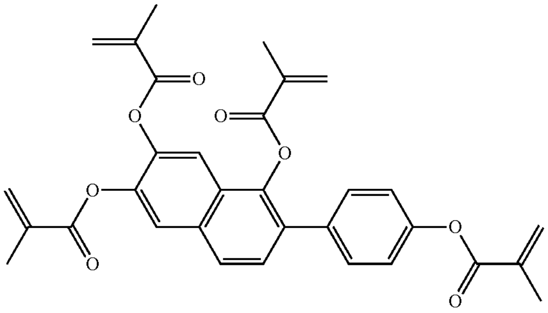
No.66
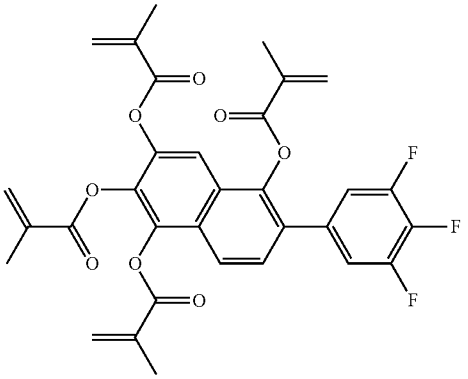
No.67
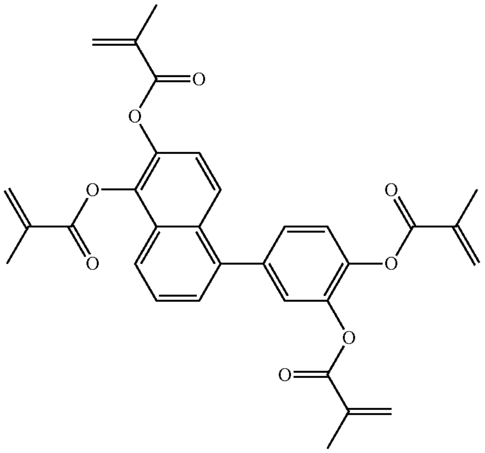
No.68
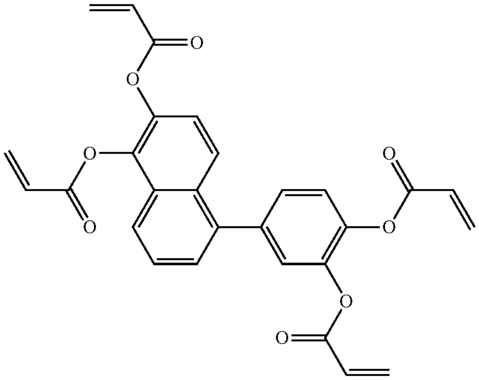
No.69
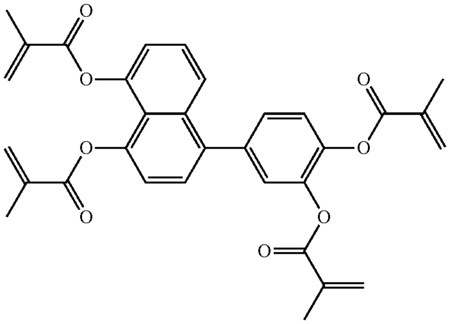
No.70
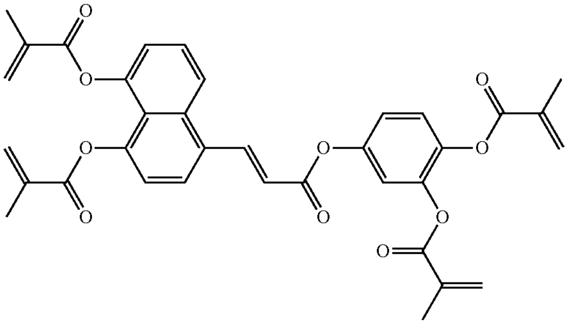
No.71
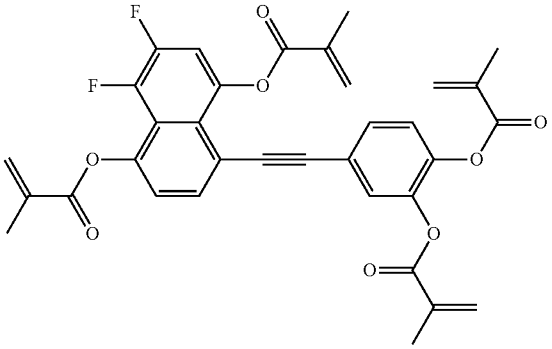
No.72
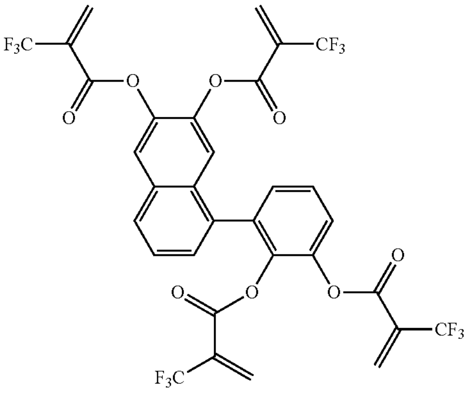

-continued
No.73
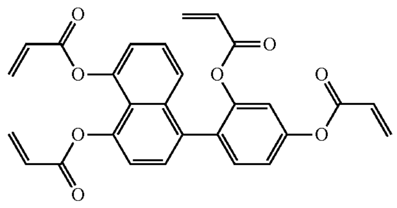
No.74
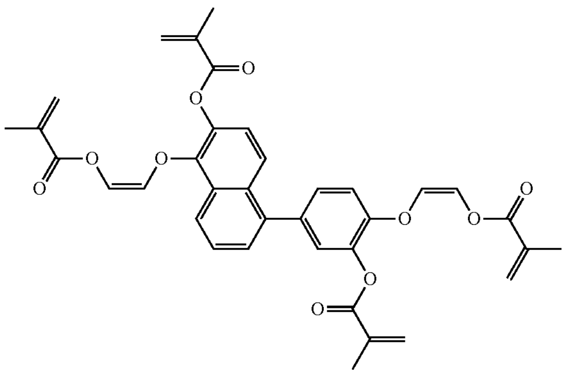
No.75
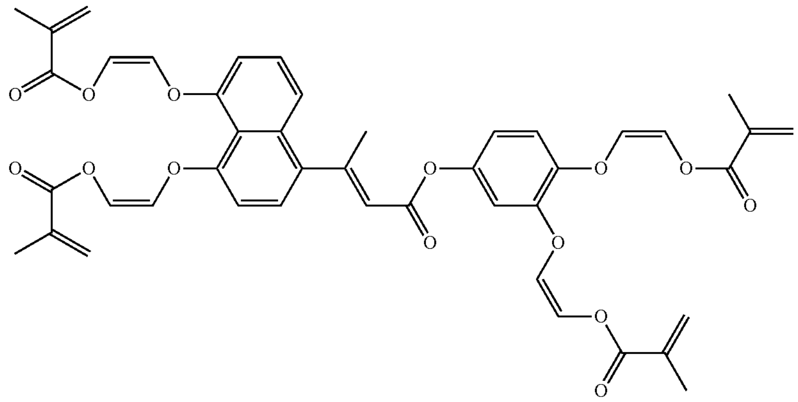
No.76
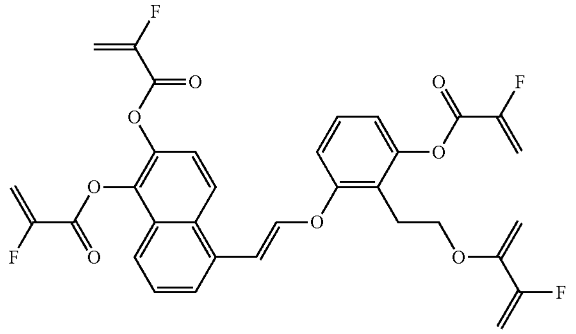
No.77
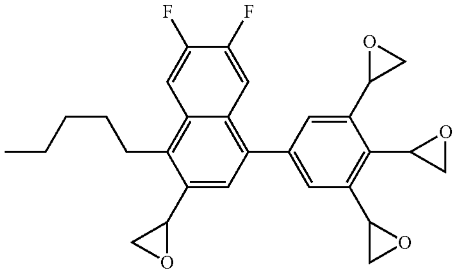
No.78
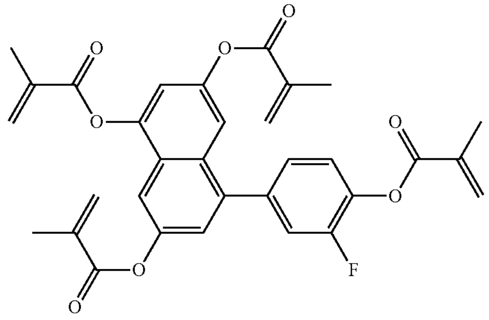
No.79
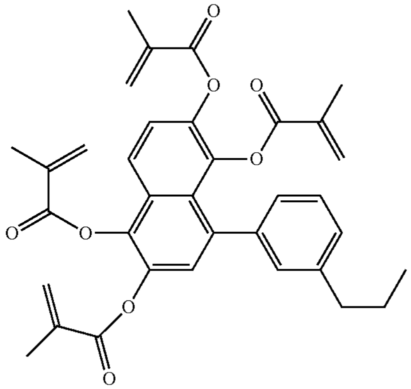

-continued
No.80
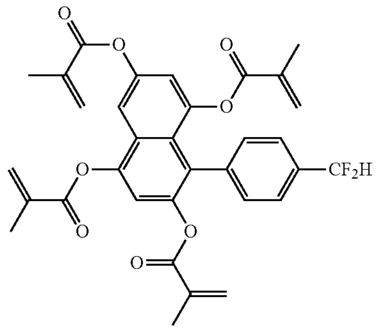
No.81
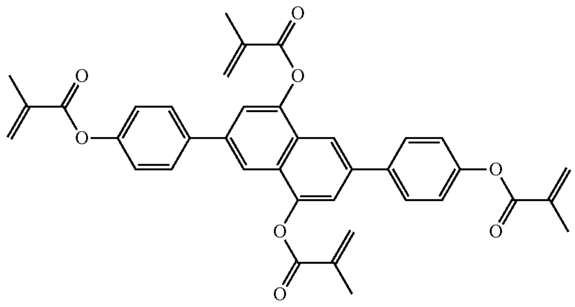
No.82
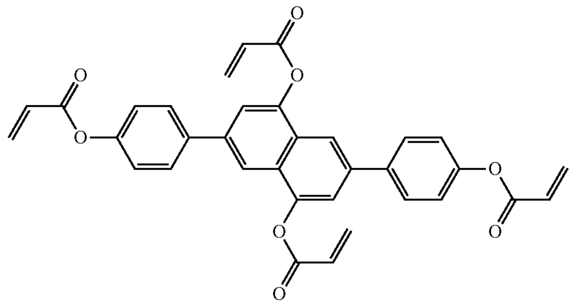
No.83
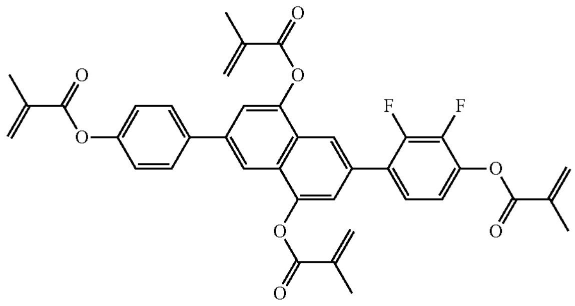
No.84
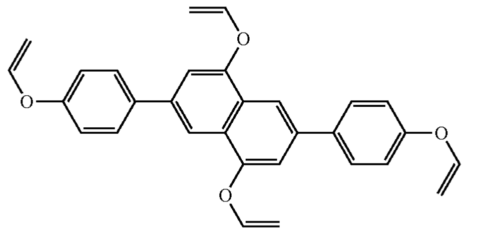
No.85
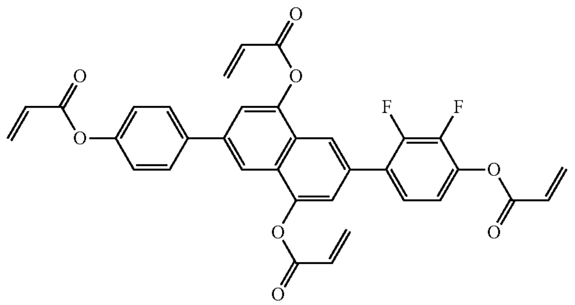
No.86
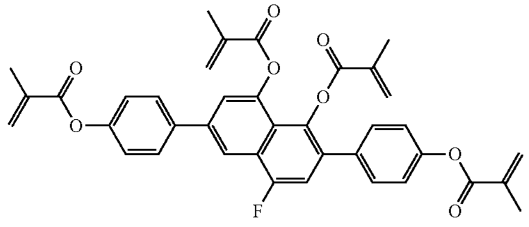
No.87
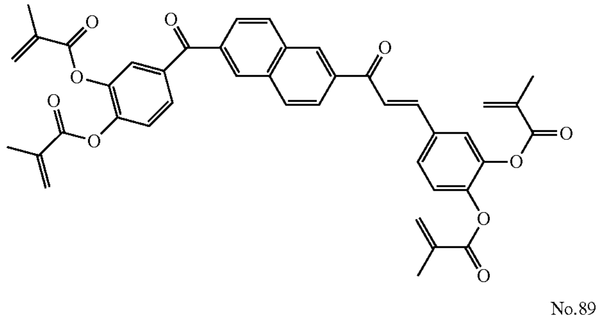
No.88
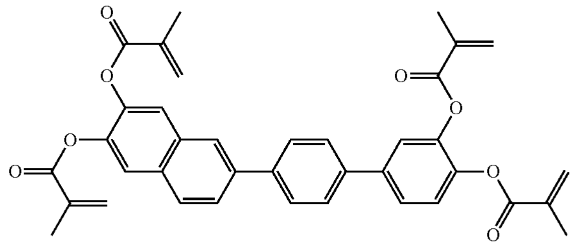
No.89
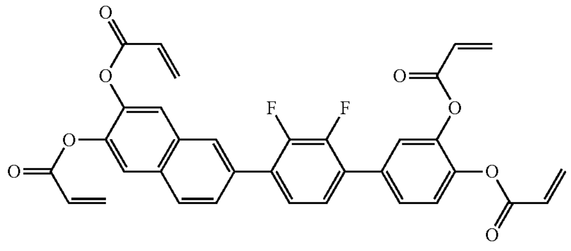

-continued
No.90
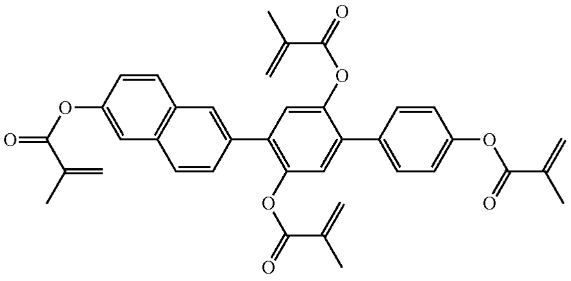
No.91
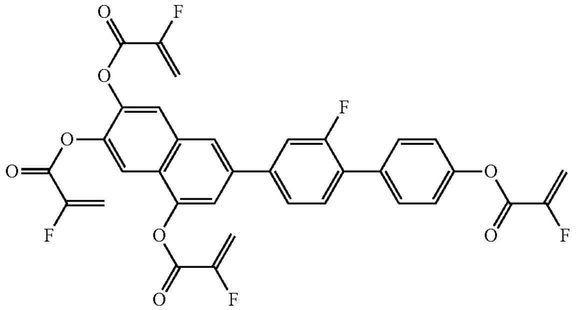
No.92
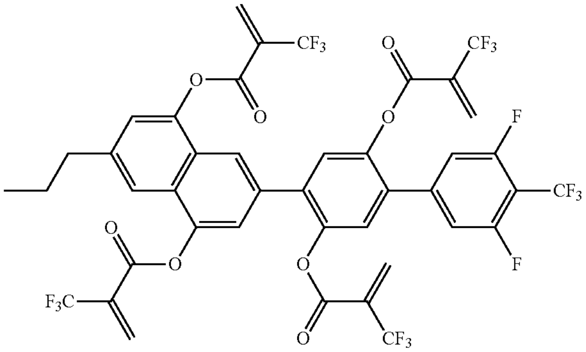
No.93
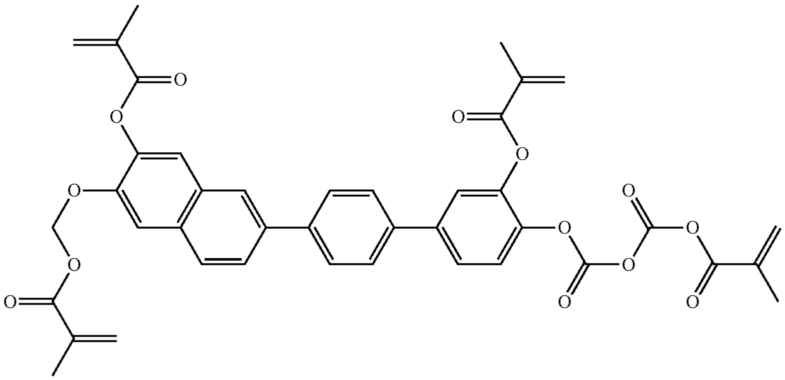
No.94
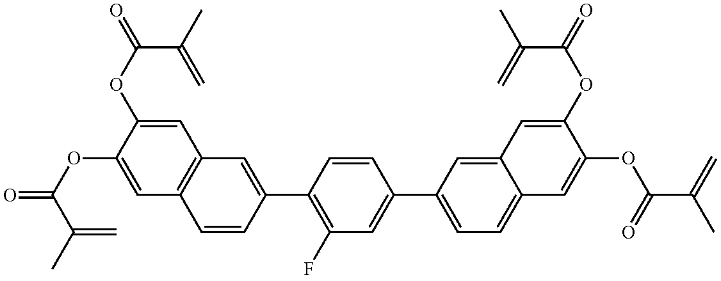
No.95
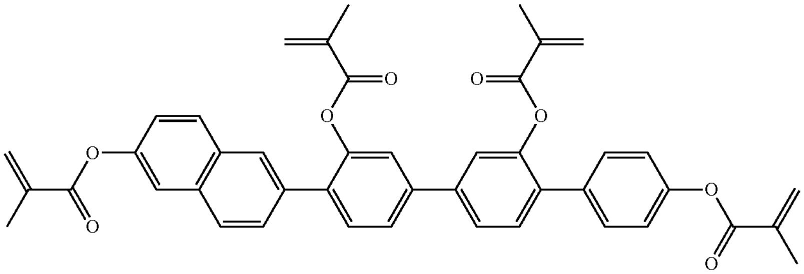

-continued
No.96
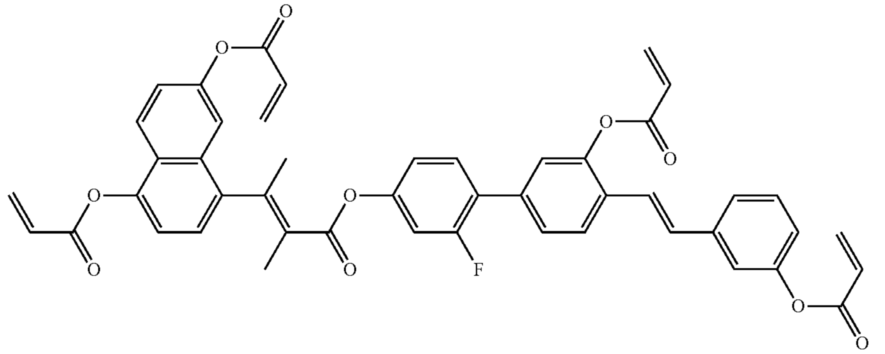
No.97
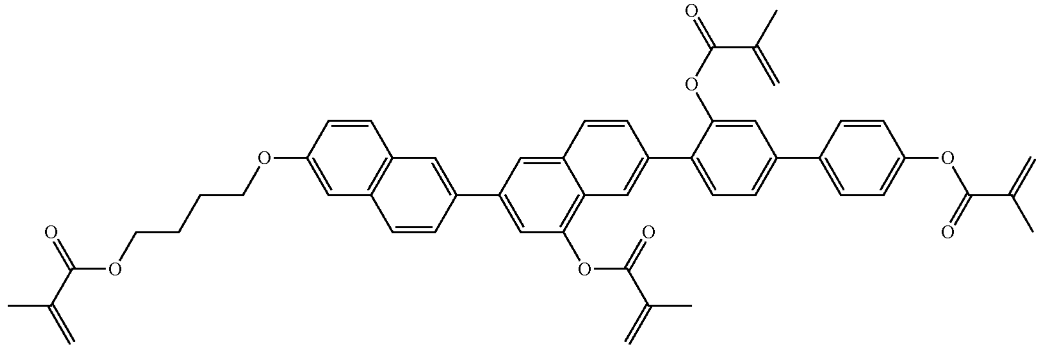
No.98
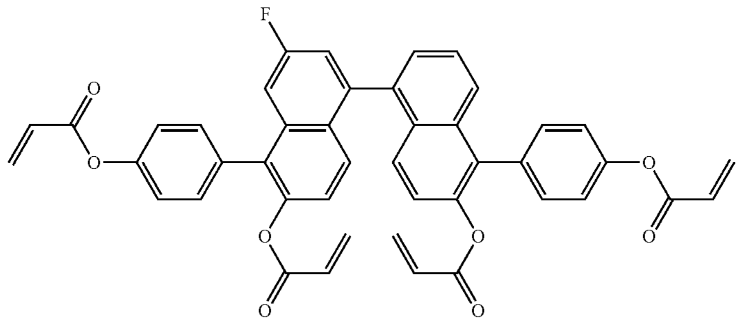
No.99
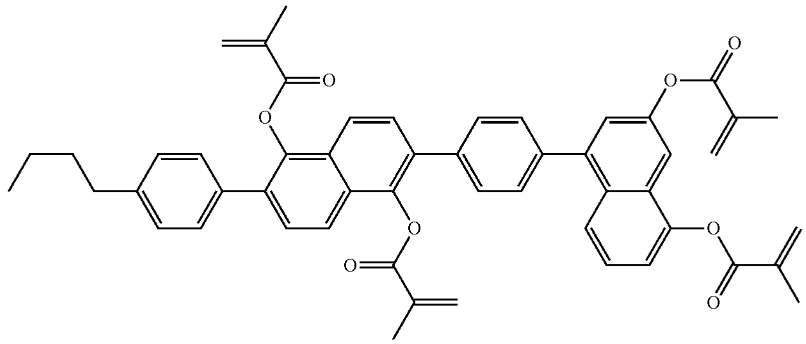

-continued
No.100
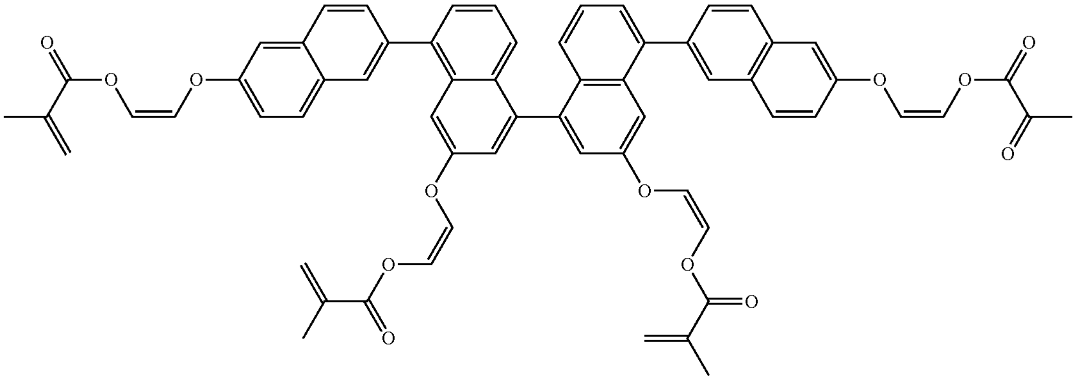
No.101
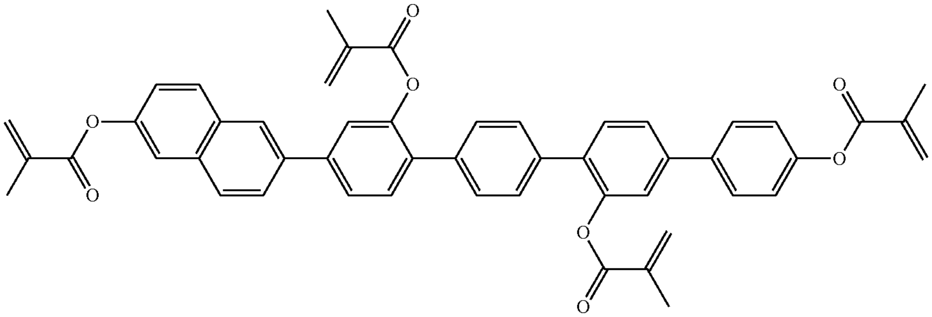
No.102
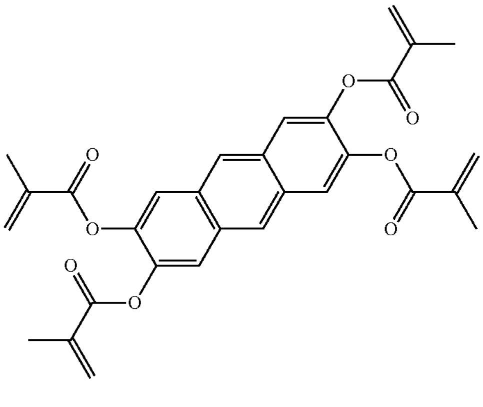
No.103
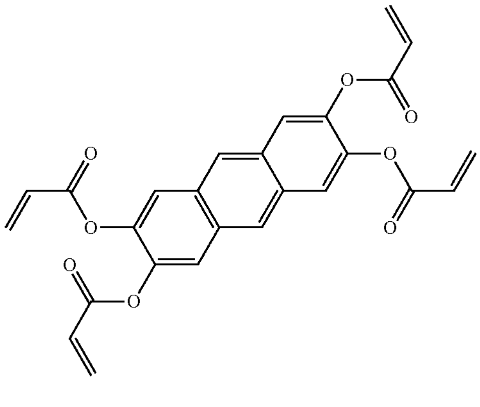
No.104
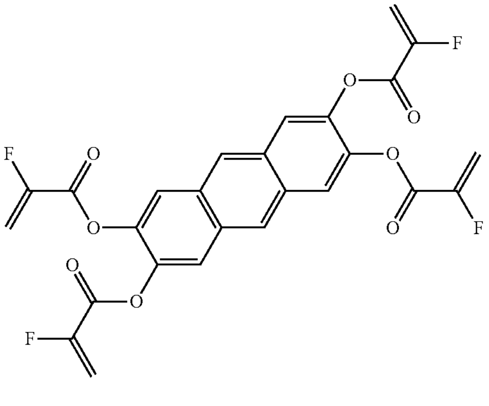
No.105
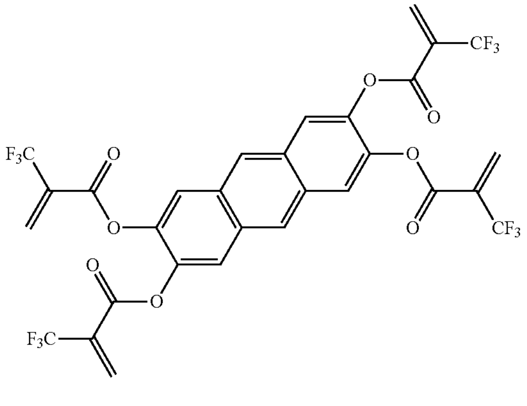

-continued
No.106
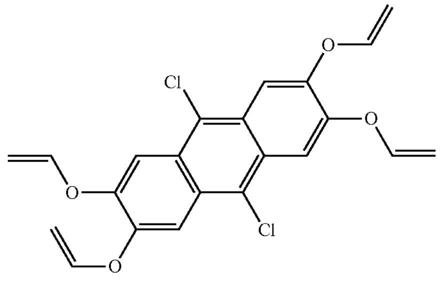
No.107
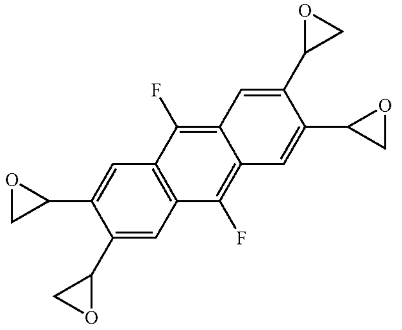
No.108
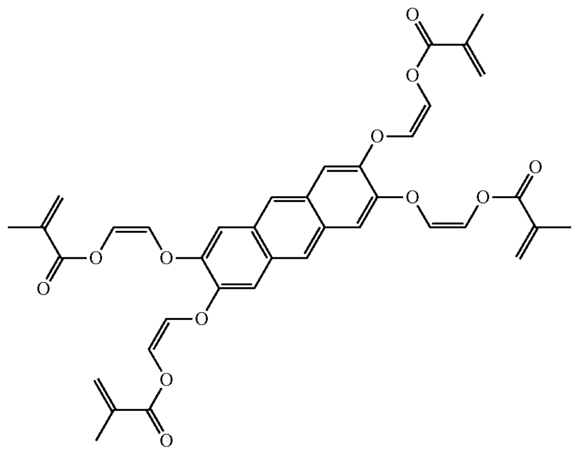
No.109
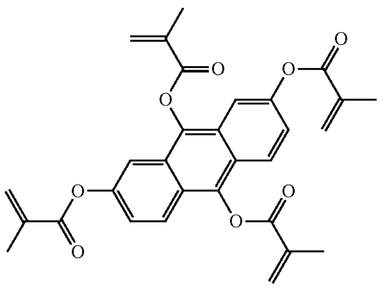
No.110
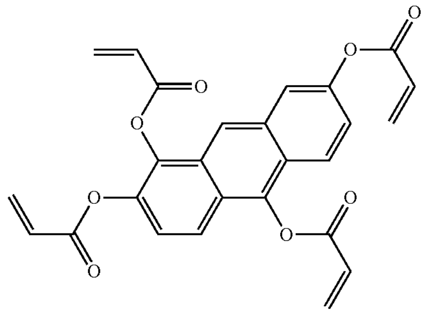
No.111
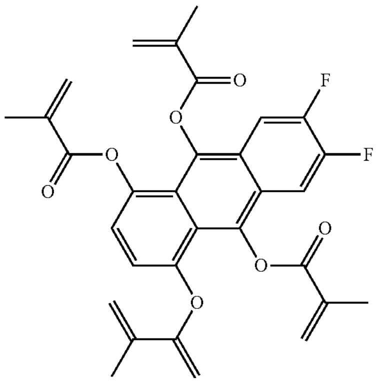
No.112
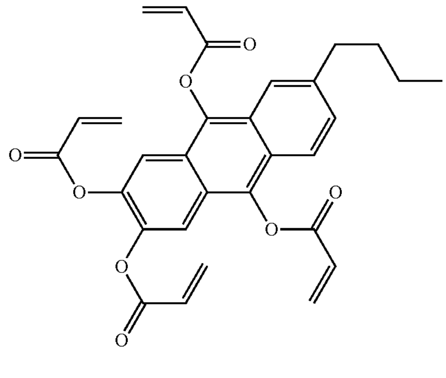
No.113
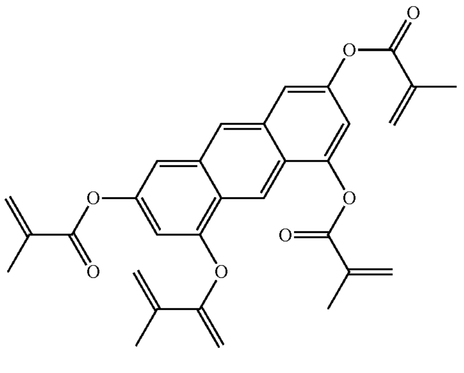

-continued
No.114
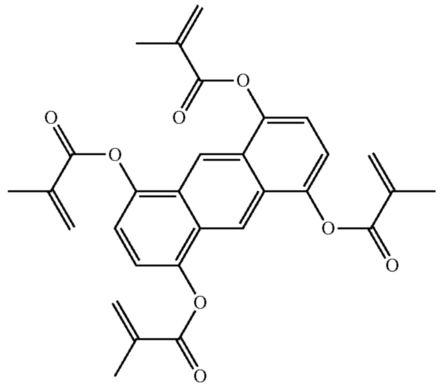
No.115
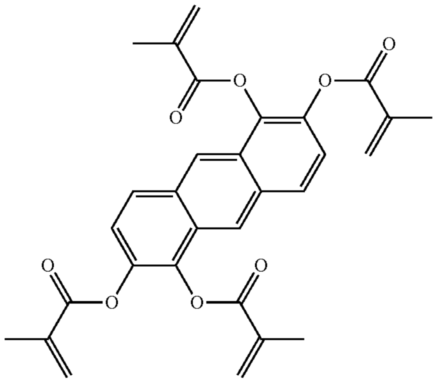
No.116
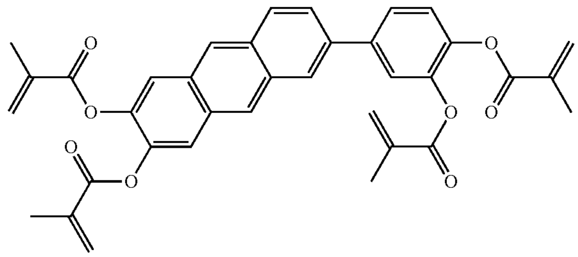
No.117
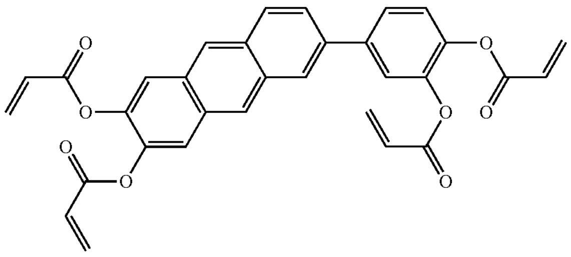
No.118
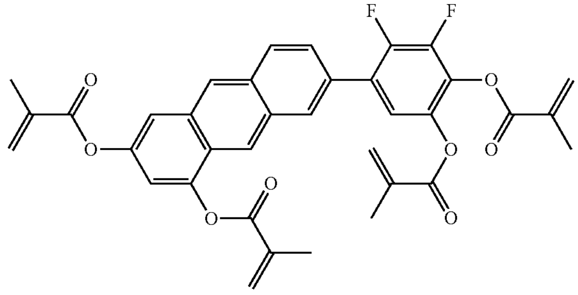
No.119
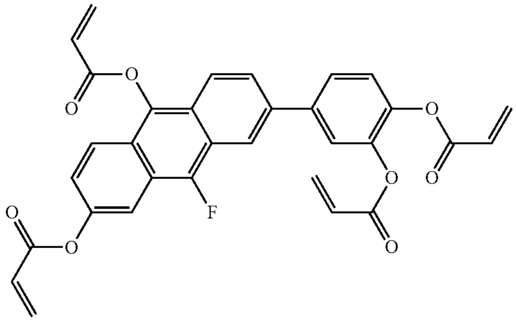
No.120
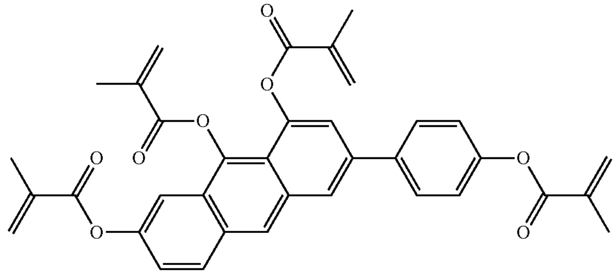

-continued
No.121
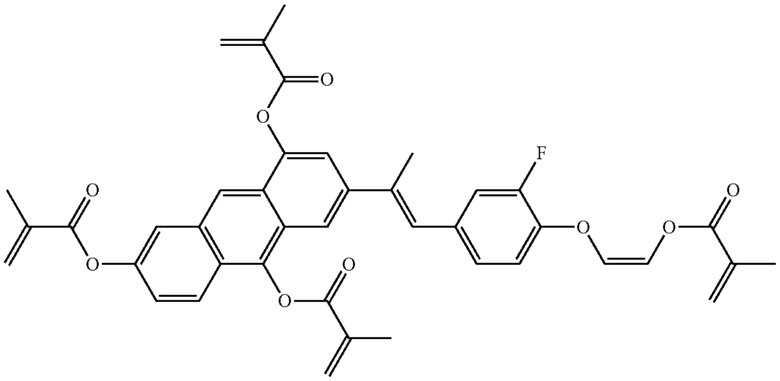
No.122
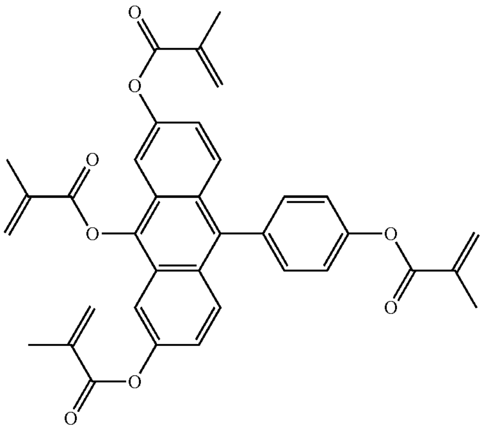
No.123
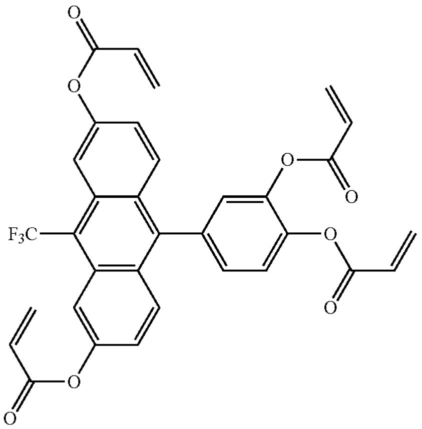
No.124
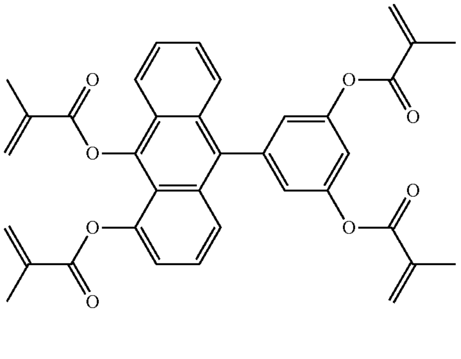
No.125
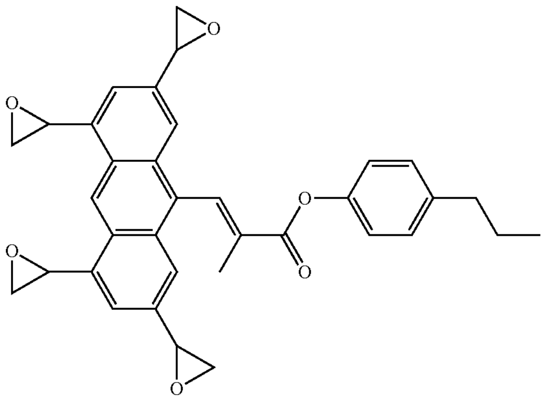

-continued
No.126
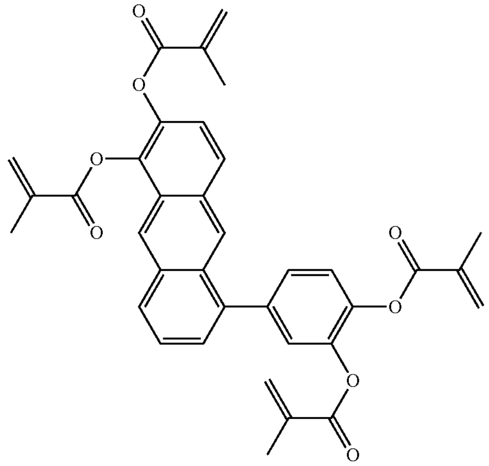
No.127
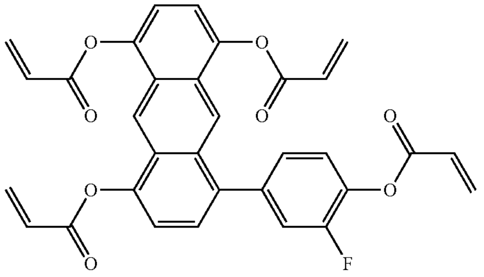
No.128
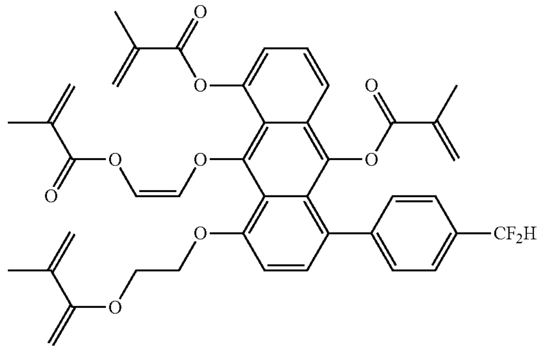
No.129
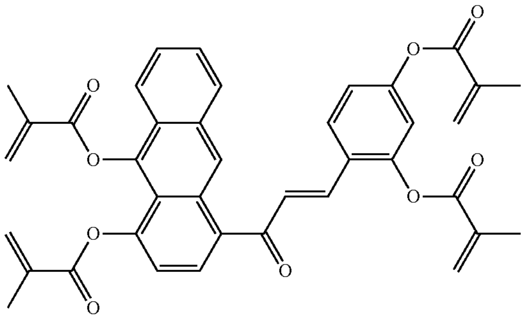
No.130
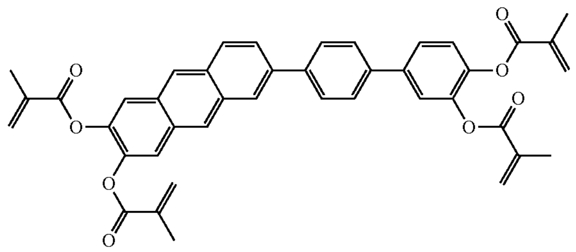
No.131
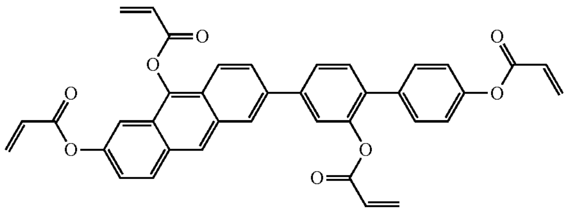
No.132
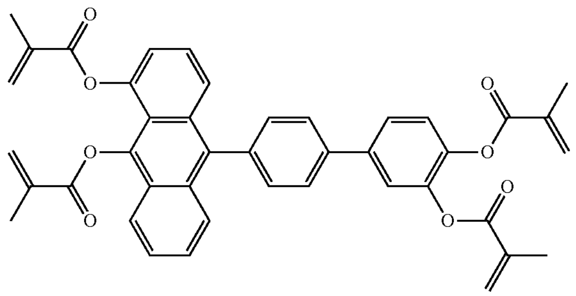
No.133
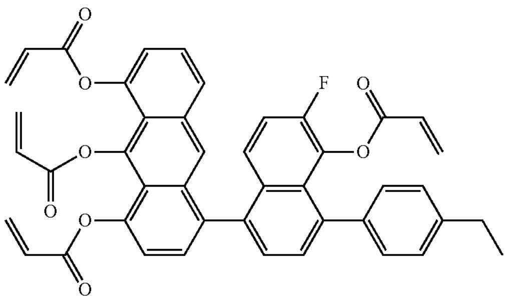

-continued
No.134
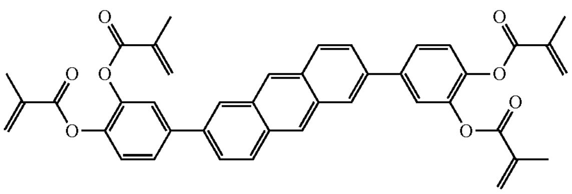
No.135
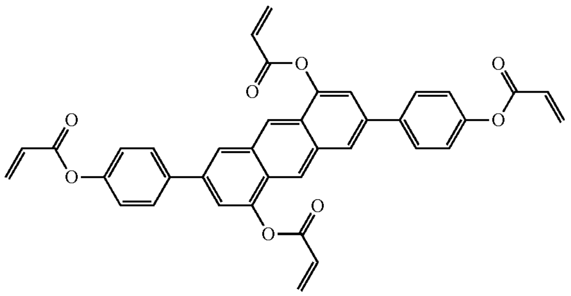
No.136
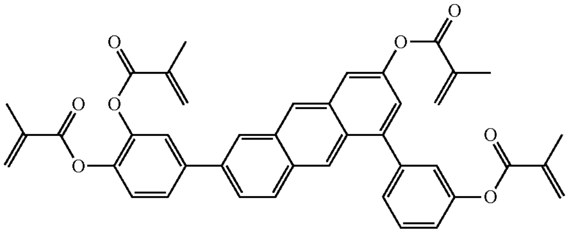
No.137
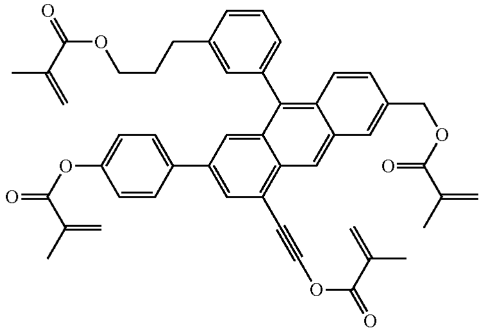
No.138
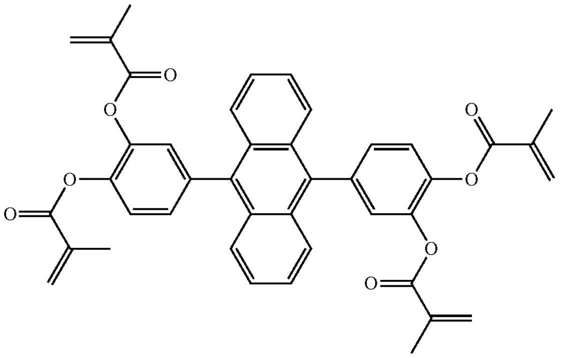
No.139
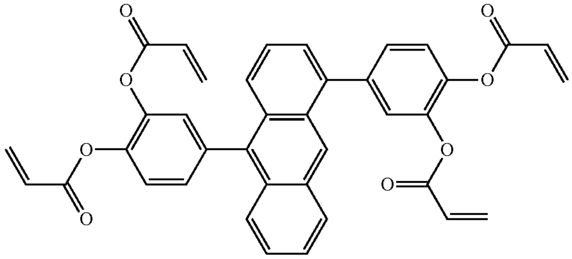
No.140
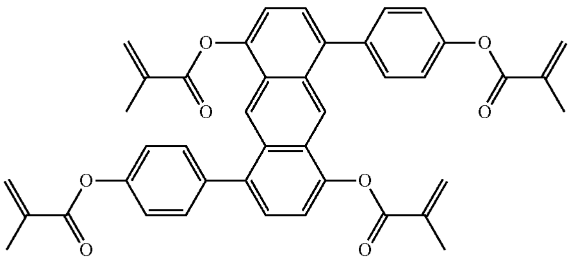
No.141
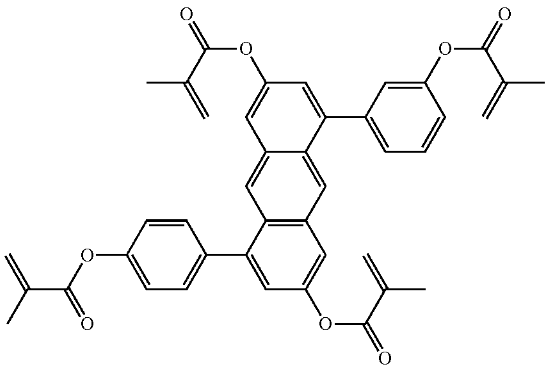

-continued
No.142
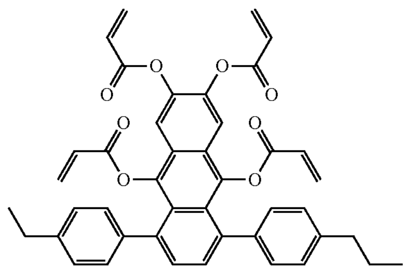
No.143
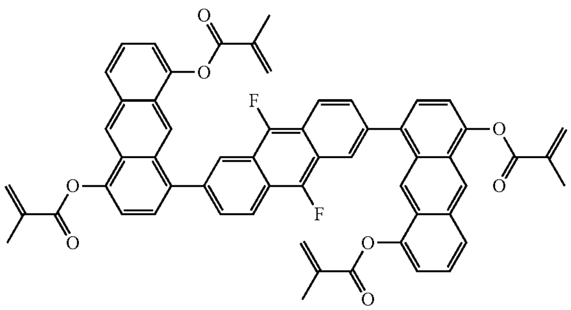
No.144
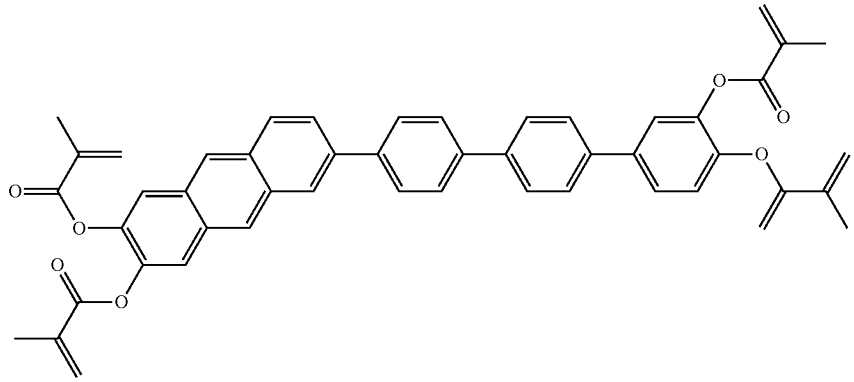
No.145
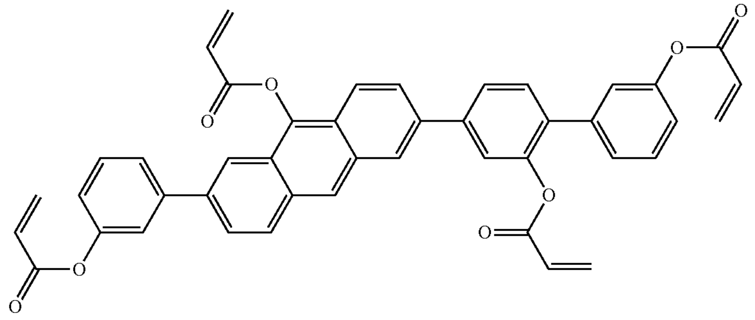
No.146
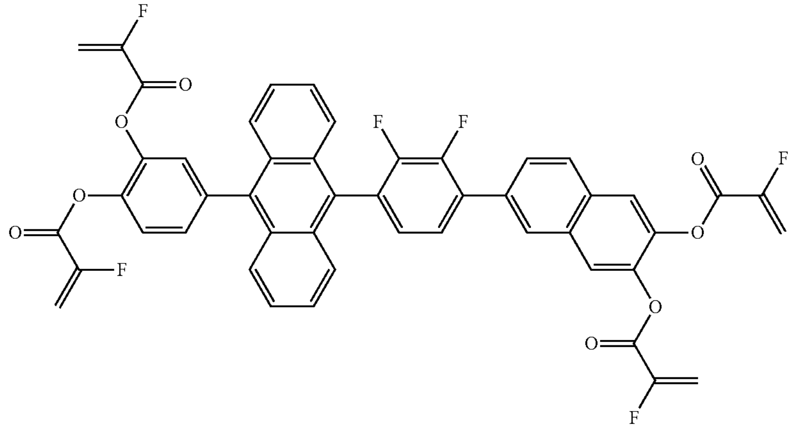

-continued
No.147
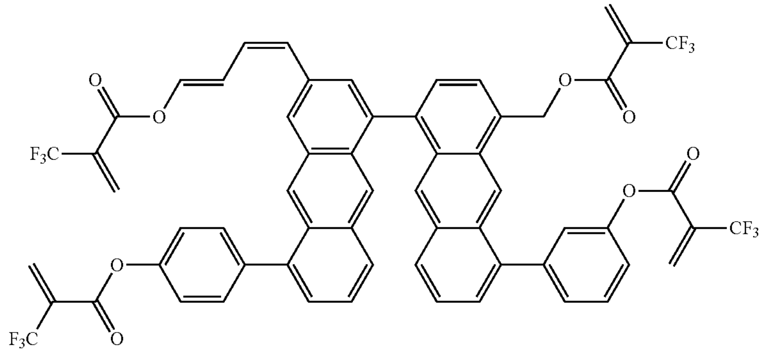
No.148
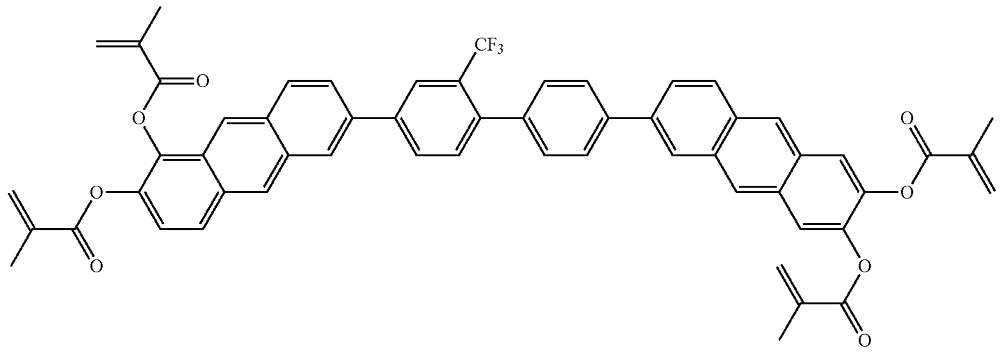
No.149
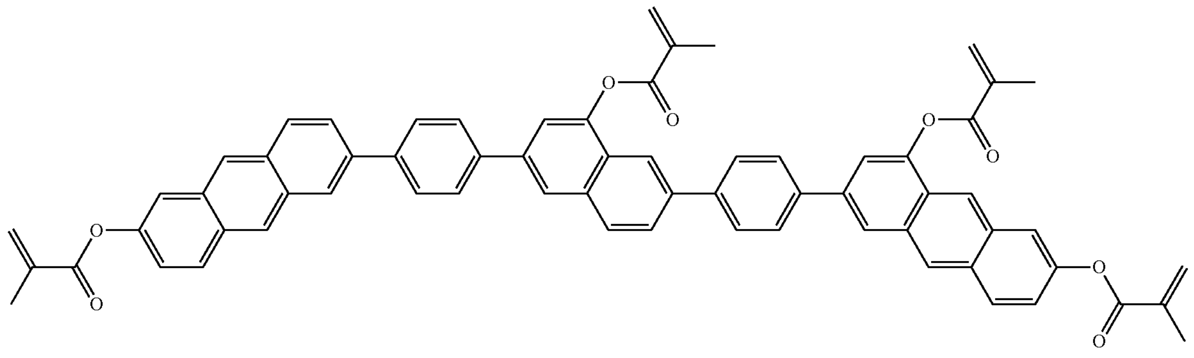
No.150
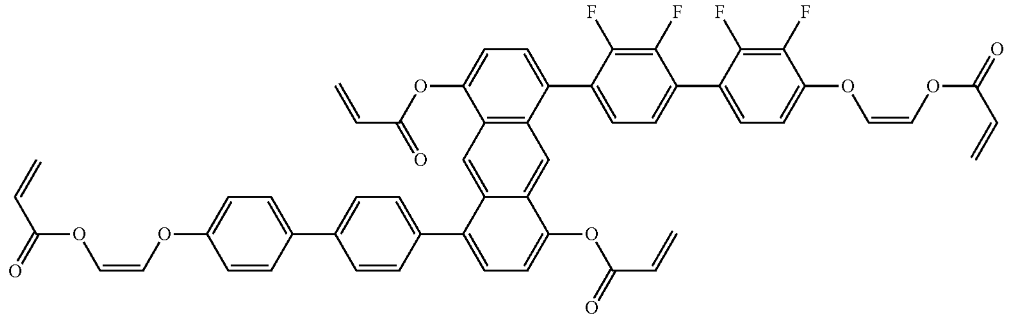

-continued
No.151
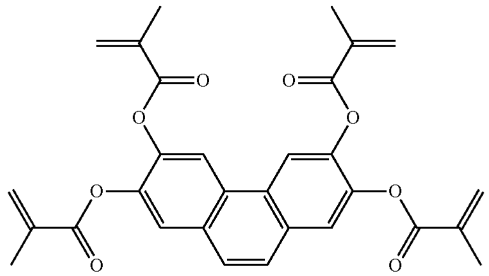
No.152
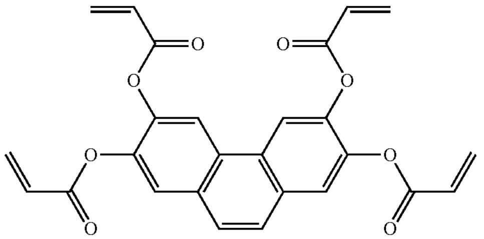
No.153
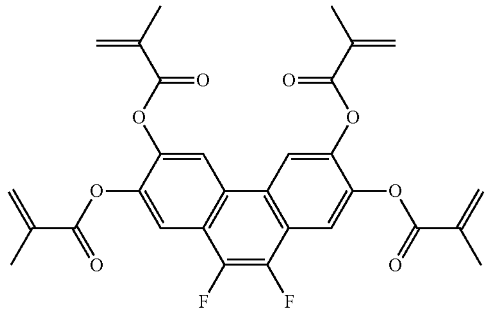
No.154
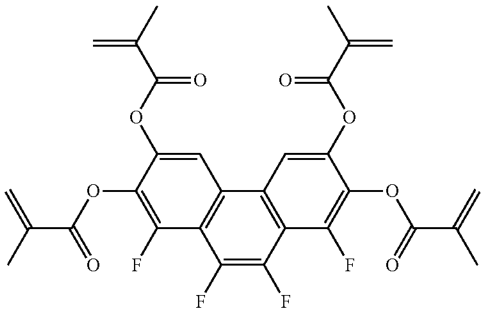
No.155
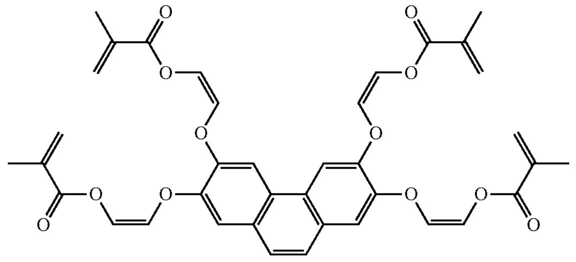
No.156
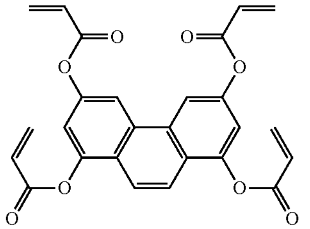
No.157
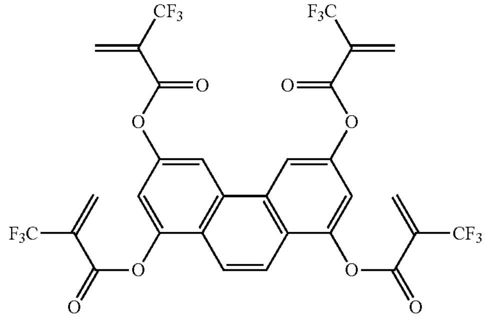
No.158
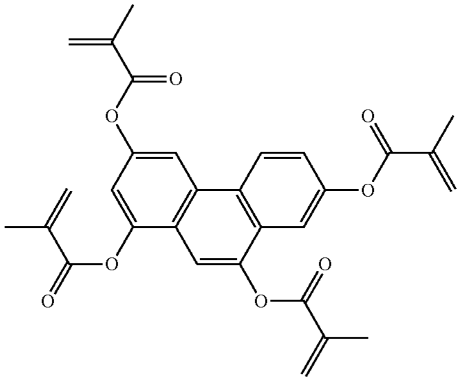

-continued
No.159
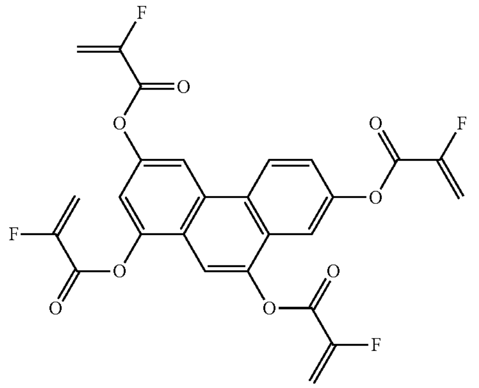
No.160
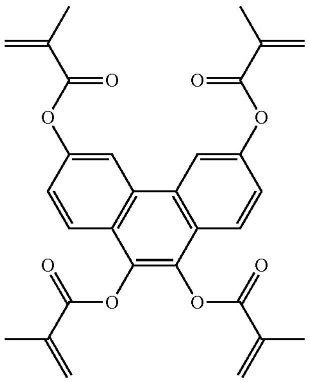
No.161
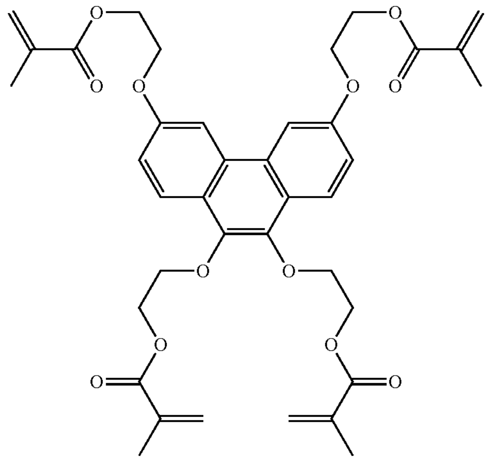
No.162
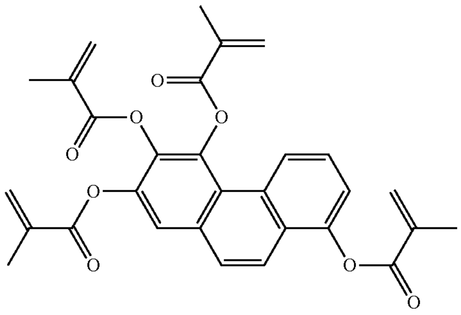
No.163
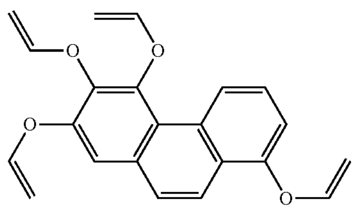
No.164
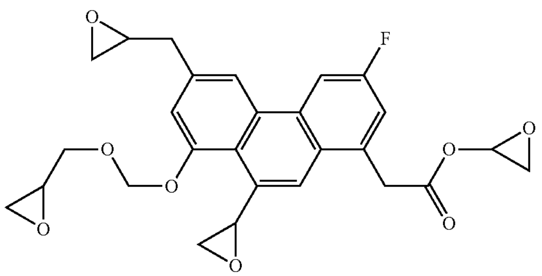
No.165
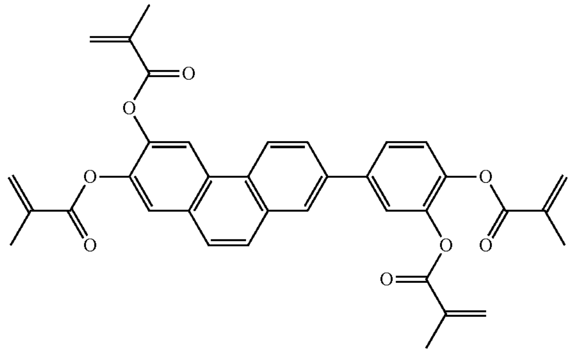
No.166
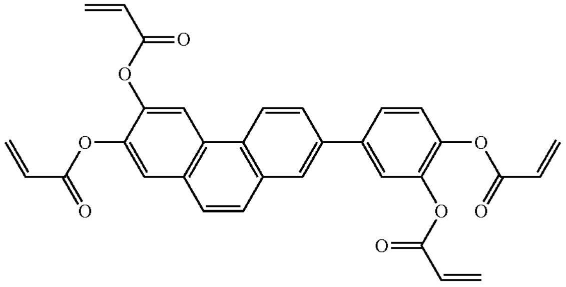

-continued
No.167
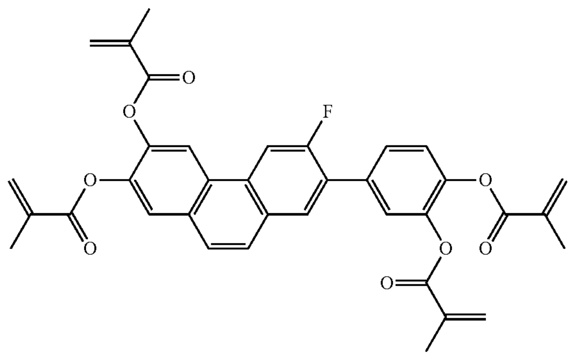
No.168
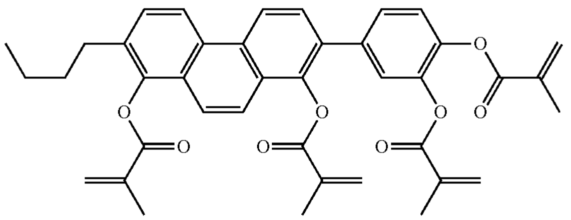
No.169
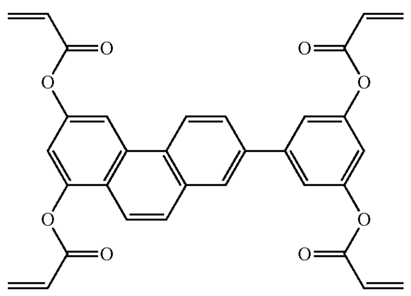
No.170
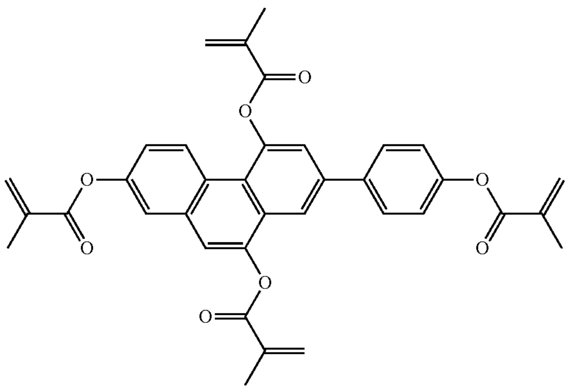
No.171
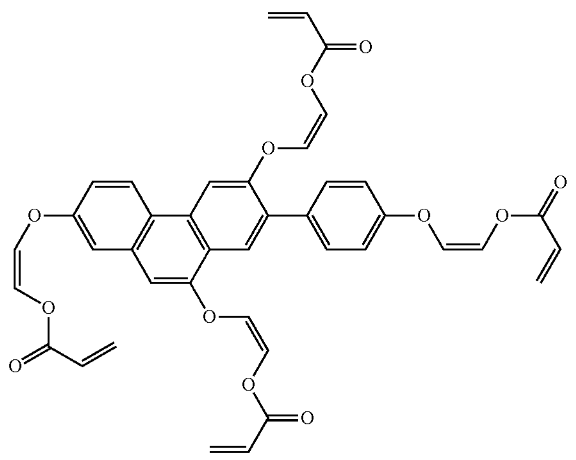
No.172
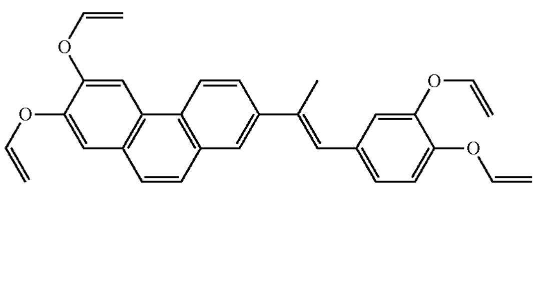

-continued
No.173
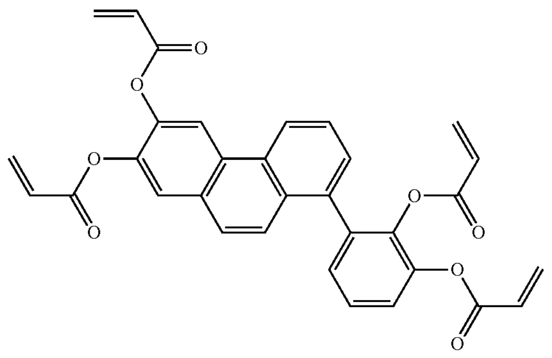
No.174
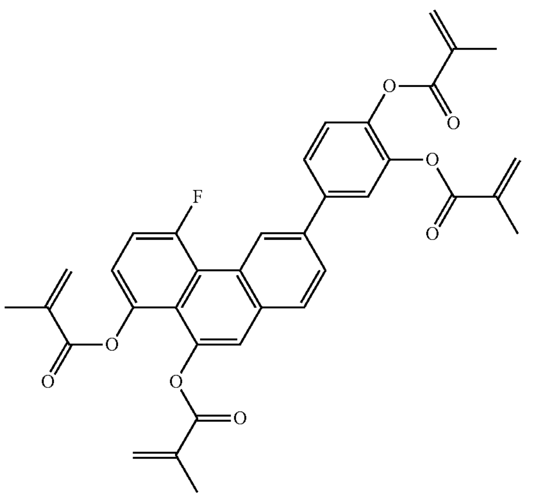
No.175
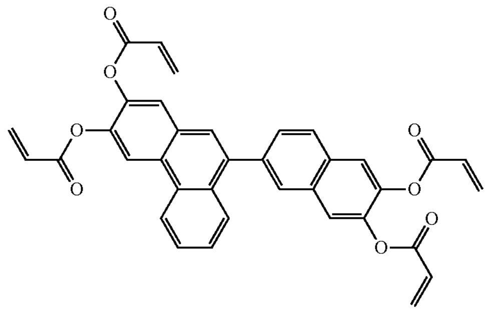
No.176
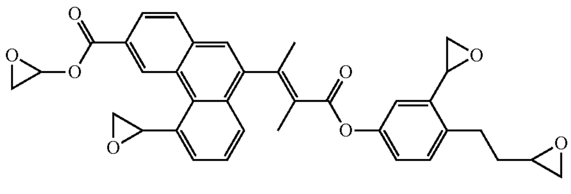
No.177
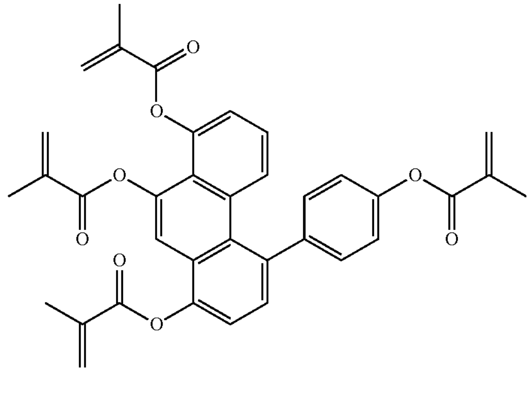
No.178
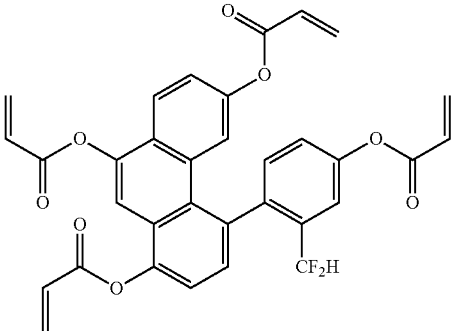
No.179
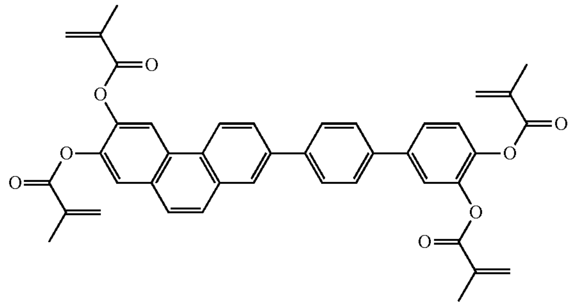
No.180
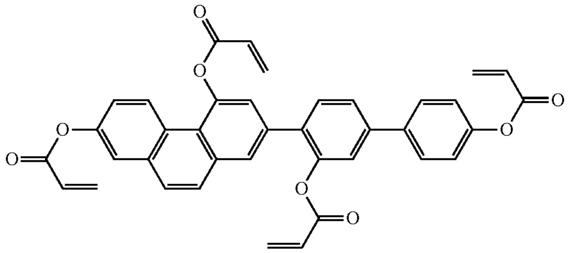

-continued
No.181
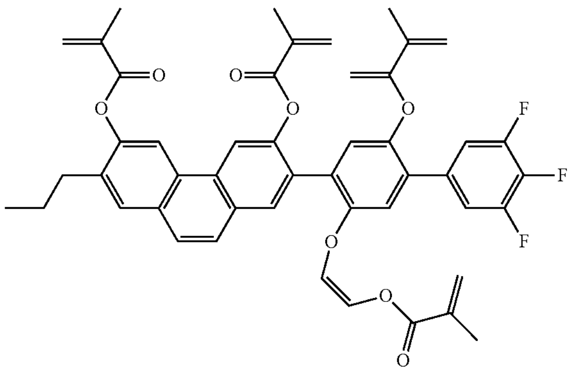
No.182
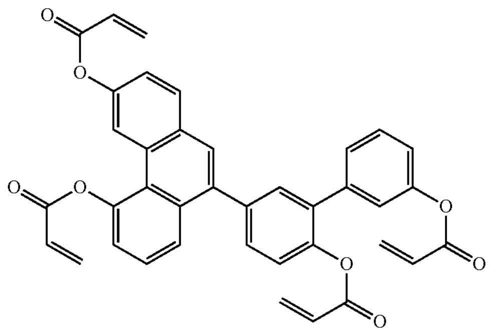
No.183
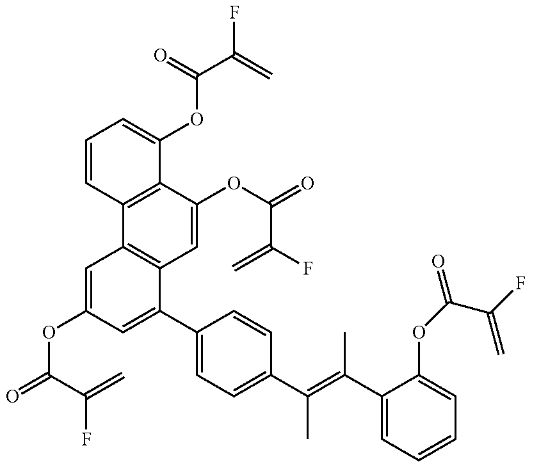
No.184
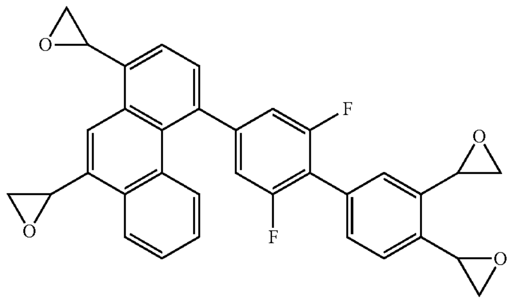
No.185
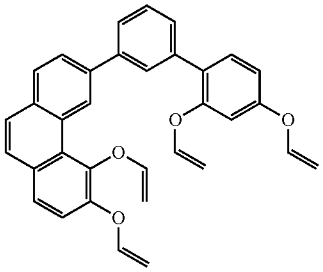
No.186
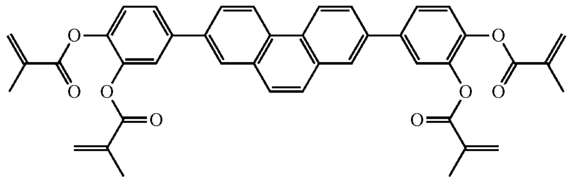
No.187
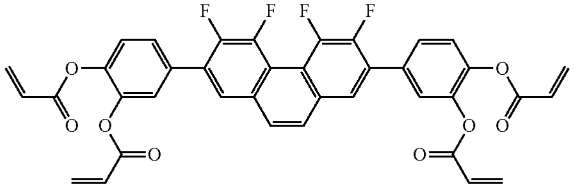
No.188
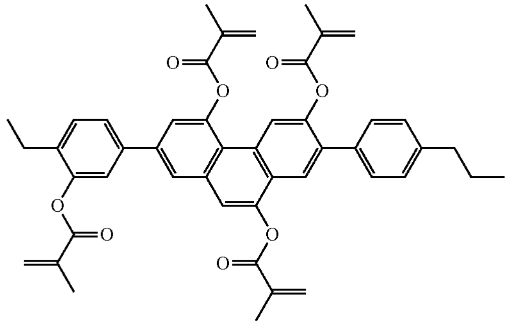

-continued
No.189
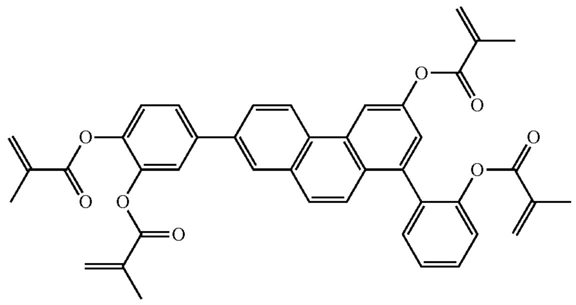
No.190
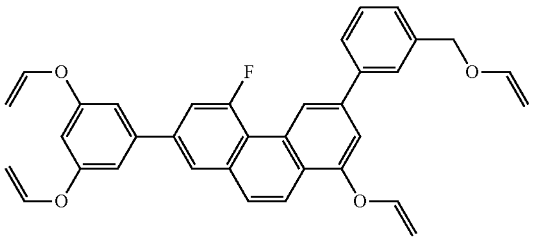
No.191
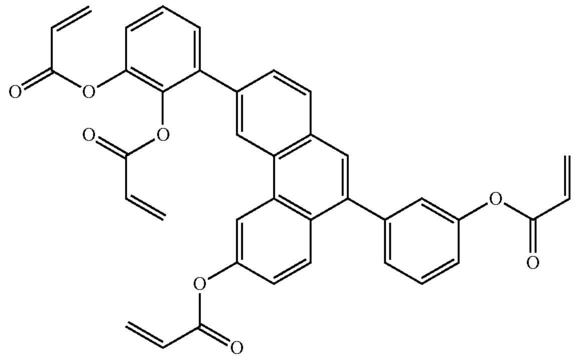
No.192
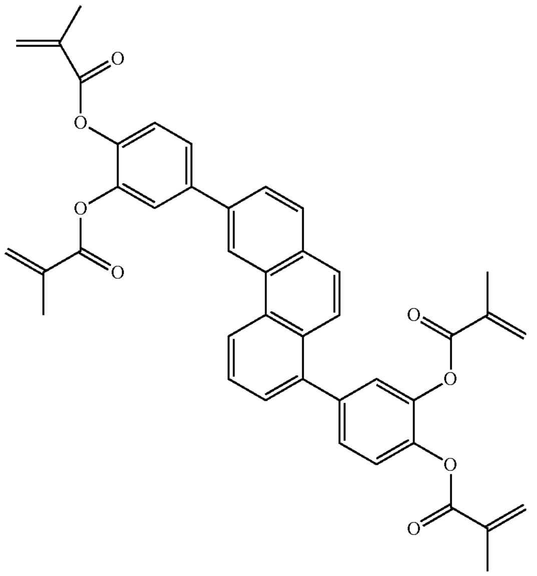
No.193
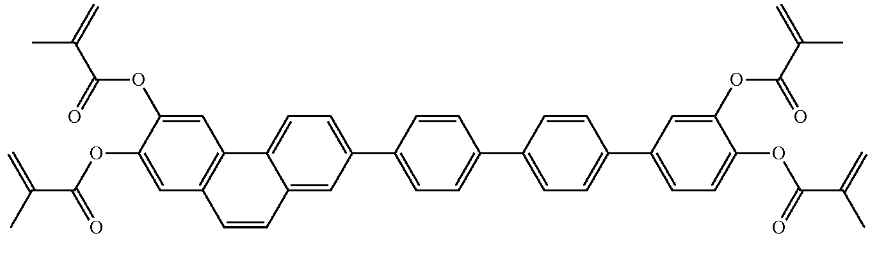
No.194
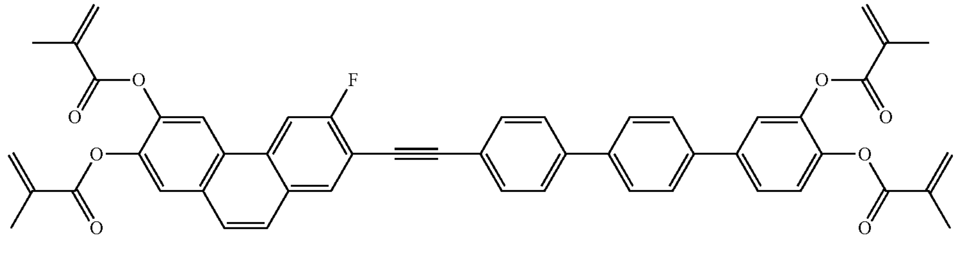

-continued
No.195
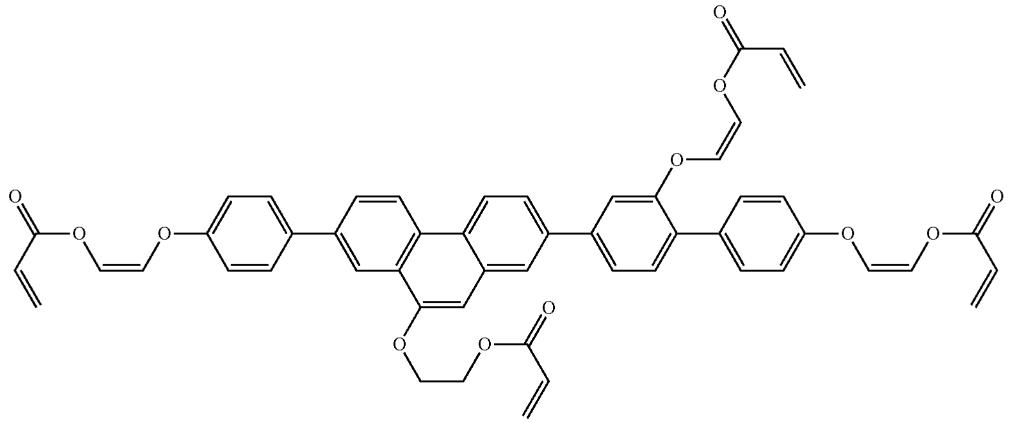
No.196
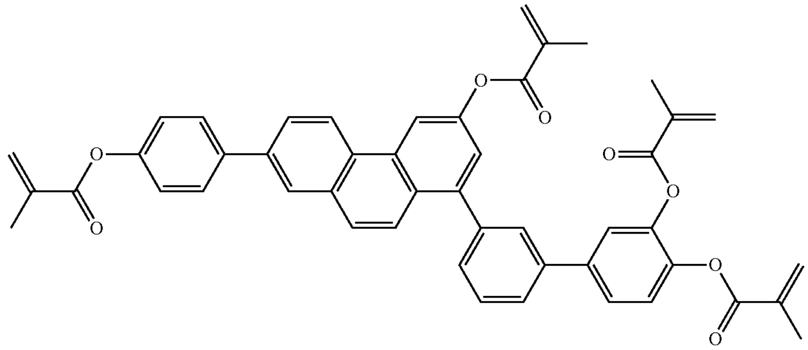
No.197
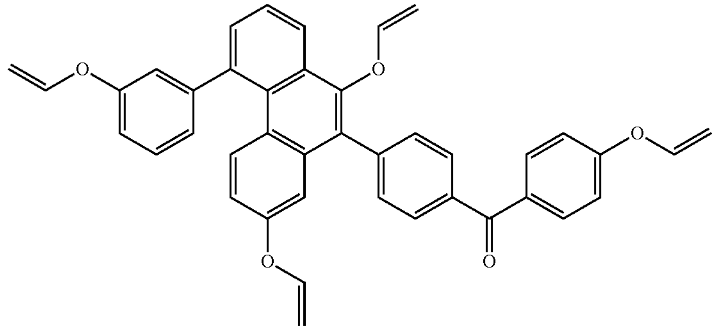
No.198
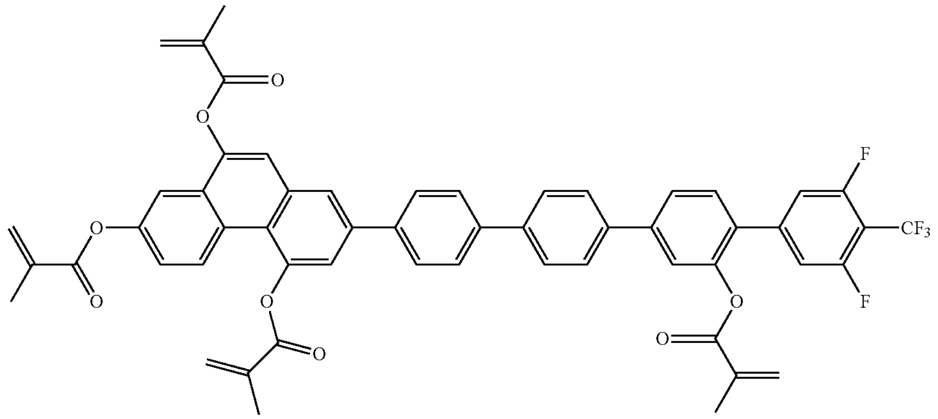

-continued

No.199

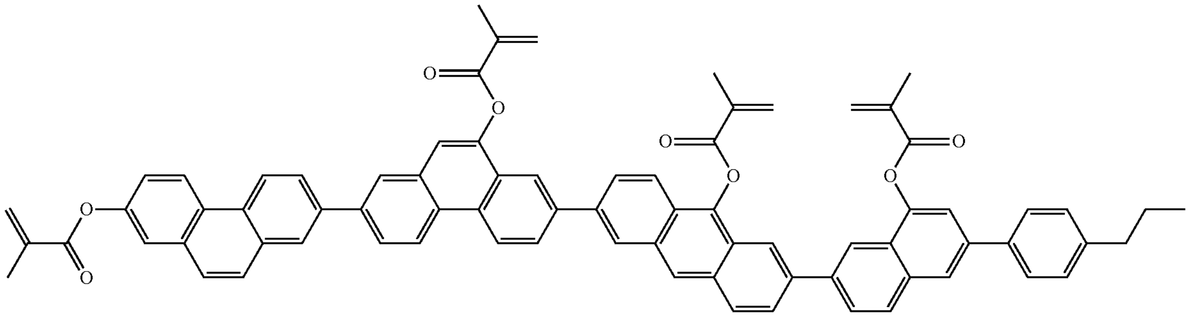

2. Example of Polymerizable Composition

Compounds described in Examples were expressed using symbols based on definitions in Table 2 below. In Table 2, a configuration of 1,4-cyclohexylene is trans. A parenthesized number next to a symbolized compound in Examples corresponds to the number of the compound. A symbol (-) means any other liquid crystal compound. A content (percentage) of a liquid crystal compound is expressed in terms of weight percent (% by weight) based on the liquid crystal composition. Values of physical properties of the composition were summarized in a last part. The physical properties were measured in accordance with the methods described above, and measured values were directly described (without extrapolation).

TABLE

Method for Description of Compounds using Symbols
R—$(A_1)$—$Z_1$— . . . —$Z_n$—$(A_n)$—R'

| 1) Left-terminal Group R— | Symbol |
|---|---|
| $C_nH_{2n+1}$— | n- |
| $C_nH_{2n+1}O$— | nO— |
| $C_mH_{2m+1}OC_nH_{2n}$— | mOn- |
| $CH_2$═CH— | V— |
| $C_nH_{2n+1}$—CH═CH— | nV— |
| $CH_2$═CH—$C_nC_{2n}$— | Vn- |
| $C_mH_{2m+1}$—CH═CH—$C_nH_{2n}$— | mVn- |
| $CF_2$═CH— | VFF— |
| $CF_2$═CH—$C_nH_{2n}$— | VFFn- |
| **2) Right-terminal Group —R'** | **Symbol** |
| —$C_nH_{2n+1}$ | -n |
| —$OC_nH_{2n+1}$ | —On |
| —$COOCH_3$ | —EMe |
| —CH═$CH_2$ | —V |
| —CH═CH—$C_nH_{2n+1}$ | —Vn |
| —$C_nH_{2n}$—CH═$CH_2$ | -nV |
| —$C_mH_{2m}$—CH═CH—$C_nH_{2n+1}$ | -mVn |
| —CH═$CF_2$ | —VFF |
| —F | —F |
| —Cl | —CL |
| —$OCF_3$ | —OCF3 |
| —$OCF_2H$ | —OCF2H |
| —$CF_3$ | —CF3 |
| —OCH═CH—$CF_3$ | —OVCF3 |
| —C≡N | —C |
| **3) Bonding Group —$Z_n$—** | **Symbol** |
| —$C_nH_{2n}$— | n |
| —COO— | E |
| —CH═CH— | V |
| —$CH_2O$— | 1O |
| —$OCH_2$— | O1 |
| —$CF_2O$— | X |
| —C≡C— | T |

TABLE-continued

Method for Description of Compounds using Symbols
R—$(A_1)$—$Z_1$— . . . —$Z_n$—$(A_n)$—R'

| 4) Ring Structure —$A_n$— | Symbol |
|---|---|
| 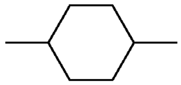 | H |
| 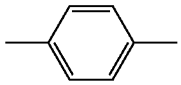 | B |
| 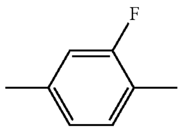 | B(F) |
| 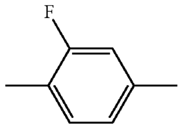 | B(2F) |
| 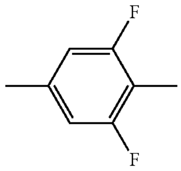 | B(F,F) |
| 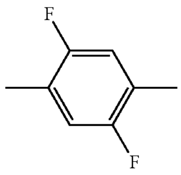 | B(2F,5F) |
| 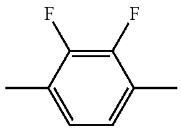 | B(2F,3F) |
| 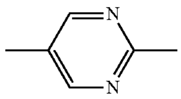 | Py |

TABLE-continued

| Method for Description of Compounds using Symbols $R—(A_1)—Z_1— . . . —Z_n—(A_n)—R'$ | |
|---|---|
| 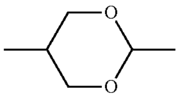 | G |
| 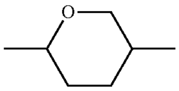 | Dh |
| 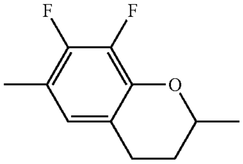 | Cro |

5) Examples of Description

Example 1 3-HH-V

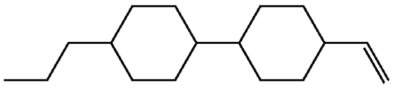

Example 2 3-BB(F,F)XB(F,F)-F

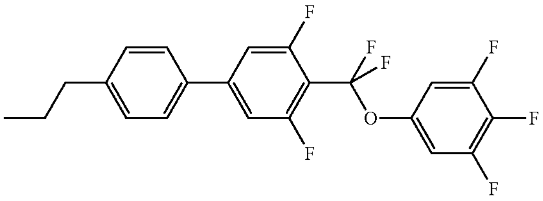

Example 3 3-HH-4

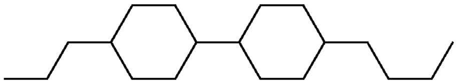

Example 4 3-HBB(2F,3F)-O2

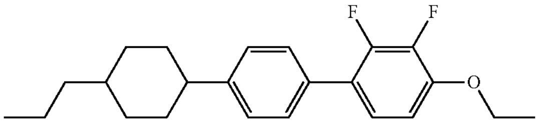

Example 6

| | | |
|---|---|---|
| 3-HB-O2 | (13-5) | 10% |
| 5-HB-CL | (2-2) | 10% |
| 3-HBB(F,F)-F | (3-24) | 10% |
| 3-PyB(F)-F | (2-15) | 10% |
| 5-PyB(F)-F | (2-15) | 10% |
| 3-PyBB-F | (3-80) | 10% |
| 4-PyBB-F | (3-80) | 10% |
| 5-PyBB-F | (3-80) | 10% |
| 5-HBB(F)B-2 | (15-5) | 10% |
| 5-HBB(F)B-3 | (15-5) | 10% |

To the composition described above, compound (No. 1) described below was added at a ratio of 0.3% by weight.

No. 1

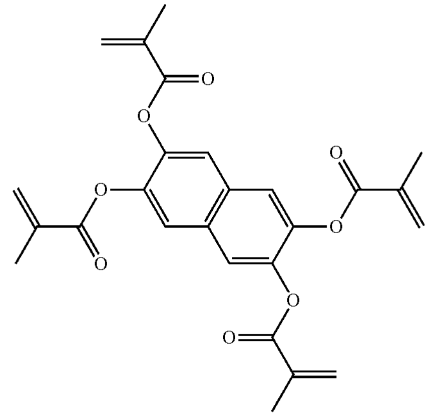

NI=100.8° C.; Δn=0.192; Δ∈=8.2; η=41.0 mPa·s.

Example 7

| | | |
|---|---|---|
| 2-HB-C | (5-1) | 5% |
| 3-HB-C | (5-1) | 12% |
| 3-HB-O2 | (13-5) | 15% |
| 2-BTB-1 | (13-10) | 3% |
| 3-HHB-F | (3-1) | 4% |
| 3-HHB-1 | (14-1) | 8% |
| 3-HHB-O1 | (14-1) | 5% |
| 3-HHB-3 | (14-1) | 14% |
| 3-HHEB-F | (3-10) | 4% |
| 5-HHEB-F | (3-10) | 4% |
| 2-HHB(F)-F | (3-2) | 7% |
| 3-HHB(F)-F | (3-2) | 7% |
| 5-HHB(F)-F | (3-2) | 7% |
| 3-HHB(F,F)-F | (3-3) | 5% |

To the composition described above, compound (No. 51) described below was added at a ratio of 0.25% by weight.

No. 51

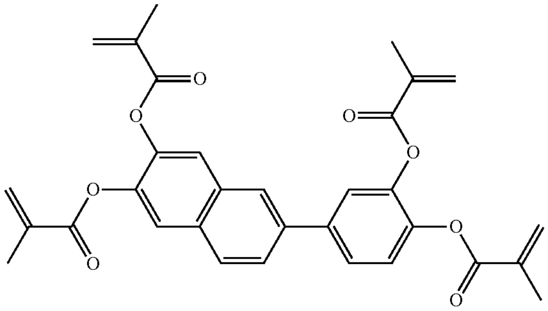

NI=100.5° C.; Δn=0.100; Δ∈=4.6; η=17.9 mPa·s.

Example 8

| | | |
|---|---|---|
| 3-HHB(F,F)-F | (3-3) | 9% |
| 3-H2HB(F,F)-F | (3-15) | 8% |
| 4-H2HB(F,F)-F | (3-15) | 8% |
| 5-H2HB(F,F)-F | (3-15) | 8% |
| 3-HBB(F,F)-F | (3-24) | 21% |

-continued

| | | |
|---|---|---|
| 5-HBB(F,F)-F | (3-24) | 20% |
| 3-H2BB(F,F)-F | (3-27) | 10% |
| 5-HHBB(F,F)-F | (4-6) | 3% |
| 5-HHEBB-F | (4-17) | 2% |
| 3-HH2BB(F,F)-F | (4-15) | 3% |
| 1O1-HBBH-4 | (15-1) | 4% |
| 1O1-HBBH-5 | (15-1) | 4% |

To the composition described above, compound (No. 151) described below was added at a ratio of 0.1% by weight.

No. 151

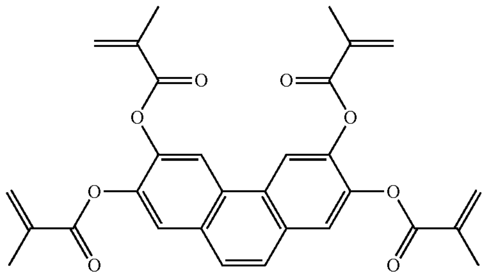

NI=97.8° C.; Δn=0.116; Δ∈=9.0; η=35.0 mPa·s.

Example 9

| | | |
|---|---|---|
| 5-HB-CL | (2-2) | 11% |
| 3-HH-4 | (13-1) | 8% |
| 3-HHB-1 | (14-1) | 5% |
| 3-HHB(F,F)-F | (3-3) | 8% |
| 3-HBB(F,F)-F | (3-24) | 20% |
| 5-HBB(F,F)-F | (3-24) | 15% |
| 3-HHEB(F,F)-F | (3-12) | 10% |
| 4-HHEB(F,F)-F | (3-12) | 3% |
| 5-HHEB(F,F)-F | (3-12) | 3% |
| 2-HBEB(F,F)-F | (3-39) | 3% |
| 3-HBEB(F,F)-F | (3-39) | 5% |
| 5-HBEB(F,F)-F | (3-39) | 3% |
| 3-HHBB(F,F)-F | (4-6) | 6% |

To the composition described above, compound (No. 102) described below was added at a ratio of 0.3% by weight.

No. 102

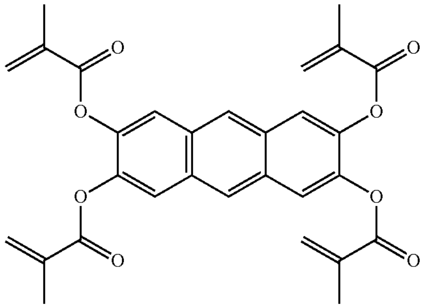

NI=80.2° C.; Δn=0.103; Δ∈=8.7; η=22.4 mPa·s.

Example 10

| | | |
|---|---|---|
| 5-HB-CL | (2-2) | 3% |
| 7-HB(F)-F | (2-3) | 7% |
| 3-HH-4 | (13-1) | 9% |
| 3-HH-EMe | (13-2) | 23% |
| 3-HHEB-F | (3-10) | 8% |
| 5-HHEB-F | (3-10) | 8% |
| 3-HHEB(F,F)-F | (3-12) | 10% |
| 4-HHEB(F,F)-F | (3-12) | 5% |
| 4-HGB(F,F)-F | (3-103) | 5% |
| 5-HGB(F,F)-F | (3-103) | 6% |
| 2-H2GB(F,F)-F | (3-106) | 4% |
| 3-H2GB(F,F)-F | (3-106) | 5% |
| 5-GHB(F,F)-F | (3-109) | 7% |

To the composition described above, compound (No. 1) described below was added at a ratio of 0.2% by weight.

No. 1

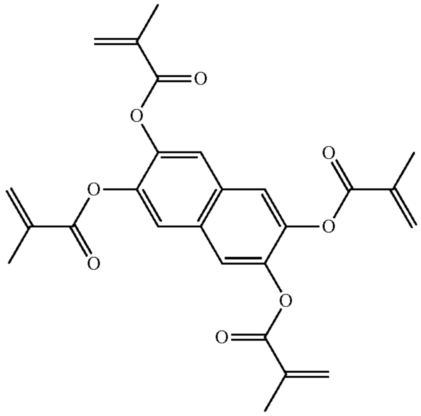

NI=79.4° C.; Δn=0.064; Δ∈=5.7; η=19.9 mPa·s.

Example 11

| | | |
|---|---|---|
| 3-HB-O1 | (13-5) | 15% |
| 3-HH-4 | (13-1) | 5% |
| 3-HB(2F,3F)-O2 | (6-1) | 12% |
| 5-HB(2F,3F)-O2 | (6-1) | 12% |
| 2-HHB(2F,3F)-1 | (7-1) | 12% |
| 3-HHB(2F,3F)-1 | (7-1) | 12% |
| 3-HHB(2F,3F)-O2 | (7-1) | 13% |
| 5-HHB(2F,3F)-O2 | (7-1) | 13% |
| 3-HHB-1 | (14-1) | 6% |

To the composition described above, compound (No. 51) described below was added at a ratio of 0.4% by weight.

No. 51

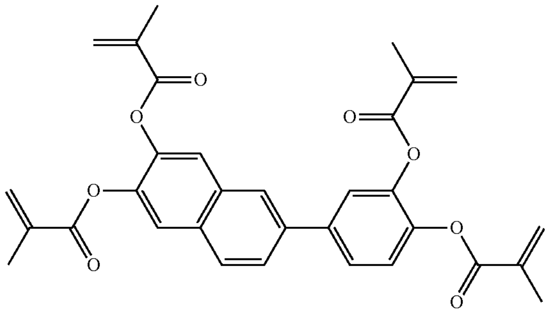

NI=86.5° C.; Δn=0.090; Δ∈=−3.4; η=35.3 mPa·s.

Example 12

| | | |
|---|---|---|
| 3-HH-4 | (13-1) | 8% |
| 3-H2B(2F,3F)-O2 | (6-4) | 22% |
| 5-H2B(2F,3F)-O2 | (6-4) | 22% |
| 2-HHB(2F,3CL)-O2 | (7-12) | 2% |
| 3-HHB(2F,3CL)-O2 | (7-12) | 3% |
| 4-HHB(2F,3CL)-O2 | (7-12) | 2% |
| 5-HHB(2F,3CL)-O2 | (7-12) | 2% |
| 3-HBB(2F,3F)-O2 | (7-7) | 9% |
| 5-HBB(2F,3F)-O2 | (7-7) | 9% |
| V-HHB-1 | (14-1) | 6% |
| 3-HHB-3 | (14-1) | 6% |
| 3-HHEBH-3 | (15-6) | 3% |
| 3-HHEBH-4 | (15-6) | 3% |
| 3-HHEBH-5 | (15-6) | 3% |

To the composition described above, compound (No. 151) described below was added at a ratio of 0.35% by weight.

No. 151

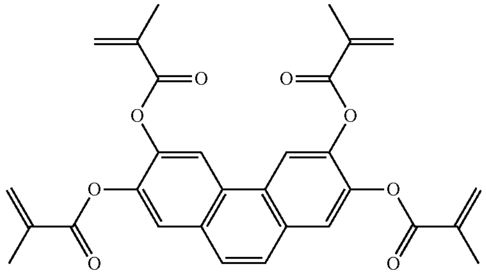

NI=91.5° C.; Δn=0.100; Δ∈=−4.1; η=29.2 mPa·s.

Example 13

| | | |
|---|---|---|
| 2-HH-5 | (13-1) | 3% |
| 3-HH-4 | (13-1) | 15% |
| 3-HH-5 | (13-1) | 4% |
| 3-HB-O2 | (13-5) | 12% |
| 3-H2B(2F,3F)-O2 | (6-4) | 15% |
| 5-H2B(2F,3F)-O2 | (6-4) | 15% |
| 3-HHB(2F,3CL)-O2 | (7-12) | 5% |
| 2-HBB(2F,3F)-O2 | (7-7) | 3% |
| 3-HBB(2F,3F)-O2 | (7-7) | 9% |
| 5-HBB(2F,3F)-O2 | (7-7) | 9% |
| 3-HHB-1 | (14-1) | 3% |
| 3-HHB-3 | (14-1) | 4% |
| 3-HHB-O1 | (14-1) | 3% |

To the composition described above, compound (No. 102) described below was added at a ratio of 0.15% by weight.

No. 102

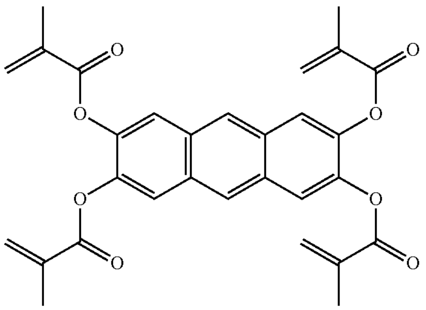

NI=75.7° C.; Δn=0.093; Δ∈=−4.1; η=19.2 mPa·s.

Example 14

| | | |
|---|---|---|
| 2-HH-3 | (13-1) | 21% |
| 3-HH-4 | (13-1) | 9% |
| 1-BB-3 | (13-8) | 9% |
| 3-HB-O2 | (13-5) | 2% |
| 3-BB(2F,3F)-O2 | (6-3) | 9% |
| 5-BB(2F,3F)-O2 | (6-3) | 6% |
| 2-HH1OB(2F,3F)-O2 | (7-5) | 13% |
| 3-HH1OB(2F,3F)-O2 | (7-5) | 21% |
| 3-HHB-1 | (14-1) | 5% |
| 3-HHB-O1 | (14-1) | 3% |
| 5-B(F)BB-2 | (14-6) | 2% |

To the composition described above, compound (No. 1) described below was added at a ratio of 0.25% by weight.

No. 1

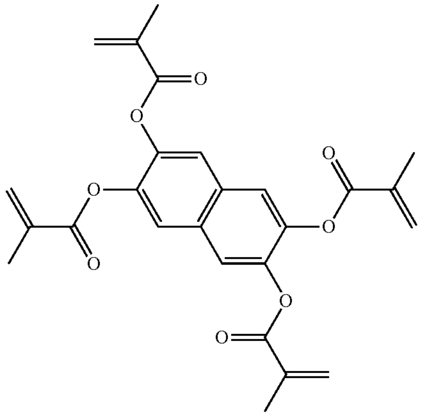

NI=74.3° C.; Δn=0.097; Δ∈=−3.2; η=15.3 mPa·s.

Example 15

| | | |
|---|---|---|
| 2-HH-3 | (13-1) | 16% |
| 7-HB-1 | (13-5) | 10% |
| 5-HB-O2 | (13-5) | 8% |
| 3-HB(2F,3F)-O2 | (6-1) | 12% |
| 5-HB(2F,3F)-O2 | (6-1) | 16% |
| 3-HHB(2F,3CL)-O2 | (7-12) | 3% |

-continued

| | | |
|---|---|---|
| 4-HHB(2F,3CL)-O2 | (7-12) | 3% |
| 5-HHB(2F,3CL)-O2 | (7-12) | 2% |
| 3-HH1OCro(7F,8F)-5 | (9-3) | 5% |
| 5-HBB(F)B-2 | (15-5) | 10% |
| 5-HBB(F)B-3 | (15-5) | 10% |
| 3-HDhB(2F,3F)-O2 | (7-3) | 5% |

To the composition described above, compound (No. 51) described below was added at a ratio of 0.3% by weight.

No. 51

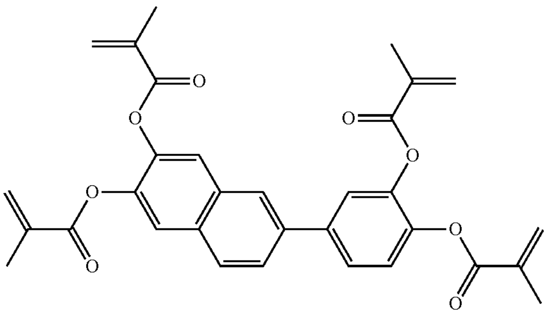

NI=82.0° C.; Δn=0.106; Δ∈=−2.6; η=24.8 mPa·s.

Example 16

| | | |
|---|---|---|
| 1-BB-3 | (13-8) | 10% |
| 3-HH-V | (13-1) | 29% |
| 3-BB(2F,3F)-O2 | (6-3) | 13% |
| 2-HH1OB(2F,3F)-O2 | (7-5) | 20% |
| 3-HH1OB(2F,3F)-O2 | (7-5) | 14% |
| 3-HHB-1 | (14-1) | 8% |
| 5-B(F)BB-2 | (14-8) | 6% |

To the composition described above, compound (No. 151) described below was added at a ratio of 0.3% by weight.

No. 151

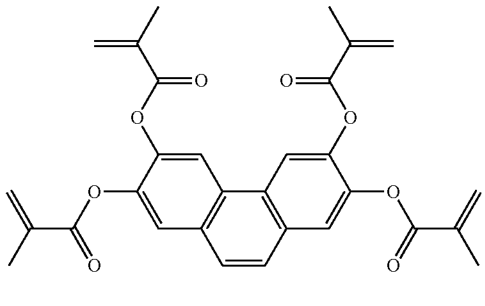

NI=74.5° C.; Δn=0.106; Δ∈=−3.0; η=14.7 mPa's.

Example 17

| | | |
|---|---|---|
| 1V2-BEB(F,F)-C | (5-13) | 8% |
| 3-HB-C | (5-1) | 16% |
| 2-BTB-1 | (13-10) | 10% |
| 5-HH-VFF | (13-1) | 30% |

-continued

| | | |
|---|---|---|
| 3-HHB-1 | (14-1) | 4% |
| VFF-HHB-1 | (14-1) | 8% |
| VFF2-HHB-1 | (14-1) | 11% |
| 3-H2BTB-2 | (14-17) | 5% |
| 3-H2BTB-3 | (14-17) | 4% |
| 3-H2BTB-4 | (14-17) | 4% |

To the composition described above, compounds (No. 1) and (No. 102) described below each were added at a ratio of 0.2% by weight.

No. 1

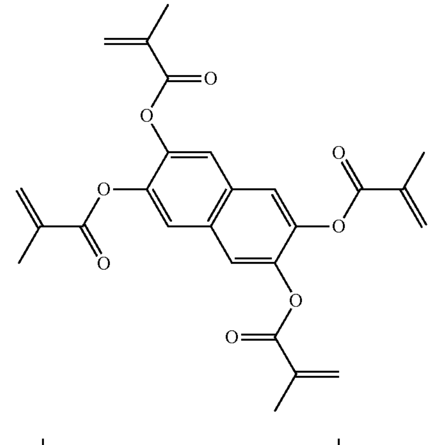

No. 102

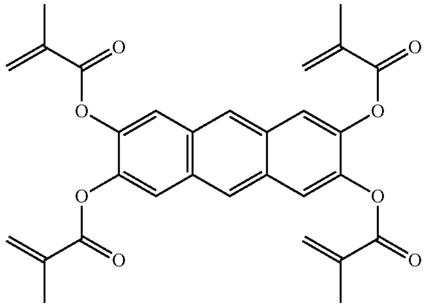

NI=80.6° C.; Δn=0.131; Δ∈=7.7; η=12.4 mPa·s.

Example 18

| | | |
|---|---|---|
| 5-HB(F)B(F,F)XB(F,F)-F | (4-41) | 5% |
| 3-BB(F)B(F,F)XB(F,F)-F | (4-47) | 3% |
| 4-BB(F)B(F,F)XB(F,F)-F | (4-47) | 7% |
| 5-BB(F)B(F,F)XB(F,F)-F | (4-47) | 3% |
| 3-HH-V | (13-1) | 41% |
| 3-HH-V1 | (13-1) | 7% |
| 3-HHEH-5 | (14-13) | 3% |
| 3-HHB-1 | (14-1) | 4% |
| V-HHB-1 | (14-1) | 5% |
| V2-BB(F)B-1 | (14-6) | 5% |
| 1V2-BB-F | (2-1) | 3% |
| 3-BB(F,F)XB(F,F)-F | (3-97) | 11% |
| 3-HHBB(F,F)-F | (4-6) | 3% |

To the composition described above, compound (No. 51) described below was added at a ratio of 0.3% by weight.

No. 51

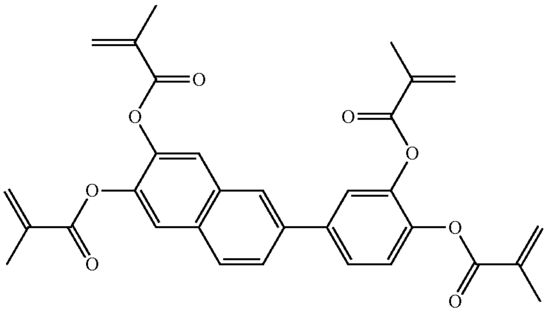

NI=81.9° C.; Δn=0.105; Δ∈=6.3; η=12.0 mPa·s.

Example 19

| | | |
|---|---|---|
| 3-GB(F)B(F,F)XB(F,F)-F | (4-57) | 5% |
| 3-BB(F)B(F,F)XB(F,F)-F | (4-47) | 3% |
| 4-BB(F)B(F,F)XB(F,F)-F | (4-47) | 7% |
| 5-BB(F)B(F,F)XB(F,F)-F | (4-47) | 3% |
| 3-HH-V | (13-1) | 41% |
| 3-HH-V1 | (13-1) | 7% |
| 3-HHEH-5 | (14-13) | 3% |
| 3-HHB-1 | (14-1) | 4% |
| V-HHB-1 | (14-1) | 5% |
| V2-BB(F)B-1 | (14-6) | 5% |
| 1V2-BB-F | (2-1) | 3% |
| 3-BB(F,F)XB(F,F)-F | (3-97) | 6% |
| 3-GB(F,F)XB(F,F)-F | (3-113) | 5% |
| 3-HHBB(F,F)-F | (4-6) | 3% |

To the composition described above, compound (No. 151) described below was added at a ratio of 0.3% by weight.

No. 151

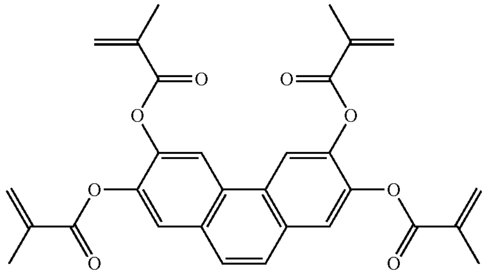

NI=81.3° C.; Δn=0.103; Δ∈=7.4; η=12.8 mPa·s.

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

INDUSTRIAL APPLICABILITY

A liquid crystal display device having a mode such as a PSA mode can be prepared by polymerizing a polymerizable composition containing compound (1) and a liquid crystal composition. The polymerizable compound can also be used as a raw material of an optical anisotropic body.

What is claimed is:

1. A compound represented by formula (1):

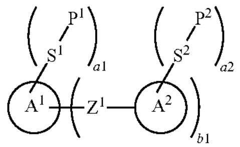

(1)

wherein, in formula (1), all of a1 moieties of $P^1$ and a2 moieties of $P^2$ are identically a group selected from groups represented by formulas (P-1), (P-2) and (P-3), and in formula (P-1), M is hydrogen, fluorine, —$CH_3$ or —$CF_3$:

(P-1)

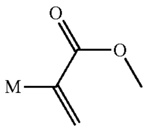

(P-2)

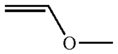

(P-3)

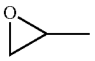

$S^1$ and $S^2$ are independently a single bond or alkylene having 1 to 6 carbons, and in the alkylene, at least one of —$CH_2$— may be replaced by —O—, —COO— or —OCO—, at least one of —$CH_2$—$CH_2$— may be replaced by —CH═CH— or —C≡C—, and in the group, at least one of hydrogen may be replaced by halogen;

a1 and a2 are independently 0, 1, 2, 3 or 4, and a sum of a1 and a2 is 4;

ring $A^1$ is naphthalene, anthracene or phenanthrene, ring $A^2$ is cyclohexyl, phenyl, naphthyl, anthracenyl or phenanthrenyl, and in the rings, at least one of hydrogen may be replaced by halogen, alkyl having 1 to 10 carbons, or alkyl having 1 to 10 carbons in which at least one of hydrogen is replaced by halogen;

$Z^1$ is a single bond, —CO—, —COO—, —OCO—, —CH═CH—, —C≡C—, —CH═C($CH_3$)—, —C($CH_3$)═CH—, —C($CH_3$)═C($CH_3$)—, —CH═CH—COO—, —OCO—CH═CH—, —C($CH_3$)═CH—COO—, —OCO—CH═CH($CH_3$)—, —CH═C($CH_3$)—COO—, —OCO—C($CH_3$)═CH—, —C($CH_3$)═C($CH_3$)—COO—, —OCO—C($CH_3$)═C($CH_3$)—, —CH═CH—CO—, —CO—CH═CH—, —CH═CH—$CH_2$O—, —O$CH_2$—CH═CH—, —CH═CH—O$CH_2$— or —$CH_2$O—CH═CH—; and b1 is 0, 1, 2, 3 or 4;

wherein when b1 is 0, ring $A^1$ is anthracene or phenanthrene.

2. The compound according to claim 1, wherein, in formula (1), all of a1 moieties of $P^1$ and a2 moieties of $P^2$ are identi cally a group represented by formula (P-1), and in formula (P-1), M is hydrogen, fluorine, $—CH_3$ or $—CF_3$:

(P-1)

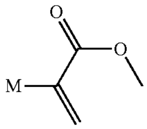

$S^1$ and $S^2$ are independently a single bond or alkylene having 1 to 6 carbons, and in the alkylene, at least one of $—CH_2—$ may be replaced by —O—, —COO— or —OCO—, at least one of $—CH_2—CH_2—$ may be replaced by —CH═CH— or —C≡C—, and in the groups, at least one of hydrogen may be replaced by fluorine or chlorine;

a1 and a2 are independently 0, 1, 2, 3 or 4, and a sum of a1 and a2 is 4;

ring $A^1$ is naphthalene, anthracene or phenanthrene, ring $A^2$ is phenyl, naphthyl, anthracenyl or phenanthrenyl, and in the rings, at least one of hydrogen may be replaced by fluorine, chlorine, alkyl having 1 to 5 carbons, fluorinated alkyl having 1 to 5 carbons, or alkyl having 1 to 5 carbons in which at least one of hydrogen is replaced by chlorine;

$Z^1$ is a single bond, —CO—, —COO—, —OCO—, —CH═CH—, —C≡C—, —CH═CH—COO—, —OCO—CH═CH—, —CO—CH═CH—, —CH═CH—CO—, $—CH═CH—CH_2O—$, $—OCH_2—CH═CH—$, $—CH═CH—OCH_2—$or $—CH_2O—CH═CH—$; and b1 is 0, 1, and 2 or 3;

wherein when b1 is 0, ring $A^1$ is anthracene or phenanthrene.

3. The compound according to claim 1, wherein, in formula (1), all of a1 moieties of $P^1$ and a2 moieties of $P^2$ are identically $—OCO—HC═CH_2$ or $—OCO—(CH_3)C═CH_2$;

$S^1$ and $S^2$ are independently a single bond, —COO—, —OCO—, $—CH_2—$, $—CH_2O—$, $—OCH_2—$, $—(CH_2)_2—$, $—(CH_2)_2—O—$, $—O—(CH_2)_2—$, —CH═CH—, —CH═CH—O—, —O—CH═CH—, —C≡C—, —C≡C—O—, —O—C≡C—, $—(CH_2)_3—$, $—(CH_2)_3—O—$, $—O—(CH_2)_3—$, $—(CH_2)_4—$, $—(CH_2)_4—O—$ or $—O—(CH_2)_4—$;

a1 and a2 are independently 0, 1, 2, 3 or 4, and a sum of a1 and a2 is 4;

ring $A^1$ is naphthalene, anthracene or phenanthrene, ring $A^2$ is phenyl, and in the rings, at least one of hydrogen may be replaced by fluorine, chlorine, $—CH_3$, $—CHF_2$ or $—CF_3$;

$Z^1$ is a single bond, —CH═CH—, —CH═CH—COO—, —OCO—CH═CH—, $—CH═CH—CH_2O—$, $—OCH_2—CH═CH—$, $—CH═CH—OCH_2—$ or $—CH_2O—CH═CH—$; and b1 is 0, 1 or 2;

wherein when b1 is 0, ring $A^1$ is anthracene or phenanthrene.

4. The compound according to claim 1, represented by any one of formulas (1-1) to (1-13):

(1-1)

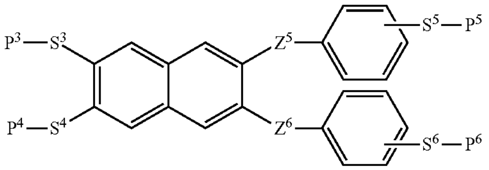

(1-2)

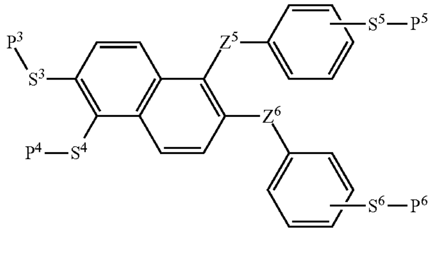

(1-3)

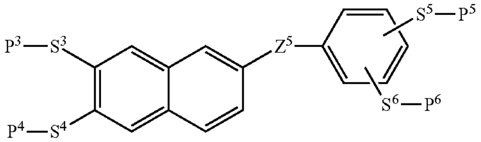

(1-4)

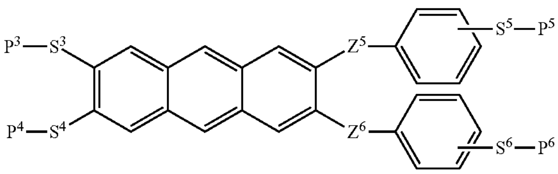

(1-5)

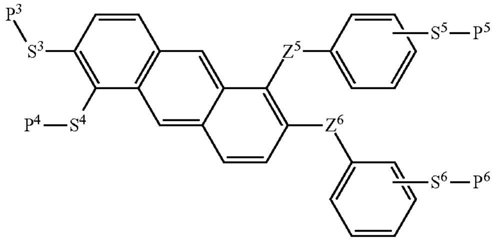

(1-6)

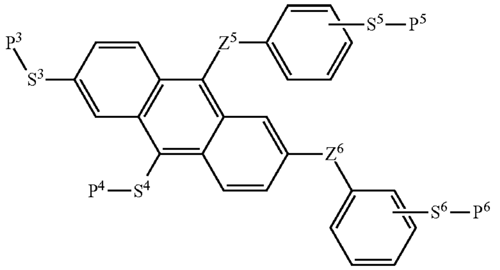

(1-7)

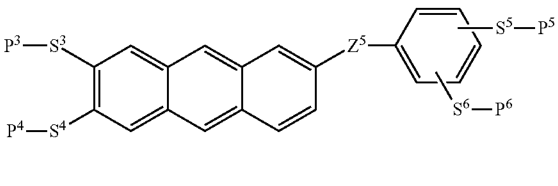

-continued (1-8)

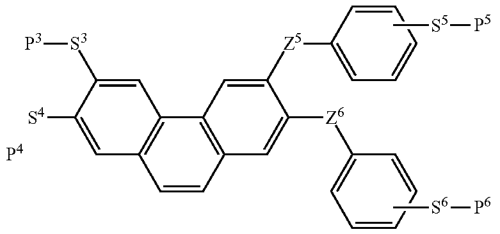

(1-9)

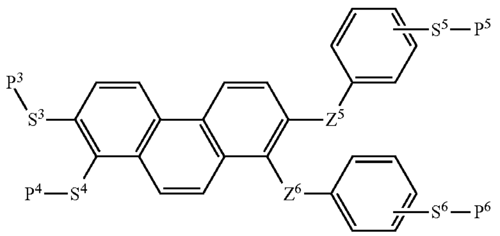

(1-10)

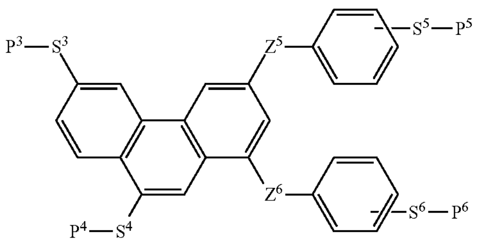

(1-11)

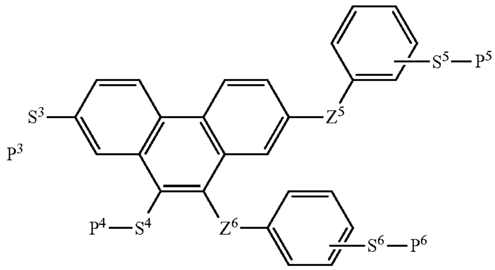

(1-12)

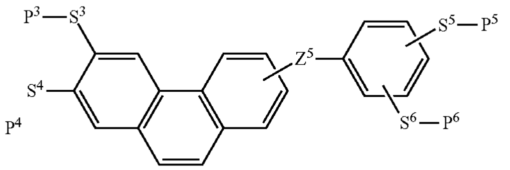

(1-13)

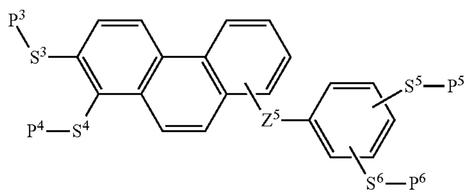

wherein, in formulas (1-1) to (1-13), all of $P^3$, $P^4$, $P^5$ and $P^6$ are identically a group represented by formula (P-1), and in formula (P-1), M is hydrogen, fluorine, $—CH_3$ or $—CF_3$;

(P-1)

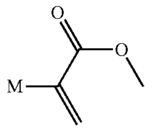

$S^3$, $S^4$, $S^5$ and $S^6$ are independently a single bond or alkylene having 1 to 6 carbons, and in the alkylene, at least one of $—CH_2—$ may be replaced by —O—, —COO— or —OCO—, at least one of $—CH_2—CH_2—$ may be replaced by —CH═CH— or —C≡C—, and at least one of hydrogen may be replaced by fluorine or chlorine; and $Z^5$ and $Z^6$ are independently a single bond, —CO—, —COO—, —OCO—, —CH═CH—, —C≡C—, —CH═CH—COO—, —OCO—CH═CH—, $—OCO—C(CH_3)═CH—$, —CO—CH═CH—, —CH═CH—CO—, $—CH═CH—CH_2O—$, $—OCH_2—CH═CH—$, $—CH═CH—OCH_2—$ or $—CH_2O—CH═CH—$.

5. The compound according to claim 4, wherein, in formulas (1-1) to (1-13), all of $P^3$, $P^4$, $P^5$ and $P^6$ are —OCO—$HC═CH_2$ or $—OCO—(CH_3)C═CH_2$; $S^3$, $S^4$, $S^5$ and $S^6$ are a single bond; and $Z^5$ and $Z^6$ are a single bond.

6. The compound according to claim 1, represented by any one of formulas (1-16) to (1-22):

(1-16)

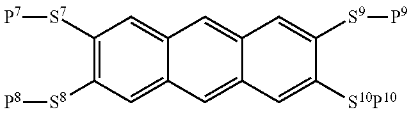

(1-17)

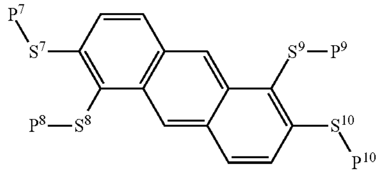

(1-18)

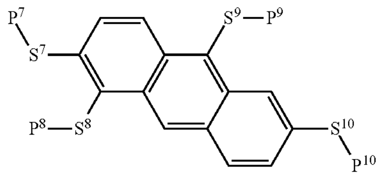

(1-19)

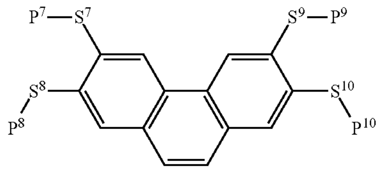

(1-20)

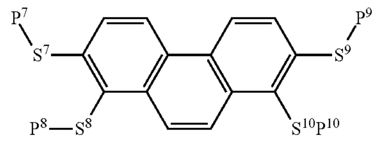

-continued (1-21)

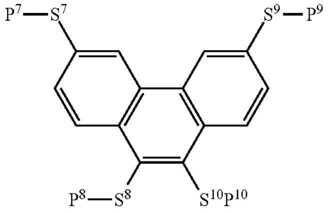

(1-22)

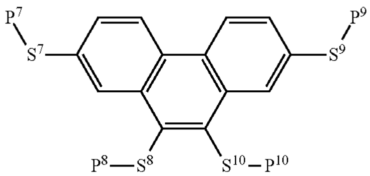

wherein, in formulas (1-16) to (1-22), all of $P^7$, $P^8$, $P^9$ and $P^{10}$ are identical, and a group represented by formula (P-1), and in formula (P-1), M is hydrogen, fluorine, $—CH_3$ or $—CF_3$;

(P-1)

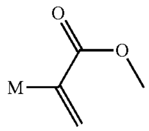

$S^7$, $S^8$, $S^9$ and $S^{10}$ are independently a single bond or alkylene having 1 to 6 carbons, and in the alkylene, at least one of $—CH_2—$ may be replaced by —O—, —COO— or —OCO—, at least one of $—CH_2—CH_2—$ may be replaced by —CH═CH— or —C≡C—, and in the groups, at least one of hydrogen may be replaced by fluorine or chlorine.

7. The compound according to claim 6, wherein, in formulas (1-16) to (1-22), all of $P^7$, $P^8$, $P^9$ and $P^{10}$ are —OCO—HC═$CH_2$ or —OCO—$(CH_3)$C═$CH_2$; and $S^7$, $S^8$, $S^9$ and $S^{10}$ are a single bond.

8. The compound according to claim 1, represented by formula (1-3-1) or (1-19-1):

(1-3-1)

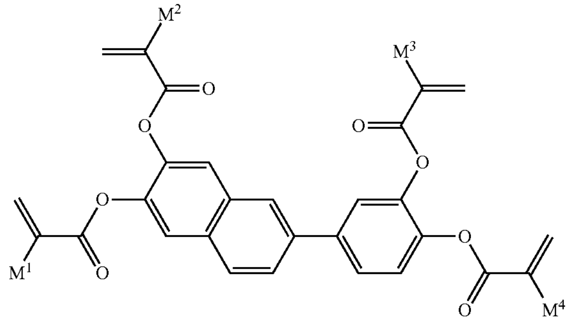

-continued (1-19-1)

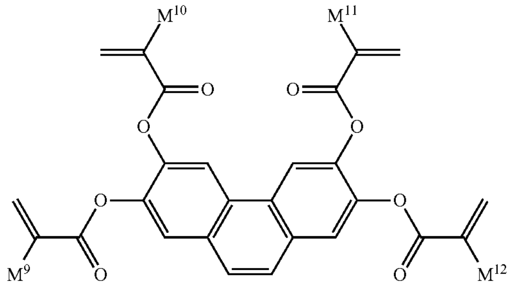

wherein, in formula (1-3-1) or (1-19-1), all of $M^1$ to $M^4$ and $M^9$ to $M^{12}$ are identically hydrogen, fluorine, $—CH_3$ or $—CF_3$.

9. A polymer obtained from the compound according to claim 1.

10. A liquid crystal composition, comprising at least one compound according to claim 1.

11. The liquid crystal composition according to claim 10, further comprising at least one compound selected from the group of compounds represented by formulas (2) to (4):

(2)

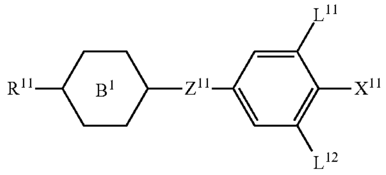

(3)

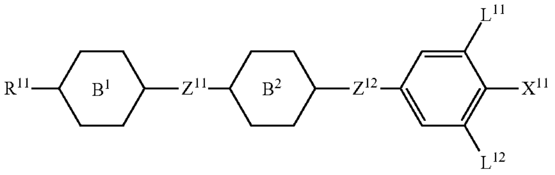

(4)

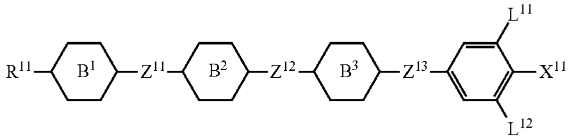

wherein, in formulas (2) to (4), $R^{11}$ is alkyl having 1 to 10 carbons or alkenyl having 2 to 10 carbons, and in the alkyl and the alkenyl, at least one of hydrogen may be replaced by fluorine, and at least one of $—CH_2—$ may be replaced by —O—;

$X^{11}$ is fluorine, chlorine, $—OCF_3$, $—OCHF_2$, $—CF_3$, $—CHF_2$, $—CH_2F$, $—OCF_2CHF_2$ or $—OCF_2CHFCF_3$;

ring $B^1$, ring $B^2$ and ring $B^3$ are independently 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{11}$, $Z^{12}$ and $Z^{13}$ are independently a single bond, $-CH_2CH_2-$, $-CH{=}CH-$, $-C{\equiv}C-$, $-COO-$, $-CF_2O-$, $-OCF_2-$, $-CH_2O-$ or $-(CH_2)_4-$; and $L^{11}$ and $L^{12}$ are independently hydrogen or fluorine.

ring $C^1$ is 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{14}$ is a single bond, $-CH_2CH_2-$, $-C{\equiv}C-$, $-COO-$, $-CF_2O-$, $-OCF_2-$ or $-CH_2O-$;

$L^{13}$ and $L^{14}$ are independently hydrogen or fluorine; and i is 1, 2, 3 or 4.

13. The liquid crystal composition according to claim 10, further comprising at least one compound selected from the group of compounds represented by formulas (6) to (12):

(6)

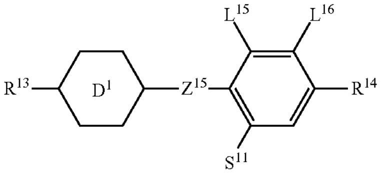

(7)

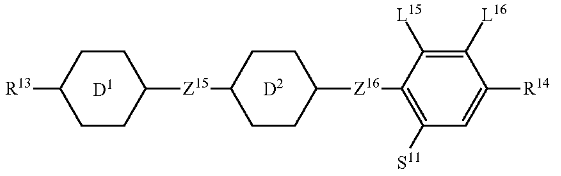

(8)

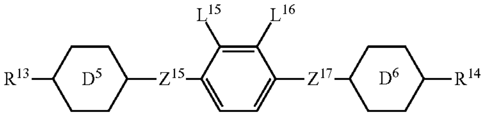

(9)

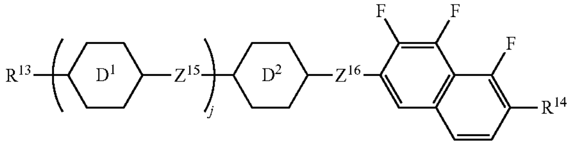

(10)

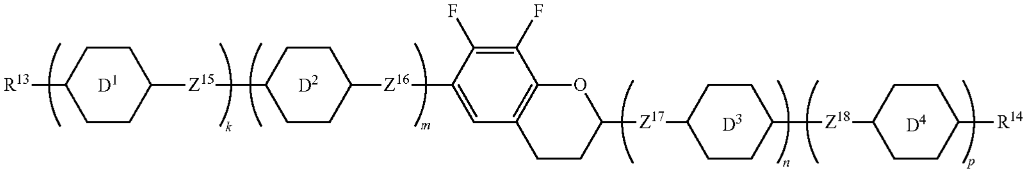

(11)

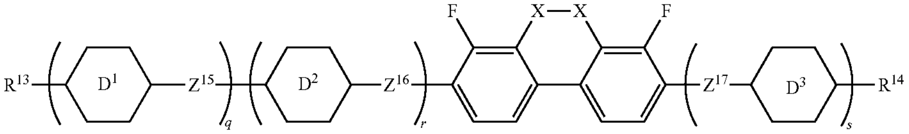

(12)

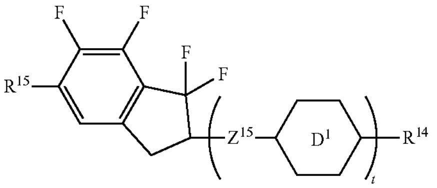

12. The liquid crystal composition according to claim 10, further comprising at least one compound selected from the group of compounds represented by formula (5):

(5)

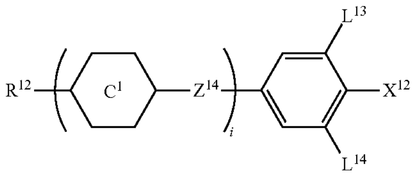

wherein, in formula (5), $R^{12}$ is alkyl having 1 to 10 carbons or alkenyl having 2 to 10 carbons, and in the alkyl and the alkenyl, at least one of hydrogen may be replaced by fluorine, and at least one of $-CH_2-$ may be replaced by $-O-$;

$X^{12}$ is $-C{\equiv}N$ or $-C{\equiv}C-C{\equiv}N$;

wherein, in formulas (6) to (12), $R^{13}$ and $R^{14}$ are independently alkyl having 1 to 10 carbons or alkenyl having 2 to 10 carbons, and in the alkyl and the alkenyl, at least one of $-CH_2-$ may be replaced by $-O-$, and at least one of hydrogen may be replaced by fluorine;

$R^{15}$ is hydrogen, fluorine, alkyl having 1 to 10 carbons or alkenyl having 2 to 10 carbons, and in the alkyl and the alkenyl, at least one of $-CH_2-$ may be replaced by $-O-$, and at least one of hydrogen may be replaced by fluorine;

$S^{11}$ is hydrogen or methyl;

X is $-CF_2-$, $-O-$ or $-CHF-$;

ring $D^1$, ring $D^2$, ring $D^3$ and ring $D^4$ are independently 1,4-cyclohexylene, 1,4-cyclohexenylene, 1,4-phenylene in which at least one of hydrogen may be replaced by fluorine, tetrahydropyran-2,5-diyl or decahydronaphthalene-2,6-diyl;

ring $D^5$ and ring $D^6$ are independently 1,4-cyclohexylene, 1,4-cyclohexenylene, 1,4-phenylene, tetrahydropyran-2,5-diyl or decahydronaphthalene-2,6-diyl;

$Z^{15}$, $Z^{16}$, $Z^{17}$ and $Z^{18}$ are independently a single bond, $—CH_2CH_2—$, $—COO—$, $—CH_2O—$, $—OCF_2—$ or $—OCF_2CH_2CH_2—$;

$L^{15}$ and $L^{16}$ are independently fluorine or chlorine; and j, k, m, n, p, q, r and s are independently 0 or 1, a sum of k, m, n and p is 1 or 2, a sum of q, r and s is 0, 1, 2 or 3, and t is 1, 2 or 3.

14. The liquid crystal composition according to claim 10, further comprising at least one compound selected from the group of compounds represented by formulas (13) to (15):

(13)

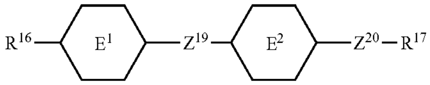

(14)

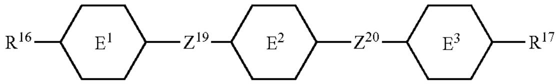

-continued (15)

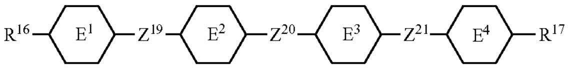

wherein, in formulas (13) to (15), $R^{16}$ and $R^{17}$ are independently alkyl having 1 to 10 carbons or alkenyl having 2 to 10 carbons, and in the alkyl or the alkenyl, at least one of $—CH_2—$ may be replaced by —O—, and at least one of hydrogen may be replaced by fluorine;

ring $E^1$, ring $E^2$, ring $E^3$ and ring $E^4$ are independently 1,4-cyclohexylene, 1,4-phenylene, 2-fluoro-1,4-phenylene, 2,5-difluoro-1,4-phenylene or pyrimidine-2,5-diyl; and $Z^{19}$, $Z^{20}$ and $Z^{21}$ are independently a single bond, $—CH_2CH_2—$, —CH═CH—, —C≡C— or —COO—.

15. The liquid crystal composition according to claim 10, further comprising at least one of a polymerizable compound, an optically active compound, an antioxidant, an ultraviolet light absorber, a light stabilizer, a heat stabilizer, an antifoaming agent, a polymerization initiator and a polymerization inhibitor.

16. A liquid crystal display device, comprising the liquid crystal composition according to claim 10.

* * * * *